(12) United States Patent
Yamauchi et al.

(10) Patent No.: US 11,884,678 B2
(45) Date of Patent: Jan. 30, 2024

(54) METHOD FOR PRODUCING A SPIROOXINDOLE DERIVATIVE

(71) Applicant: Daiichi Sankyo Company, Limited, Tokyo (JP)

(72) Inventors: Motoshi Yamauchi, Kanagawa (JP); Keiji Nakayama, Kanagawa (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

(21) Appl. No.: 17/081,452

(22) Filed: Oct. 27, 2020

(65) Prior Publication Data

US 2021/0323970 A1  Oct. 21, 2021
US 2022/0259216 A9  Aug. 18, 2022

Related U.S. Application Data

(62) Division of application No. 16/031,165, filed on Jul. 10, 2018, now Pat. No. 10,851,111, which is a division of application No. 14/916,677, filed as application No. PCT/JP2014/073233 on Sep. 3, 2014, now Pat. No. 10,030,028.

(30) Foreign Application Priority Data

Sep. 4, 2013  (JP) .................... 2013-182928

(51) Int. Cl.
| | |
|---|---|
| *C07D 487/10* | (2006.01) |
| *C07D 491/20* | (2006.01) |
| *B01J 31/02* | (2006.01) |
| *B01J 31/04* | (2006.01) |
| *B01J 31/22* | (2006.01) |
| *C07B 53/00* | (2006.01) |
| *B01J 31/24* | (2006.01) |
| *B01J 31/18* | (2006.01) |
| *B01J 31/14* | (2006.01) |

(52) U.S. Cl.
CPC ............ *C07D 487/10* (2013.01); *B01J 31/02* (2013.01); *B01J 31/04* (2013.01); *B01J 31/143* (2013.01); *B01J 31/189* (2013.01); *B01J 31/22* (2013.01); *B01J 31/226* (2013.01); *B01J 31/2295* (2013.01); *B01J 31/2409* (2013.01); *B01J 31/2414* (2013.01); *B01J 31/2452* (2013.01); *B01J 31/2457* (2013.01); *B01J 31/2476* (2013.01); *C07B 53/00* (2013.01); *C07D 491/20* (2013.01); *B01J 2231/32* (2013.01); *B01J 2231/328* (2013.01); *B01J 2531/0205* (2013.01); *B01J 2531/0263* (2013.01); *B01J 2531/0266* (2013.01); *B01J 2531/0272* (2013.01); *B01J 2531/16* (2013.01); *B01J 2531/17* (2013.01); *B01J 2531/842* (2013.01); *B01J 2540/10* (2013.01); *B01J 2540/40* (2013.01)

(58) Field of Classification Search
CPC .................................................. C07D 487/10
See application file for complete search history.

(56) References Cited

U.S. PATENT DOCUMENTS

| 7,737,174 B2 | 6/2010 | Wang et al. |
|---|---|---|
| 7,759,383 B2 | 7/2010 | Wang et al. |
| 10,030,028 B2 | 7/2018 | Yamauchi et al. |
| 10,851,111 B2 | 12/2020 | Yamauchi et al. |
| 2012/0071499 A1 | 3/2012 | Chu et al. |
| 2012/0264738 A1 | 10/2012 | Sugimoto et al. |
| 2012/0289494 A1 | 11/2012 | Wang et al. |
| 2014/0121196 A1 | 5/2014 | Sugimoto et al. |
| 2016/0194331 A1 | 7/2016 | Yamauchi et al. |
| 2018/0319808 A1 | 11/2018 | Yamauchi et al. |
| 2022/0106324 A1 | 4/2022 | Sugimoto et al. |

FOREIGN PATENT DOCUMENTS

| JP | 2000-271485 A | 10/2000 |
|---|---|---|
| JP | 2013-142071 A | 7/2013 |
| TW | 201249842 A1 | 12/2012 |
| WO | WO 2012/121361 A1 | 9/2012 |
| WO | WO 2012/155066 A2 | 11/2012 |
| WO | 2015033974 A1 | 3/2015 |

OTHER PUBLICATIONS

Aguilar; J. Med. Chem. 2014, 57, 10486-10498. https://doi.org/10.1021/jm501541j (Year: 2014).*
U.S. Appl. No. 17/234,404, filed Apr. 19, 2021, Sugimoto et al.
Aldrich Chemistry (2008) "Asymmetric Catalysis. Privileged Ligands and Complexes" Sigma-Aldrich: ChemFiles, vol. 8, No. 2, 92 pages.
Alemparte, C. et al. (2005) "A Convenient Procedure for the Catalytic Asymmetric 1,3-Dipolar Cycloaddition of Azomethine Ylides and Alkenes" Organic Letters, 7(21):4569-4572.
Amedjkough, M. (2005) "Primary amine catalyzed direct asymmetric aldol reaction assisted by water" Tetrahedron: Asymmetry, 16:1411-1414.
Antonchick, A.P. et al. (2011) "Enantioselective synthesis of the spirotryprostatin A scaffold" Tetrahedron, 67:10195-10202.
Antonchick, A.P. et al. (2010) "Highly enantioselective synthesis and cellular evaluation of spirooxindoles inspired by natural products" Nature Chemisty, 2:735-740.
Awata, A. and T. Arai (2012) "Catalytic Asymmetric exo'-Selective [3+2] Cycloaddition for Constructing Stereochemically Diversified Spiro[pyrrolidin-3,3'-oxindole]s," Chem Eur J, 18:8278-8282.

(Continued)

*Primary Examiner* — Daniel R Carcanague
(74) *Attorney, Agent, or Firm* — Mintz Levin Cohn Ferris Glovsky and Popeo, P.C.

(57) ABSTRACT

The present disclosure provides a method for efficiently producing and providing compounds having a spirooxindole skeleton, for example compounds having a spirooxindole skeleton and having antitumor activity that inhibit the interaction between Mdm2 protein and p53 protein, or intermediates thereof, using an asymmetric catalyst. Compounds having optically active tricyclic dispiroindole skeletons are obtained through catalytic asymmetric 1,3-dipolar cycloaddition reaction using ketimine as a reaction substrate and using a chiral ligand and a Lewis acid.

6 Claims, No Drawings

(56) References Cited

OTHER PUBLICATIONS

Cabrera, S. et al. (2005) "Highly Enantioselective Copper(I)-Fesulphos-Catalyzed 1,3-Dipolar Cycloaddition of Azomethine Ylides" J Am Cherm, 127:16394-16395.

Cabrera, S. et al. (2007) "CuI-Fesulphos complexes: efficient chiral catalysts for asymmetric 1,3-dipolar cycloaddition of azomethine ylides" Tetrahedron, 63:6587-6602.

Chen, C. et al. (2003) "Catalytic Asymmetric [3+2] Cycloaddition of Azomethine Ylides. Development of a Versatile Stepwise, Three-Component Reaction for Diversity-Oriented Synthesis" J Am Chem Soc, 125:10174-10175.

Chen, X-H. et al. (2009) "Organocatalytic Synthesis of Spiro[pyrrolidin-3-3'-oxindoles] with High Enantiopurity and Structural Diversity" J Am Chem Soc, 131:13819-13825.

Cheng, M-N. et al. (2011) "Asymmetic Organocatalytic 1,3-Dipolar Cycloaddition of Azomethine Ylide to Methyl 2-(2-Nitrophenyl)acrylate for the Synthesis of Diastereoisomers of Spirotryprostatin A" Organic Letters, 13(9):2418-2421.

Ding, K. et al. (2005) "Structure-Based Design of Potent Non-Peptide MDM2 Inhibitors" J Am Chem Soc, 127:10130-10131.

Ding, K. et al. (2006) "Structure-Based Design of Spiro-oxindoles as Potent, Specific Small-Molecule Inhibitors of the MDM2-p53 Interaction" J Med Chem, 49:3432-3435.

Dörwald, F.Z. (2005) "Preface" in Side Reactions inOrganic Synthesis. Weinheim: Wiley-VGH; p. IX-X.

English Translation of International Search Report dated Dec. 16, 2014, in PCT Application No. PCT/JP2014/073233, 2 pages.

English Translation of Written Opinion dated Dec. 16, 2014, in PCT Application No. PCT/JP2014/073233, 7 pages.

Gothelf, K.V. and K.A. Jørgensen (1998) "Asymmetric 1,3-Dipolar Cycloaddition Reactions" Chem Rev, 98:863-909.

Grigg, R. et al. (1992) "X=Y-ZH Systems as Potential 1,3-Dipoles. Part 39. Metallo-Azomethine Ylides from Aliphatic Aldimines. Facile Regio- and Stereo-specific Cycloaddition Reactions" Tetrahedron, 48(47): 10431-10442.

Johnstone, RA et al. (1985) "Heterogeneous Catalytic Transfer Hydrogenation and its Relation to Other Methods for Reduction of Organic Compounds" Chem Rev, 85:129-170.

Liu, T-L. et al. (2011) "Catalytic asymmetric 1,3-dipolar cycloaddition of N-unprotected2-oxoindolin-3-ylidene derivatives and azomethine ylides for the consu action of spirooxindole-pyrrolidines" Org Biomol Chem, 9:1980-1986.

Liu, J. et al. (2012) "Direct construction of novel exo'-selective spiropyrrolidine bisoxindoles via a three-component 1,3-dipolar cycloaddition reaction" Tetrahedron Letters, 53:2336-2340.

Liu, K. et al. (2007) "Highly Enantioselective Michael Addition of Aromatic Ketones to Nitroolefins Promoted by Chiral Bifunctional Primary Amine-Thiourea Catalysts Based on Saccharides" Organic Letters, 9(5):923-925, with "Supporting Information", 28 pages.

Noyori, R. et al. (2002) "Asymmetric Catalysis: Science and Opportunities (Nobel Lecture)" Angewandte Chemie Int Ed, 41:2008-2022.

Sebahar, P.R. and R.M. Williams (2000) "The Asymmetric Total Synthesis of (+)- and (−)-Spirotryprostatin B" J Am Chem Soc, 122:5666-5667.

Shi, F. et al. (2012) "Scaffold-Inspired Enantioselective Synthesis of Biologically Important Spiro[pyrrolidin-3,2'-oxindoles] with Structural Diversity through Catalytic Isatin-Derived 1,3-Dipolar Cycloadditions" Chem Eur J, 18:6885-6894.

Shu, L. et al. (2013) "Synthesis of a Spiroindolinone Pyrrolidinecarboxamide MDM2 Antagonist" Org Process Res Dev, 17:247-256.

Xu, Y. and A. Cordova (2006) "Simple highly modular acyclic amine-catalyzed direct enantioselective addition of ketones to nitroolefins" ChemComm, 2006:460-462.

\* cited by examiner

METHOD FOR PRODUCING A SPIROOXINDOLE DERIVATIVE

This application is a divisional application of U.S. application Ser. No. 16/031,165, filed Jul. 10, 2018, which is a divisional application of U.S. application Ser. No. 14/916,677, filed Mar. 4, 2016, now U.S. Pat. No. 10,030,028, entitled "Method for Producing a Spirooxindole Derivate," which is a national stage application under 35 U.S.C. 371 of International Application No. PCT/JP2014/073233, filed Sep. 3, 2014, entitled "Method for Producing Spirooxindole Derivative," which claims priority to Japanese Patent Application No. 2013-182928, filed Sep. 4, 2013.

TECHNICAL FIELD

The present invention relates to a method for producing a pyrrolidine compound having a spirooxindole structure.

BACKGROUND ART

A method which involves using, as a reaction substrate, aldimine synthesized from an aldehyde and an amine as starting materials to synthesize a racemic compound through a 1,3-dipolar cycloaddition reaction in the presence or absence of a catalyst that promotes the reaction is known as a method for synthesizing a pyrrolidine compound having a bicyclic spirooxindole structure (Non Patent References 1 to 4). The obtained racemic compound can be resolved using a chiral column based on a technique such as HPLC or supercritical fluid chromatography (SFC) to separate a desired optically active form.

An asymmetric synthesis method through a 1,3-dipolar cycloaddition reaction using a chiral element has been reported as a method for stereoselectively synthesizing the compound mentioned above (Non Patent References 5 and 6). In addition, a method for producing a pyrrolidine compound having a tricyclic dispirooxindole structure through a 1,3-dipolar addition reaction using, as a reaction substrate, ketimine synthesized with an amine and a ketone as starting materials has also been reported (Patent Reference 1).

Meanwhile, as for catalytic asymmetric synthesis methods of the compound mentioned above, a large number of studies have been made on catalytic asymmetric 1,3-dipolar cycloaddition reactions using aldimine as a reaction substrate (Non Patent References 7 to 18). Nonetheless, no report has been made on the synthesis of a tricyclic dispiroindole using ketimine with a ketone and an amine as reaction substrates.

CITATION LIST

Patent References

Patent Reference 1: WO2012/121361

Non Patent References

Non Patent Reference 1: Jorgensen, K. A. et al., Org. Lett. 2005, 21, 4569
Non Patent Reference 2: Jorgensen, K. A. et al., Chem. Rev. 1998, 98, 863
Non Patent Reference 3: Grigg, R. et al., Tetrahedron, 1992, 48, 10431
Non Patent Reference 4: Schreiber, S. L. et al., J. Am. Chem. Soc. 2003, 125, 10174
Non Patent Reference 5: Carretero, J. C. et al., Tetrahedron, 2007, 63, 6587
Non Patent Reference 6: Wang, S. et al., J. Am. Chem. Soc., 2005, 127, 10130
Non Patent Reference 7: Wang, S. et al., J. Med. Chem. 2006, 49, 3432
Non Patent Reference 8: Williams, R. M. et al., J. Am. Chem. Soc. 2000, 122, 5666
Non Patent Reference 9: Gong, L.-Z. et al., J. Am. Chem. Soc., 2009, 131, 13819
Non Patent Reference 10: Gong, L.-Z. et al., Org. Lett., 2011, 13, 2418
Non Patent Reference 11: Gong, L.-Z. et al., Chem. Eur. J., 2012, 18, 6885
Non Patent Reference 12: Waldmann, H. et al., Nat. Chem., 2010, 2, 735
Non Patent Reference 13: Waldmann, H. et al., Tetrahedron, 2011, 67, 10195
Non Patent Reference 14: Wang, C.-J. et al., Org. Biomol. Chem., 2011, 9, 1980
Non Patent Reference 15: Arai, T. et al., Chem. Eur. J., 2012, 18, 8287
Non Patent Reference 16: Amedohkouh, M. et al., Tetrahedron Asymmetry, 2005, 8, 1411
Non Patent Reference 17: Cordova, A. et al., Chem. Comm. 2006, 460
Non Patent Reference 18: Ma, J. A. et al., Org. Lett. 2007, 9, 923

SUMMARY OF INVENTION

Technical Problem

The present invention is intended to provide a method for efficiently producing and providing a compound having a spirooxindole skeleton, for example, a compound having a spirooxindole skeleton and having antitumor activity that inhibits the interaction between Mdm2 protein and p53 protein, or an intermediate thereof using an asymmetric catalyst.

Solution to Problem

The present inventors have conducted diligent studies and consequently established a method for efficiently synthesizing a compound having an optically active tricyclic dispiroindole skeleton by screening for a chiral ligand that promotes a catalytic asymmetric 1,3-dipolar cycloaddition reaction using ketimine as a reaction substrate, and a Lewis acid serving as a central metal thereof, and the optimum reaction conditions.

Specifically the present invention relates to the following (1) to (20):

(1) A Method for Reacting a Compound Represented by Formula (I):

[Formula 1]

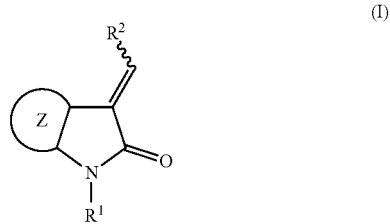

a compound represented by formula (II):

[Formula 2]

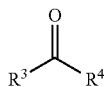
(II)

and a compound represented by formula (III):

[Formula 3]

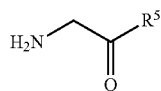
(III)

in a solvent using an asymmetric catalyst to stereoselectively produce a compound represented by formula (IV) or a salt thereof:

[Formula 4]

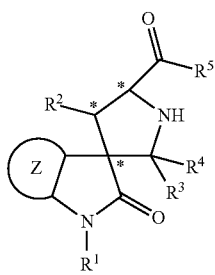
(IV)

wherein $R^1$ represents a hydrogen atom, a $C_1$-$C_6$ alkylcarbonyl group optionally having 1 to 3 substituents independently selected from group A below, or a $C_1$-$C_6$ alkoxycarbonyl group optionally having 1 to 3 substituents independently selected from group A below, $R^2$ represents a 5- or 6-membered heteroaryl group having, in the ring, 1 to 3 heteroatoms independently selected from the group consisting of a nitrogen atom, an oxygen atom and a sulfur atom, a phenyl group, a $C_3$-$C_6$ cycloalkyl group, or a $C_3$-$C_6$ cycloalkenyl group, wherein the 5- or 6-membered heteroaryl group, the phenyl group, the $C_3$-$C_6$ cycloalkyl group, and the $C_3$-$C_6$ cycloalkenyl group each optionally have 1 to 3 substituents independently selected from the group consisting of a halogen atom, a vinyl group, an ethynyl group, a cyano group, a hydroxy group, an amino group, a carboxy group, an aminocarbonyl group, a $C_1$-$C_6$ alkyl group optionally having 1 to 3 substituents independently selected from group A below, a $C_3$-$C_4$ cycloalkyl group optionally having 1 to 3 substituents independently selected from group A below, a $C_1$-$C_6$ alkoxy group optionally having 1 to 3 substituents independently selected from group A below, a $C_3$-$C_4$ cycloalkoxy group optionally having 1 to 3 substituents independently selected from group A below, a $C_1$-$C_6$ alkylamino group optionally having 1 to 3 substituents independently selected from group A below, a di-$C_1$-$C_6$ alkylamino group optionally having 1 to 3 substituents independently selected from group A below, a 4- to 7-membered saturated heterocyclic group containing one nitrogen atom in the ring and optionally having 1 to 3 substituents independently selected from group B below, a $C_1$-$C_6$ alkoxycarbonyl group optionally having 1 to 3 substituents independently selected from group A below, a $C_3$-$C_4$ cycloalkoxycarbonyl group optionally having 1 to 3 substituents independently selected from group A below, a $C_1$-$C_6$ alkylaminocarbonyl group optionally having 1 to 3 substituents independently selected from group A below, and a $C_3$-$C_4$ cycloalkylaminocarbonyl group optionally having 1 to 3 substituents independently selected from group A below, $R^3$ and $R^4$ each independently represent a $C_1$-$C_6$ alkyl group optionally having 1 to 3 substituents independently selected from group C below, or $R^3$ and $R^4$ optionally together form a $C_4$-$C_6$ cycloalkyl ring, a tetrahydrofuran ring, a tetrahydropyran ring, or a piperidine ring, wherein the $C_4$-$C_6$ cycloalkyl ring, the tetrahydrofuran ring, the tetrahydropyran ring, and the piperidine ring each optionally have 1 to 8 substituents independently selected from group D below, $R^5$ represents a $C_1$-$C_6$ alkoxy group optionally having 1 to 3 substituents independently selected from group E below, a $C_3$-$C_8$ cycloalkoxy group optionally having 1 to 3 substituents independently selected from group E below, a $C_2$-$C_6$ alkenyloxy group, or —$NR^{51}R^{52}$, $R^{51}$ and $R^{52}$ each independently represent a hydrogen atom, a $C_1$-$C_6$ alkyl group optionally having 1 to 3 substituents independently selected from group E below, a $C_3$-$C_8$ cycloalkyl group optionally having 1 to 3 substituents independently selected from group E below, or a 3- to 6-membered saturated heterocyclic group having, in the ring, one heteroatom independently selected from the group consisting of a nitrogen atom, an oxygen atom and a sulfur atom and optionally having 1 to 3 substituents independently selected from group E below, and ring Z represents a benzene ring optionally having 1 to 4 substituents independently selected from group E below, a pyridine ring optionally having 1 to 3 substituents independently selected from group E below, or a pyrimidine ring optionally having 1 or 2 substituents independently selected from group E below:

group A: a halogen atom, a hydroxy group, a $C_1$-$C_6$ alkyl group, an amino group, and a phenyl group, group B: a $C_1$-$C_6$ alkyl group and a hydroxy group group C: a halogen atom, a hydroxy group, a phenyl group, a pyridyl group, and an amino group group D: a halogen atom and a $C_1$-$C_6$ alkyl group optionally having 1 to 3 halogen atoms, and group E: a halogen atom, a hydroxy group, a vinyl group, an ethynyl group, a cyano group, a $C_1$-$C_6$ alkoxy group, an aminocarbonyl group, and a $C_1$-$C_6$ alkyl group optionally having 1 to 3 halogen atoms.

(2) A method for reacting a compound represented by formula (I):

[Formula 5]

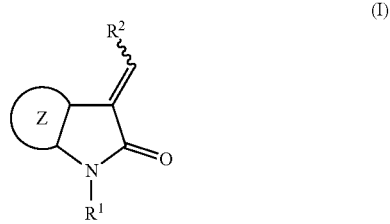
(I)

and a compound represented by formula (V):

[Formula 6]

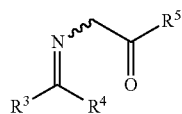
(V)

in a solvent using an asymmetric catalyst to stereoselectively produce a compound represented by formula (IV) or a salt thereof:

[Formula 7]

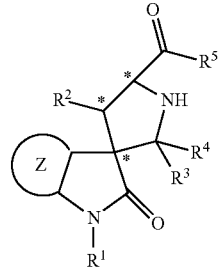
(IV)

wherein $R^1$, $R^2$, $R^3$, $R^4$, $R^5$, and Z are as defined in (1).

(3) A method according to (1) or (2), wherein the asymmetric catalyst is a catalyst prepared from a Lewis acid and a chiral ligand, wherein the Lewis acid is a Lewis acid selected from the group consisting of a Zn(II) Lewis acid, a Ag(I) Lewis acid, a Ni(II) Lewis acid, a Co(II) Lewis acid, a Ru(I) Lewis acid, a Cu(I) Lewis acid, and a Cu(II) Lewis acid, and the chiral ligand is a chiral ligand selected from the group consisting of a compound represented by the following formula (VI):

[Formula 8]

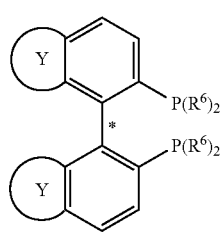
(VI)

a compound represented by the following formula (VII):

[Formula 9]

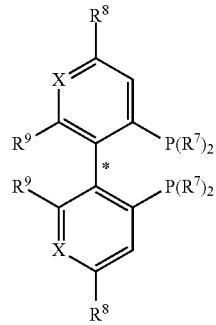
(VII)

a compound represented by the following formula (VIII):

[Formula 10]

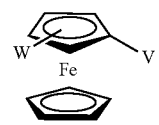
(VIII)

a compound represented by the following formula (IX):

[Formula 11]

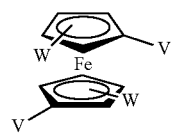
(IX)

a compound represented by the following formula (X):

[Formula 12]

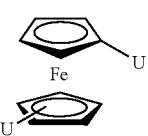
(X)

a compound represented by the following formula (XI):

[Formula 13]

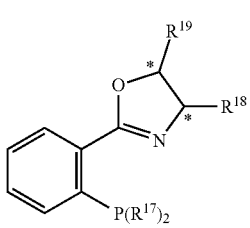
(XI)

and a compound represented by the following formula (XII):

[Formula 14]

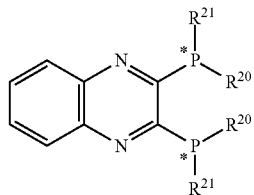
(XII)

wherein
R[6] represents a phenyl group optionally having 1 to 3 substituents independently selected from group F below,
ring Y represents a benzene ring, a cyclohexane ring, or a dioxolane ring optionally having 1 to 4 halogen atoms,
R[7] represents a phenyl group optionally having 1 to 3 substituents independently selected from group G below, or a furanyl group optionally having 1 to 3 substituents independently selected from group G below,
R[8] represents a hydrogen atom or a $C_1$-$C_6$ alkoxy group,
R[9] represents a $C_1$-$C_6$ alkoxy group, or
two R[9] moieties optionally together form a 7- to 12-membered heterocyclic ring containing two oxygen atoms in the ring,
X represents CH, CR[10], or a nitrogen atom, wherein
R[10] represents a $C_1$-$C_6$ alkoxy group,
V represents a phenyl group having one P(R[11])$_2$ or PH(O)R[12], wherein
R[11] represents a $C_1$-$C_6$ alkyl group, a cyclohexyl group, or a phenyl group optionally having two trifluoromethyl groups, and
R[12] represents a $C_1$-$C_6$ alkyl group or a phenyl group, W represents a $C_1$-$C_6$ alkylthio group, a dihydrooxazolyl group optionally having one $C_1$-$C_6$ alkyl group, CH(CH$_3$)P(R[13])$_2$, or CHR[14]R[15], wherein
R[13] represents a cyclohexyl group, a $C_1$-$C_6$ alkyl group, or a phenyl group optionally having 1 or 2 substituents independently selected from group H below,
R[14] represents a phenyl group optionally substituted by one P(R[16])$_2$,
R[15] represents a $C_1$-$C_6$ alkyl group or a di-$C_1$-$C_6$ alkylamino group, and
R[16] represents a phenyl group or a cyclohexyl group,
U represents any one of the following U[a] to U[d]:

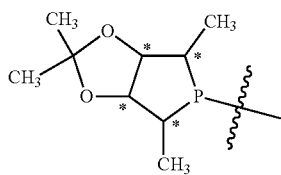
U[a]

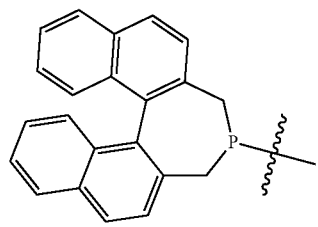
U[b]

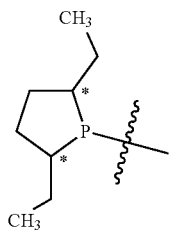
U[c]

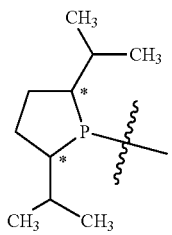
U[d]

R[17] represents a phenyl group optionally having 1 to 3 substituents independently selected from group F below,
R[18] represents a $C_1$-$C_6$ alkyl group or a phenyl group,
R[19] represents a hydrogen atom or a $C_1$-$C_6$ alkyl group, and
R[20] and R[21] each independently represent a $C_1$-$C_6$ alkyl group:
group F: a $C_1$-$C_6$ alkyl group and a $C_1$-$C_6$ alkoxy group,
group G: a $C_1$-$C_6$ alkyl group, a $C_1$-$C_6$ alkoxy group, and a di-$C_1$-$C_6$ alkylamino group, and
group H: a $C_1$-$C_6$ alkyl group and a $C_1$-$C_6$ alkyl group optionally having three halogen atoms.

(4) A method according to any one of (1) to (3), wherein the Lewis acid used in the preparation of the asymmetric catalyst is a Cu(I) Lewis acid or a Cu(II) Lewis acid.

(5) A method according to any one of (1) to (4), wherein the Lewis acid used in the preparation of the asymmetric catalyst is a Lewis acid selected from the group consisting of CuOAc, CuCl, CuBr, CuI, CuOTf, CuPF$_6$, CuBF$_4$, Cu(OAc)$_2$, Cu(OTf)$_2$, and CuSO$_4$.

(6) A method according to any one of (1) to (5), wherein the chiral ligand used in the preparation of the asymmetric catalyst is a chiral ligand selected from the group consisting of a compound represented by formula (V), a compound represented by formula (VI), a compound represented by formula (VII), a compound represented by formula (VIII), a compound represented by formula (IX), a compound represented by formula (X), and a compound represented by formula (XI),
wherein
R[6] represents a phenyl group optionally having 1 to 3 substituents independently selected from the group consisting of a methyl group, a t-butyl group, and a methoxy group,
ring Y represents a benzene ring, a cyclohexane ring, or a dioxolane ring,
R[7] represents a phenyl group or a furanyl group, wherein the phenyl group and the furanyl group each optionally have 1 to 3 substituents independently selected from the group consisting of a methyl group, a t-butyl group, and a methoxy group,
R[8] represents a hydrogen atom or a methoxy group,
R[9] represents a methoxy group, or,
two R[9] moieties optionally together form a 9-membered heterocyclic ring containing two oxygen atoms in the ring,
X represents CH, CR[10], or a nitrogen atom, R[10] represents a methoxy group, V represents P(R[11])₂, wherein R[11] represents a phenyl group optionally having two trifluoromethyl groups, W represents a t-butylthio group, a dihydrooxazolyl group optionally substituted by one isopropyl group, or CH(CH₃)P(R[13])₂, wherein R[13] represents a phenyl group optionally having 1 or 2 methyl groups, U represents $U^a$ or $U^d$ mentioned above, R[17] represents a phenyl group, R[18] represents an isopropyl group, a t-butyl group, or a phenyl group, R[19] represents a hydrogen atom, and R[20] and R[21] each independently represent a methyl group or a t-butyl group.

(7) A method according to any one of (1) to (6), wherein the chiral ligand used in the preparation of the asymmetric catalyst is a chiral ligand selected from the following group:

[Formula 16]

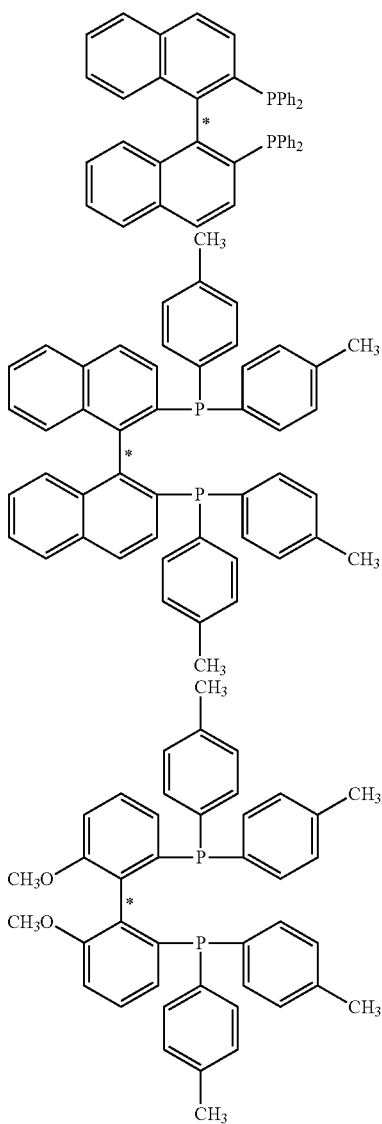

[Formula 17]

-continued

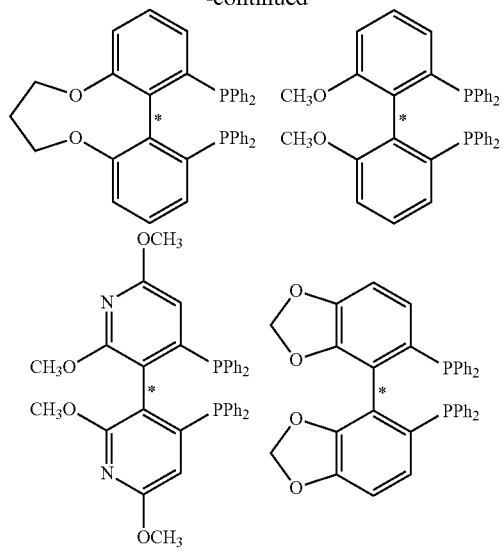

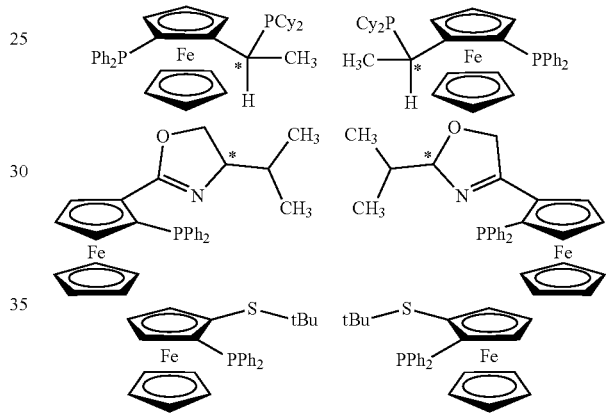

(8) A method according to any one of (1) to (7), wherein the solvent used in the reaction is one or more solvents selected from the group consisting of N,N-dimethylacetamide, tetrahydrofuran, dimethoxyethane, 2-propanol, toluene, and ethyl acetate.

(9) A method according to any one of (1) to (8), wherein the compound produced or salt thereof has the following configuration:

[Formula 18]

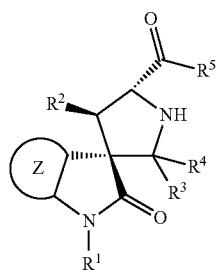

(XIII)

wherein R¹, R², R³, R⁴, R⁵, and Z are as defined in (1).

(10) A method according to any one of (1) to (9), wherein R₁ is a hydrogen atom.

(11) A method according to any one of (1) to (10), wherein in formula (I), ring Z is a benzene ring optionally having 1 to 4 halogen atoms.

(12) A method according to any one of (1) to (11), wherein in formula (I) or formula (IV), $R^2$ is a pyridyl group optionally having 1 to 3 halogen atoms, or a phenyl group optionally having 1 to 3 halogen atoms.

(13) A method according to any one of (1) to (12), wherein in formula (II) or formula (V), $R^3$ and $R^4$ each represent a methyl group, or $R^3$ and $R^4$ together form a cyclopentane ring, a cyclohexane ring, or a tetrahydropyran ring, wherein the cyclopentane ring, the cyclohexane ring, and the tetrahydropyran ring each optionally have 1 to 4 $C_1$-$C_6$ alkyl groups on the ring.

(14) A method according to any one of (1) to (13), wherein in formula (III) or formula (V), $R^5$ is a substituent represented by the following:

[Formula 19]

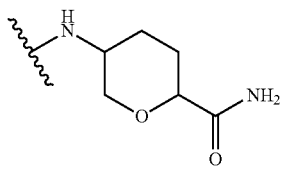

(15) A method according to any one of (1) to (13), wherein in formula (III) or formula (V), $R^5$ is a $C_1$-$C_6$ alkoxy group.

(16) A method for hydrolyzing a compound or a salt thereof produced using a method according to (15) to produce a compound represented by the following formula (XIV) or a salt thereof:

[Formula 20]

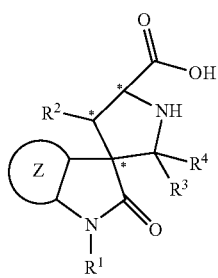

(XIV)

and condensing the compound or the salt with a compound represented by $NHR^{22}R^{23}$ to produce a compound represented by the following formula (XV) or a salt thereof:

[Formula 21]

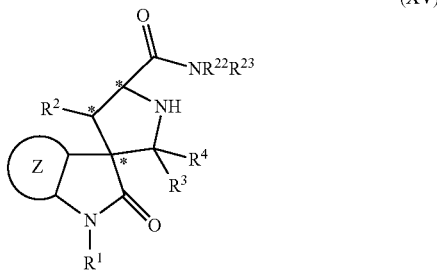

(XV)

wherein $R^1$, $R^2$, $R^3$, $R^4$, and Z are as defined in any one of (1) to (13), and $R^{22}$ and $R^{23}$ each independently represent a hydrogen atom, a $C_1$-$C_6$ alkyl group optionally having 1 to 3 substituents independently selected from group I below, a $C_1$-$C_6$ alkylsulfonyl group optionally having 1 to 3 substituents independently selected from group I below, a $C_3$-$C_6$ cycloalkyl group optionally having 1 to 3 substituents independently selected from group I below, a 3- to 6-membered saturated heterocyclic group having, in the ring, one heteroatom independently selected from the group consisting of a nitrogen atom, an oxygen atom and a sulfur atom and optionally having 1 to 3 substituents independently selected from group I below, a phenyl group optionally having 1 to 3 substituents independently selected from group I below, or a 5- or 6-membered heteroaryl group having, in the ring, 1 to 3 heteroatoms independently selected from the group consisting of a nitrogen atom, an oxygen atom and a sulfur atom and optionally having 1 to 3 substituents independently selected from group I below, or $R^{22}$ and $R^{23}$ optionally together form a piperazine ring optionally having 1 to 3 substituents independently selected from group I below:

group I: a halogen atom, a hydroxy group, an oxo group, a carboxy group, a formyl group, an amino group, an aminocarbonyl group, a cyano group, a $C_1$-$C_6$ alkylamino group, a $C_1$-$C_6$ alkylsulfonyl group, a $C_1$-$C_6$ alkylsulfonylamide group, a $C_1$-$C_6$ alkyl group optionally having 1 to 3 substituents independently selected from group J below, a $C_1$-$C_6$ alkoxy group optionally having 1 to 3 substituents independently selected from group J below, a $C_1$-$C_6$ alkylcarbonyl group optionally having 1 to 3 substituents independently selected from group J below, a $C_3$-$C_6$ cycloalkylcarbonyl group optionally having 1 to 3 substituents independently selected from group J below, a $C_4$-$C_6$ cycloalkyl group optionally having 1 to 3 substituents independently selected from group J below, a $C_1$-$C_6$ alkoxycarbonyl group optionally having 1 to 3 substituents independently selected from group J below, a piperidinyl group optionally having 1 to 3 substituents independently selected from group J below, a pyrrolidinyl group optionally having 1 to 3 substituents independently selected from group J below, a piperazinyl group optionally having 1 to 3 substituents independently selected from group J below, a phenyl group optionally having 1 to 3 substituents independently selected from group J below, a tetrazolyl group, an azetidinyl group optionally having 1 to 3 substituents independently selected from group J below, a morpholino group optionally having 1 to 3 substituents independently selected from group J below, a dihydropyrazolyl group optionally having 1 to 3 substituents independently selected from group J below, and an oxadiazolyl group, and group J: a halogen atom, a hydroxy group, an amino group, a carboxy group, an aminocarbonyl group, a phenyl group, a $C_1$-$C_6$ alkyl group, a $C_1$-$C_6$ alkylamino group, a di-$C_1$-$C_6$ alkylamino group, a $C_1$-$C_6$ alkylcarbonyl group, a $C_3$-$C_6$ cycloalkyl group, a $C_1$-$C_6$ alkylsulfonyl group, and a $C_1$-$C_6$ alkylsulfonylamide group.

(17) A method according to (16), wherein $R^{22}$ represents a hydrogen atom, and $R^{23}$ is a substituent represented by the following:

[Formula 22]

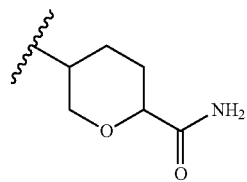

(18) A method for reacting a compound represented by formula (XVI):

[Formula 23]

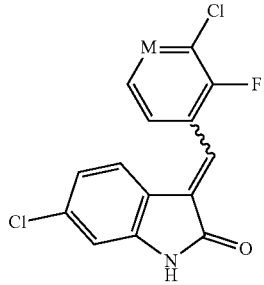

(XVI)

a compound represented by formula (XVII):

[Formula 24]

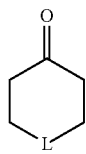

(XVII)

and a compound represented by formula (XVIII):

[Formula 25]

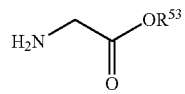

(XVIII)

in a solvent using an asymmetric catalyst prepared from a Lewis acid selected from the group consisting of a Cu(I) Lewis acid and a Cu(II) Lewis acid and a chiral ligand selected from the following group:

[Formula 26]

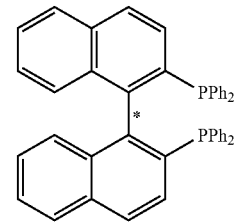

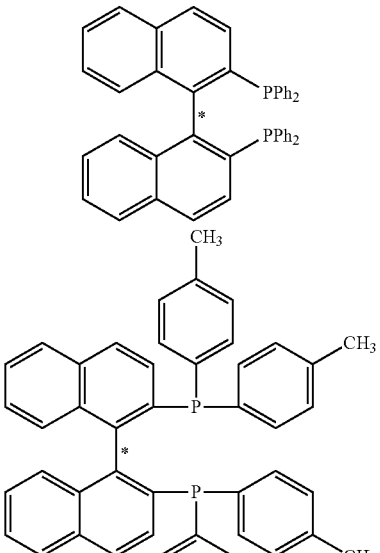

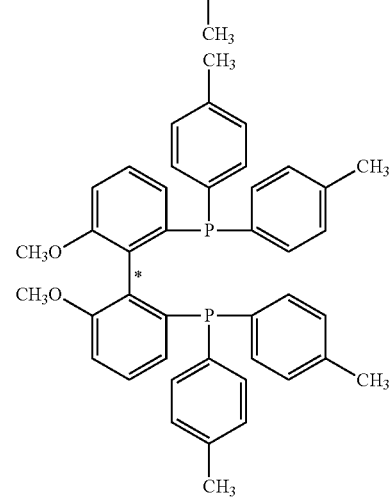

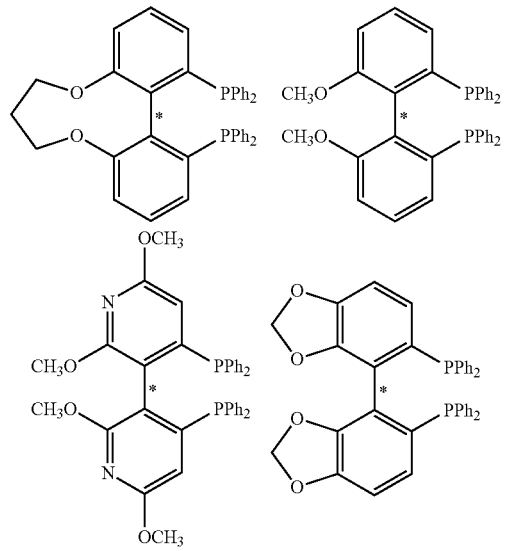

-continued

[Formula 27]

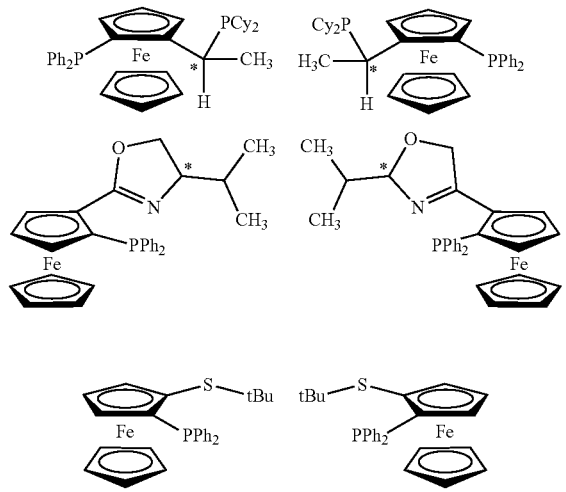

to stereoselectively produce a compound represented by formula (XIX) or a salt thereof:

[Formula 28]

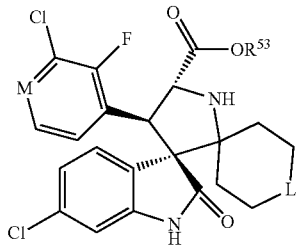

wherein

M represents a nitrogen atom or CH,

L represents a single bond, an oxygen atom, $CH_2$, or $C(CH_3)_2$, and $R^{53}$ represents a $C_1$-$C_6$ alkyl group.

(19) A method for reacting a compound represented by formula (XVI):

[Formula 29]

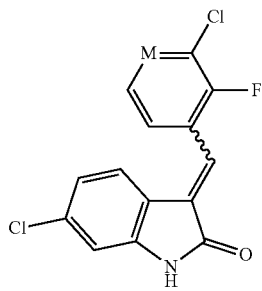

and a compound represented by formula (XX):

[Formula 30]

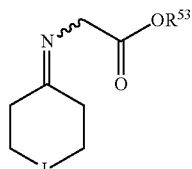

in a solvent using an asymmetric catalyst prepared from a Lewis acid selected from the group consisting of a Cu(I) Lewis acid and a Cu(II) Lewis acid and a chiral ligand selected from the following group:

[Formula 31]

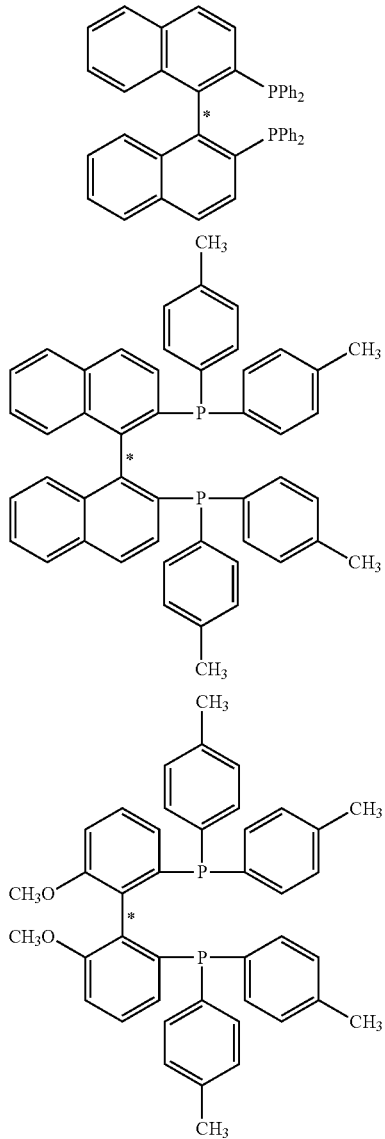

-continued

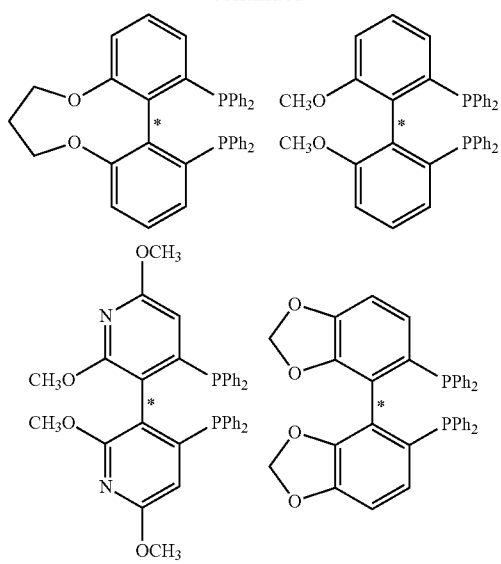

[Formula 32]

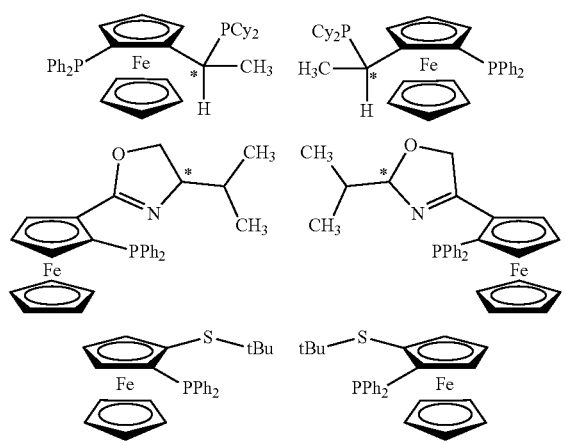

to stereoselectively produce a compound represented by formula (XIX) or a salt thereof:

[Formula 33]

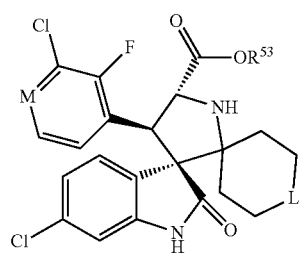

(XIX)

wherein
M, L, and $R^{53}$ are as defined in 18.

(20) A method for hydrolyzing a compound or a salt thereof produced using a method according to (18) or (19) to produce a compound represented by the following formula (XXI) or a salt thereof:

[Formula 34]

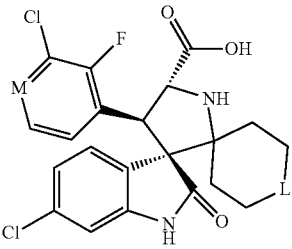

(XXI)

and condensing the compound or the salt with a compound represented by the following formula:

[Formula 35]

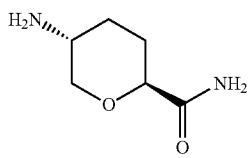

to produce a compound represented by the following formula (XXII) or a salt thereof:

[Formula 36]

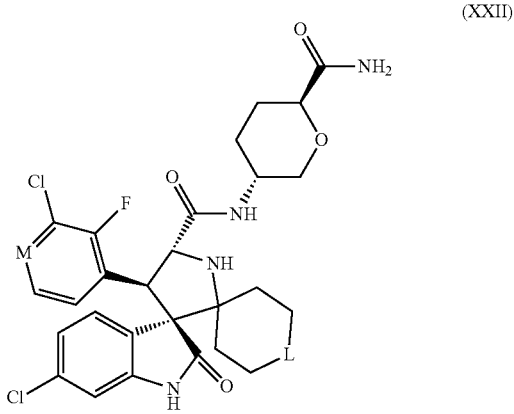

(XXII)

wherein
M and L are as defined in (18) or (19).

Advantageous Effects of Invention

According to the present invention, a compound having a spirooxindole skeleton, for example, a compound having a spirooxindole skeleton and having antitumor activity that inhibits the interaction between Mdm2 protein and p53 protein can be stereoselectively synthesized in an efficient and inexpensive manner.

DESCRIPTION OF EMBODIMENTS

In the present invention, a "halogen atom" is a fluorine atom, a chlorine atom, a bromine atom, or an iodine atom.
In the present invention, a "$C_1$-$C_6$ alkyl group" refers to a linear or branched alkyl group having 1 to 6 carbon atoms and is a methyl group, an ethyl group, a propyl group, an isopropyl group, a butyl group, an isobutyl group, a s-butyl group, a t-butyl group, a pentyl group, an isopentyl group, a 2-methylbutyl group, a neopentyl group, a 1-ethylpropyl group, a hexyl group, an isohexyl group, or a 4-methylpentyl group.

In the present invention, a "$C_3$-$C_6$ cycloalkyl group" is a cyclopropyl group, a cyclobutyl group, a cyclopentyl group, or a cyclohexyl group.

In the present invention, a "$C_3$-$C_4$ cycloalkyl group" is a cyclopropyl group or a cyclobutyl group.

In the present invention, a "$C_1$-$C_6$ alkoxy group" refers to a group in which a $C_1$-$C_6$ alkyl group mentioned above is substituted by an oxy group, and is a methoxy group, an ethoxy group, a propoxy group, an isopropoxy group, a butoxy group, an isobutoxy group, a s-butoxy group, a t-butoxy group, a pentoxy group, an isopentoxy group, a 2-methylbutoxy group, a hexyloxy group, or an isohexyloxy group.

In the present invention, a "$C_3$-$C_6$ cycloalkoxy group" refers to a group in which a $C_3$-$C_6$ cycloalkyl group mentioned above is substituted by an oxy group, and is a cyclopropoxy group, a cyclobutoxy group, a cyclopentyloxy group, or a cyclohexyloxy group.

In the present invention, a "$C_3$-$C_4$ cycloalkoxy group" is a cyclopropoxy group or a cyclobutoxy group.

In the present invention, a "$C_3$-$C_8$ cycloalkoxy group" is a cyclopropoxy group, a cyclobutoxy group, a cyclopentyloxy group, a cyclohexyloxy group, a cycloheptyloxy group, or a cyclooctyloxy group.

In the present invention, a "$C_1$-$C_6$ alkylthio group" refers to a group in which a $C_1$-$C_6$ alkyl group mentioned above is substituted by a thio group. Examples thereof include a methylthio group, an ethylthio group, a propylthio group, and an isopropylthio group.

In the present invention, a "$C_1$-$C_6$ alkylsulfonyl group" refers to a group in which a $C_1$-$C_6$ alkyl group mentioned above is substituted by a sulfonyl group. Examples thereof include a methylsulfonyl group, an ethylsulfonyl group, a propylsulfonyl group, and an isopropylsulfonyl group.

In the present invention, a "$C_1$-$C_6$ alkylsulfonylamide group" refers to a group in which a $C_1$-$C_6$ alkylsulfonyl group mentioned above is substituted by an amino group. Examples thereof include a methylsulfonylamide group, an ethylsulfonylamide group, a propylsulfonylamide group, and an isopropylsulfonylamide group.

In the present invention, a "$C_1$-$C_6$ alkylcarbonyl group" refers to a group in which a $C_1$-$C_6$ alkyl group mentioned above is substituted by a carbonyl group. Examples thereof include an acetyl group, an ethylcarbonyl group, a propylcarbonyl group, and an isopropylcarbonyl group.

In the present invention, a "$C_1$-$C_6$ alkoxycarbonyl group" refers to a group in which a $C_1$-$C_6$ alkoxy group mentioned above is substituted by a carbonyl group. Examples thereof include a methoxycarbonyl group, an ethoxycarbonyl group, a propoxycarbonyl group, and an isopropoxycarbonyl group.

In the present invention, a "$C_3$-$C_6$ cycloalkylcarbonyl group" refers to a group in which a $C_3$-$C_6$ cycloalkyl group mentioned above is substituted by a carbonyl group, and is a cyclopropylcarbonyl group, a cyclobutylcarbonyl group, a cyclopentylcarbonyl group, or a cyclohexylcarbonyl group.

In the present invention, a "$C_3$-$C_6$ cycloalkoxycarbonyl group" refers to a group in which a $C_3$-$C_6$ cycloalkoxy group mentioned above is substituted by a carbonyl group, and is a cyclopropoxycarbonyl group, a cyclobutoxycarbonyl group, a cyclopentyloxycarbonyl group, or a cyclohexyloxycarbonyl group.

In the present invention, a "$C_1$-$C_6$ alkylamino group" refers to a group in which a $C_1$-$C_6$ alkyl group mentioned above is substituted by an amino group. Examples thereof include a methylamino group, an ethylamino group, a propylamino group, and an isopropylamino group.

In the present invention, a "di-$C_1$-$C_6$ alkylamino group" refers to a group in which two identical or different $C_1$-$C_6$ alkyl groups mentioned above are substituted by an amino group. Examples thereof include a dimethylamino group, a diethylamino group, a dipropylamino group, and a diisopropylamino group.

In the present invention, a "$C_1$-$C_6$ alkylaminocarbonyl group" refers to a group in which a $C_1$-$C_6$ alkylamino group mentioned above is substituted by a carbonyl group. Examples thereof include a methylaminocarbonyl group, an ethylaminocarbonyl group, a propylaminocarbonyl group, and an isopropylaminocarbonyl group.

In the present invention, a "$C_3$-$C_6$ cycloalkylaminocarbonyl group" refers to a group in which a $C_3$-$C_6$ cycloalkyl group mentioned above is bonded to the amino group side of a (—NH—C(=O)—) group, and is a cyclopropylaminocarbonyl group, a cyclobutylaminocarbonyl group, a cyclopentylaminocarbonyl group, or a cyclohexylaminocarbonyl group.

In the present invention, a "$C_3$-$C_8$ cycloalkylamino group" refers to a group in which a $C_3$-$C_8$ cycloalkyl group mentioned above is bonded to an amino group, and is a cyclopropylamino group, a cyclobutylamino group, or a cyclopentylamino group.

In the present invention, a "$C_2$-$C_6$ alkenyloxy group" refers to a group in which a linear or branched $C_2$-$C_6$ alkenyl group having 2 to 6 carbon atoms is bonded to an oxy group. Examples thereof include a vinyloxy group, an allyloxy group, and an isopropenyloxy group.

In the present invention, a "$C_3$-$C_6$ cycloalkenyl group" is a cyclopropenyl group, a cyclobutenyl group, a cyclopentenyl group, or a cyclohexenyl group.

In the present invention, a "5- or 6-membered heteroaryl group" refers to a group derived from a 5- or 6-membered monocyclic aromatic compound containing 1 to 3 atoms each independently selected from the group consisting of a nitrogen atom, an oxygen atom and a sulfur atom in addition to carbon as atoms constituting the ring. Examples thereof include a furyl group, a thienyl group, a pyrrolyl group, an oxazolyl group, an isoxazolyl group, a thiazolyl group, an isothiazolyl group, an imidazolyl group, a pyrazolyl group, a pyridyl group, a pyrazinyl group, a pyrimidinyl group, and a pyridazinyl group.

In the present invention, a "3- to 6-membered saturated heterocyclic group" refers to a group derived from a 3- to 6-membered monocyclic saturated heterocyclic compound containing one atom selected from the group consisting of a nitrogen atom, an oxygen atom and a sulfur atom in addition to carbon as atoms constituting the ring. Examples thereof include an aziridinyl group, an oxiranyl group, a thiiranyl group, an azetidinyl group, an oxetanyl group, a thietanyl group, a pyrrolidinyl group, a tetrahydrofuranyl group, a tetrahydrothienyl group, a piperidinyl group, a tetrahydropyranyl group, and a tetrahydrothiopyranyl group.

In the present invention, an "asymmetric catalyst" refers to a catalyst for use in asymmetric synthesis. Examples thereof include catalysts having a metal atom therein.

In the present invention, a "Lewis acid" refers to a substance capable of accepting an electron pair. Examples thereof include Zn(OTf)₂, AgOAc, Cu(OTf)₂, CuOAc, Ni(OAc)₂, Co(OAc)₂, CuCl, CuBr, CuI, CuPF₆, CuBF₄, Cu(OAc)₂, Cu(OTf)₂, and CuSO₄.

In the present invention, a "chiral ligand" refers to a substance having asymmetry and capable of forming a coordinate bond with a metal and includes not only unidentate ligands but multidentate ligands. Examples thereof include BINAP derivatives, MeBIPHEP derivatives, TunePHOS derivatives, P-Phos derivatives, JOSIPHOS derivatives, Walphos derivatives, FESULPHOS derivatives, Taniaphos derivatives, Jospophos derivatives, FOXAP derivatives, Mandyphos derivatives, Ferrocelane derivatives, PHOX derivatives, and QuinoxP derivatives.

In the present invention, the phrase "having asymmetry" means having an asymmetric center, axial chirality, or planar chirality.

In the present invention, the symbol "*" means an asymmetric center or axial chirality.

In the present invention, the symbol "Cy" is an abbreviation of a cyclopentyl group.

In the present invention, a "ketimine" refers to an imine formed from a ketone and an amine and is a compound having a structure in which the carbonyl group of the ketone is substituted by the nitrogen atom of the amine.

A compound represented by formula (I), a compound represented by formula (II), a compound represented by formula (III), a compound represented by formula (IV) or a salt thereof, a compound represented by formula (V), a compound represented by formula (VI), a compound represented by formula (VII), a compound represented by formula (VIII), a compound represented by formula (IX), a compound represented by formula (X), a compound represented by formula (XI), a compound represented by formula (XII), a compound represented by formula (XIII) or a salt thereof, a compound represented by formula (XIV) or a salt thereof, a compound represented by formula (XV) or a salt thereof, a compound represented by formula (XVI), a compound represented by formula (XVII), a compound represented by formula (XVIII), a compound represented by formula (XIX) or a salt thereof, a compound represented by formula (XX), a compound represented by formula (XXI) or a salt thereof, and a compound represented by formula (XXII) or a salt thereof according to the present invention encompass all isomers (diastereomers, optical isomers, geometric isomers, rotational isomers, etc.)

In the compound represented by formula (I), the compound represented by formula (II), the compound represented by formula (III), the compound represented by formula (IV) or a salt thereof, the compound represented by formula (V), the compound represented by formula (VI), the compound represented by formula (VII), the compound represented by formula (VIII), the compound represented by formula (IX), the compound represented by formula (X), the compound represented by formula (XI), the compound represented by formula (XII), the compound represented by formula (XIII) or a salt thereof, the compound represented by formula (XIV) or a salt thereof, the compound represented by formula (XV) or a salt thereof, the compound represented by formula (XVI), the compound represented by formula (XVII), the compound represented by formula (XVIII), the compound represented by formula (XIX) or a salt thereof, the compound represented by formula (XX), the compound represented by general formula (XXI) or a salt thereof, and the compound represented by formula (XXII) or a salt thereof, their isomers and mixtures of these isomers are all represented by single formulae. Thus, the present invention includes all of these isomers and mixtures of these isomers in arbitrary ratios.

A compound represented by formula (IV), a compound represented by formula (XIII), a compound represented by formula (XIV), a compound represented by formula (XV), a compound represented by formula (XIX), a compound represented by formula (XXI), and a compound represented by formula (XXII) according to the present invention may each be converted into a salt through its reaction with an acid when having a basic group or through its reaction with a base when having an acidic group.

Examples of a salt based on a basic group can include: hydrohalides such as hydrofluoride, hydrochloride, hydrobromide, and hydroiodide; inorganic acid salts such as nitrate, perchlorate, sulfate, and phosphate; $C_1$-$C_6$ alkylsulfonates such as methanesulfonate, trifluoromethanesulfonate, and ethanesulfonate; arylsulfonates such as benzenesulfonate and p-toluenesulfonate; and carboxylates such as acetate, oxalate, tartrate, and maleate.

On the other hand, examples of a salt based on an acidic group can include: alkali metal salts such as sodium salt, potassium salt, and lithium salt; alkaline earth metal salts such as calcium salt and magnesium salt; metal salts such as aluminum salt and iron salt; inorganic salts such as ammonium salt; amine salts of organic salts, etc., such as t-octylamine salt, dibenzylamine salt, morpholine salt, glucosamine salt, phenylglycine alkyl ester salt, ethylenediamine salt, N-methylglucamine salt, guanidine salt, diethylamine salt, triethylamine salt, dicyclohexylamine salt, N,N'-dibenzylethylenediamine salt, chloroprocaine salt, procaine salt, diethanolamine salt, N-benzylphenethylamine salt, piperazine salt, tetramethylammonium salt, and tris(hydroxymethyl)aminomethane salt; and amino acid salts such as glycine salt, lysine salt, arginine salt, ornithine salt, glutamate, and aspartate.

A compound represented by formula (IV) or a salt thereof, a compound represented by formula (XIII) or a salt thereof, a compound represented by formula (XIV) or a salt thereof, a compound represented by formula (XV) or a salt thereof, a compound represented by formula (XIX) or a salt thereof, a compound represented by formula (XXI) or a salt thereof, and a compound represented by formula (XXII) or a salt thereof according to the present invention, when left in air or recrystallized, may each incorporate a water molecule to form a hydrate. Such a hydrate is also included in a salt of the present invention.

A compound represented by formula (IV) or a salt thereof, a compound represented by formula (XIII) or a salt thereof, a compound represented by formula (XIV) or a salt thereof, a compound represented by formula (XV) or a salt thereof, a compound represented by formula (XIX) or a salt thereof, a compound represented by formula (XXI) or a salt thereof, and a compound represented by formula (XXII) or a salt thereof according to the present invention, when left in a solvent or recrystallized, may each absorb a certain kind of solvent to form a solvate. Such a solvate is also included in a salt of the present invention.

Examples of a solvent include: ether solvents such as tetrahydrofuran and 1,2-dimethoxyethane; alcohol solvents such as methanol, ethanol, and 2-propanol; hydrocarbon solvents such as toluene; nitrile solvents such as acetonitrile; aliphatic ester solvents such as ethyl acetate; and amide solvents such as N,N-dimethylacetamide and N,N-dimethylformamide.

Next, preferred embodiments of the present invention will be described.

Preferred forms of each substituent in a compound represented by formula (I), a compound represented by formula (II), a compound represented by formula (III), a compound represented by formula (IV), a compound represented by formula (V), a compound represented by formula (XIII), a compound represented by formula (XIV), and a compound represented by formula (XV) are given below.

$R^1$ represents a hydrogen atom, a $C_1$-$C_6$ alkylcarbonyl group, or a $C_1$-$C_6$ alkoxycarbonyl group optionally having one phenyl group. $R^1$ is more preferably a hydrogen atom, an acetyl group, a t-butoxycarbonyl group, or a benzyloxycarbonyl group, further preferably a hydrogen atom.

$R^2$ represents a 5- or 6-membered heteroaryl group having, in the ring, 1 to 3 heteroatoms independently selected from the group consisting of a nitrogen atom, an oxygen atom and a sulfur atom, or a phenyl group, wherein the 5- or 6-membered heteroaryl group and the phenyl group each optionally have 1 to 3 substituents independently selected from the group consisting of a halogen atom, a hydroxy group, an amino group, an aminocarbonyl group, and a $C_1$-$C_6$ alkyl group.

$R^2$ is more preferably a phenyl group optionally having 1 to 3 halogen atoms, or a pyridyl group optionally having 1 to 3 halogen atoms, even more preferably a phenyl group having one fluorine atom and one chlorine atom, or a pyridyl group having one fluorine atom and one chlorine atom.

Ring Z is a benzene ring optionally having 1 to 4 halogen atoms and is more preferably a benzene ring having one chlorine atom.

$R^3$ and $R^4$ each independently represent a $C_1$-$C_6$ alkyl group optionally having 1 to 3 substituents independently selected from the group consisting of a halogen atom, a hydroxy group, and an amino group. Both $R^3$ and $R^4$ are more preferably the same $C_1$-$C_6$ alkyl groups, even more preferably methyl groups.

In another form of $R^3$ and $R^4$, preferably, $R^3$ and $R^4$ together form a $C_4$-$C_6$ cycloalkyl ring optionally having 1 to 3 $C_1$-$C_6$ alkyl groups on the ring, a piperidine ring optionally having 1 to 3 $C_1$-$C_6$ alkyl groups on the ring, or a tetrahydropyran ring optionally having 1 to 3 $C_1$-$C_6$ alkyl groups on the ring. The ring formed is more preferably a cyclopentane ring optionally having 1 to 3 $C_1$-$C_6$ alkyl groups on the ring, a cyclohexane ring optionally having 1 to 3 $C_1$-$C_6$ alkyl groups on the ring, or a tetrahydropyran ring optionally having 1 to 3 $C_1$-$C_6$ alkyl groups on the ring, even more preferably a 4,4-dimethylcyclohexane ring.

$R^5$ represents a $C_1$-$C_6$ alkoxy group, a $C_3$-$C_8$ cycloalkoxy group, a $C_2$-$C_6$ alkenyloxy group, a $C_1$-$C_6$ alkylamino group, a $C_3$-$C_8$ cycloalkylamino group, or a tetrahydropyranylamino group. $R^5$ is more preferably a $C_1$-$C_6$ alkoxy group or a tetrahydropyranylamino group, even more preferably a $C_1$-$C_6$ alkoxy group.

$R^{22}$ and $R^{23}$ each independently represent a hydrogen atom, a $C_1$-$C_6$ alkyl group optionally having 1 to 3 substituents independently selected from group I below, a $C_1$-$C_6$ alkylsulfonyl group optionally having 1 to 3 substituents independently selected from group I below, a $C_3$-$C_6$ cycloalkyl group optionally having 1 to 3 substituents independently selected from group I below, an azetidinyl group optionally having 1 to 3 substituents independently selected from group I below, a pyrrolidinyl group optionally having 1 to 3 substituents independently selected from group I below, a piperidinyl group optionally having 1 to 3 substituents independently selected from group I below, a piperazinyl group optionally having 1 to 3 substituents independently selected from group I below, a morpholino group optionally having 1 to 3 substituents independently selected from group I below, a phenyl group optionally having 1 to 3 substituents independently selected from group I below, a pyridyl group optionally having 1 to 3 substituents independently selected from group I below, a pyrimidinyl group optionally having 1 to 3 substituents independently selected from group I below, a pyridazinyl group optionally having 1 to 3 substituents independently selected from group I below, a pyrrolyl group optionally having 1 to 3 substituents independently selected from group I below, a pyrazolyl group optionally having 1 to 3 substituents independently selected from group I below, an imidazolyl group optionally having 1 to 3 substituents independently selected from group I below, an oxazolyl group optionally having 1 to 3 substituents independently selected from group I below, an oxadiazolyl group optionally having 1 to 3 substituents independently selected from group I below, or a triazolyl group optionally having 1 to 3 substituents independently selected from group I below:

group I: a halogen atom, a hydroxy group, an oxo group, a carboxy group, a formyl group, an amino group, an aminocarbonyl group, a cyano group, a $C_1$-$C_6$ alkylamino group, a $C_1$-$C_6$ alkylsulfonyl group, a $C_1$-$C_6$ alkylsulfonylamide group, a $C_1$-$C_6$ alkyl group optionally having 1 to 3 substituents independently selected from group J below, a $C_1$-$C_6$ alkoxy group optionally having 1 to 3 substituents independently selected from group J below, a $C_1$-$C_6$ alkylcarbonyl group optionally having 1 to 3 substituents independently selected from group J below, a $C_3$-$C_6$ cycloalkylcarbonyl group optionally having 1 to 3 substituents independently selected from group J below, a $C_4$-$C_6$ cycloalkyl group optionally having 1 to 3 substituents independently selected from group J below, a $C_1$-$C_6$ alkoxycarbonyl group optionally having 1 to 3 substituents independently selected from group J below, a piperidinyl group optionally having 1 to 3 substituents independently selected from group J below, a pyrrolidinyl group optionally having 1 to 3 substituents independently selected from group J below, a piperazinyl group optionally having 1 to 3 substituents independently selected from group J below, a phenyl group optionally having 1 to 3 substituents independently selected from group J below, a tetrazolyl group, an azetidinyl group optionally having 1 to 3 substituents independently selected from group J below, a morpholinyl group optionally having 1 to 3 substituents independently selected from group J below, a dihydropyrazolyl group optionally having 1 to 3 substituents independently selected from group J below, and an oxadiazolyl group:

group J: a halogen atom, a hydroxy group, an amino group, a carboxy group, an aminocarbonyl group, a phenyl group, a $C_1$-$C_6$ alkyl group, a $C_1$-$C_6$ alkylamino group, a di-$C_1$-$C_6$ alkylamino group, a $C_1$-$C_6$ alkylcarbonyl group, a $C_3$-$C_6$ cycloalkyl group, a $C_1$-$C_6$ alkylsulfonyl group, and a $C_1$-$C_6$ alkylsulfonylamide group.

$R^{22}$ and $R^{23}$ are, more preferably, each independently a hydrogen atom, a methyl group, a methylsulfonyl group, or any of the following $T^1$ to $T^{35}$:

[Formula 37-1]

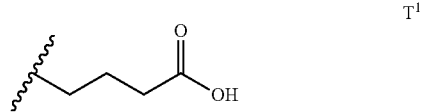

$T^1$

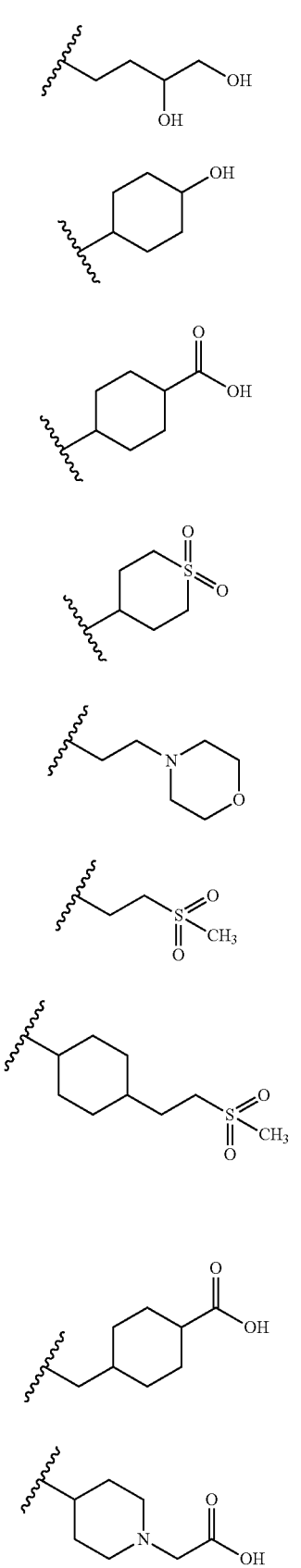
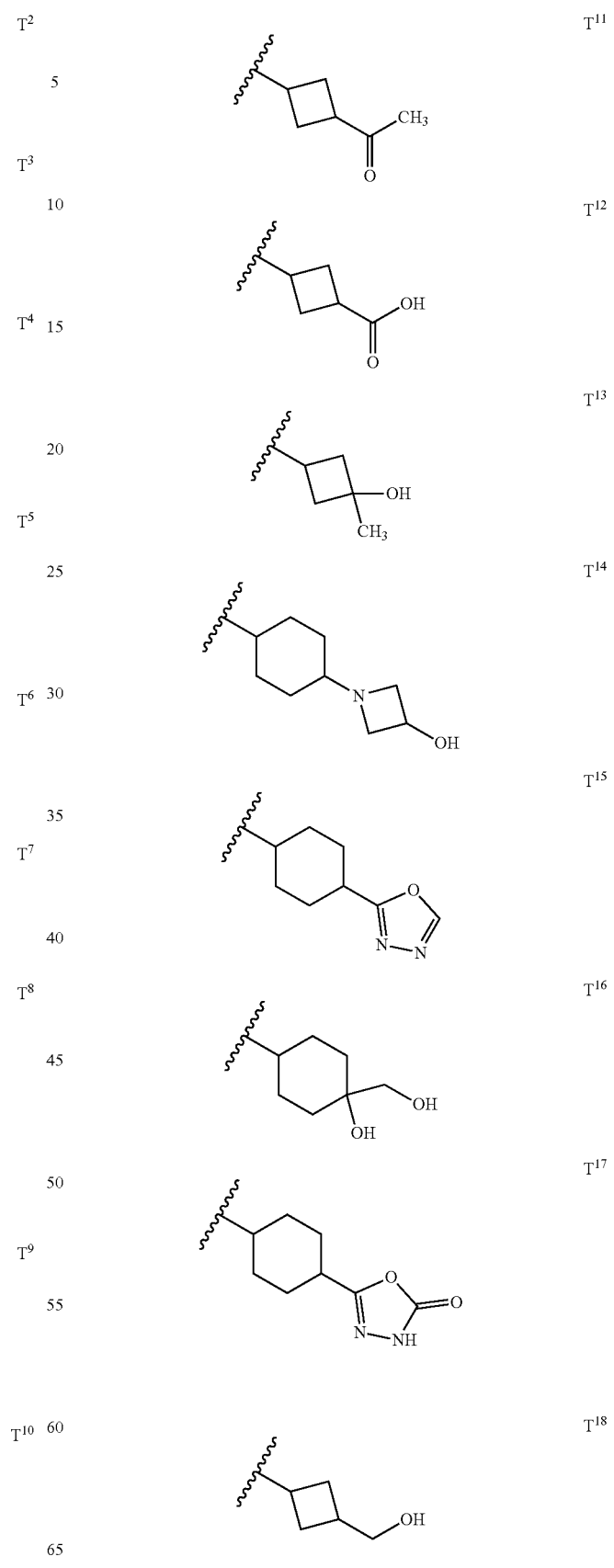

-continued

T19 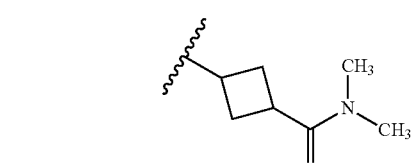

[[Formula 37-2]]

T20 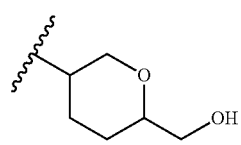

T21 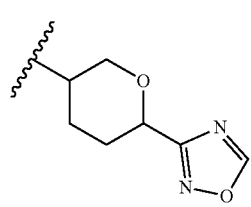

T23 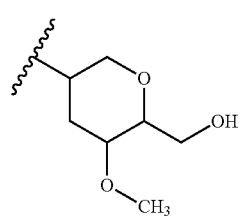

T24 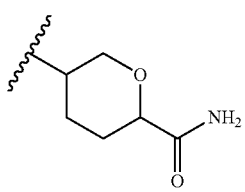

T25 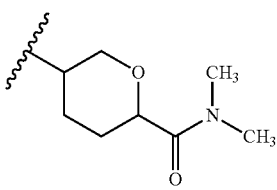

T26 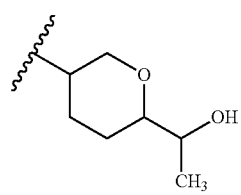

T27 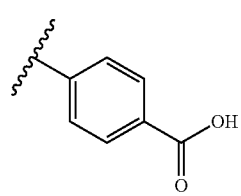

-continued

T28 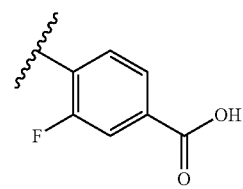

T29 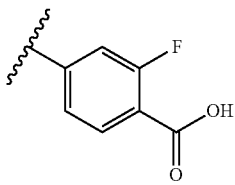

T30 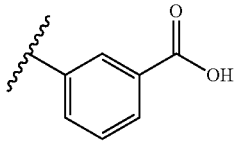

T31 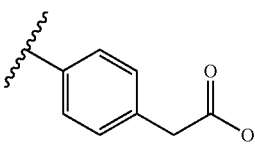

T32 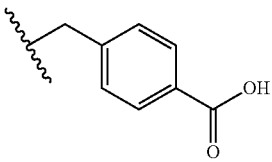

T33 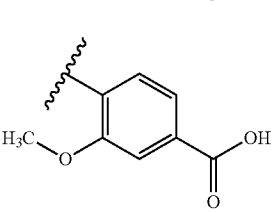

T34 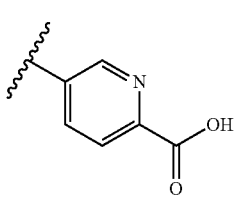

T35 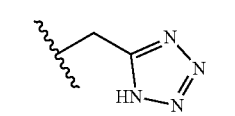

M is a nitrogen atom or CH and is more preferably a nitrogen atom.

L is $CH_2$ or $C(CH_3)_2$ and is more preferably $C(CH_3)_2$.

$R^{53}$ is a $C_1$-$C_6$ alkyl group.

In a preferred combination of the substituents in the compound represented by the formula (I), $R^1$ is a hydrogen atom, $R^2$ is a phenyl group having one fluorine atom and one chlorine atom, and ring Z is a benzene ring having one chlorine atom.

In a preferred combination of the substituents in the compound represented by formula (V), $R^3$ and $R^4$ together form a 4,4-dimethylcyclohexane ring, and $R^5$ is a $C_1$-$C_6$ alkoxy group.

In a preferred combination of the substituents in the compound represented by formula (IV) or the compound represented by formula (XIII) in the present invention, $R^1$ is a hydrogen atom, $R^2$ is a phenyl group having one fluorine atom and one chlorine atom, ring Z is a benzene ring having one chlorine atom, $R^3$ and $R^4$ together form a 4,4-dimethylcyclohexane ring, and $R^5$ is a $C_1$-$C_6$ alkoxy group.

In a preferred combination of the substituents in the compound represented by formula (XIV), $R^1$ is a hydrogen atom, $R^2$ is a phenyl group having one fluorine atom and one chlorine atom, ring Z is a benzene ring having one chlorine atom, and $R^3$ and $R^4$ together form a 4,4-dimethylcyclohexane ring.

In a preferred combination of the substituents in the compound represented by formula (XV), $R^1$ is a hydrogen atom, $R^2$ is a phenyl group having one fluorine atom and one chlorine atom, ring Z is a benzene ring having one chlorine atom, $R^3$ and $R^4$ together form a 4,4-dimethylcyclohexane ring, and each of $R^{22}$ and $R^{23}$ is $T^{24}$ mentioned above.

In a preferred combination of the substituents in the compound represented by formula (XIX), M is a nitrogen atom, L is $C(CH_3)_2$, and $R^{53}$ is a $C_1$-$C_6$ alkyl group.

In a preferred combination of the substituents in the compound represented by formula (XX), L is $C(CH_3)_2$, and $R^{53}$ is a $C_1$-$C_6$ alkyl group.

In a preferred combination of the substituents in the compound represented by formula (XXI) or the compound represented by formula (XXII), M is a nitrogen atom, and L is $C(CH_3)_2$.

Next, preferred compounds of the compound represented by formula (VI), the compound represented by formula (VII), the compound represented by formula (VIII), the compound represented by formula (IX), the compound represented by formula (X), the compound represented by formula (XI), and the compound represented by formula (XII) will be described.

The compound represented by formula (VI) is a BINAP derivative and is preferably a compound represented by any of the following formulae:

[Formula 38]

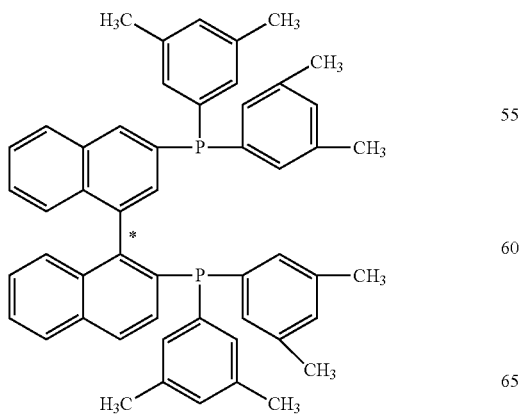

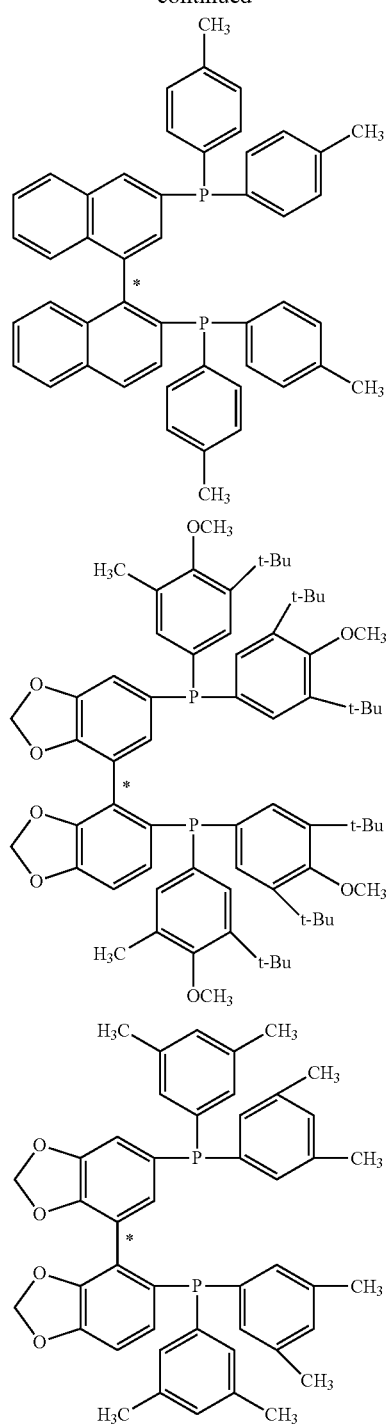

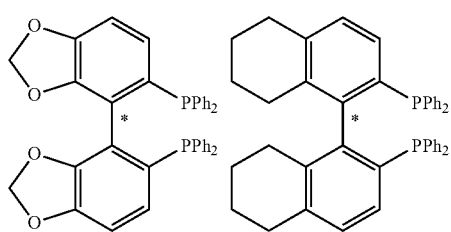

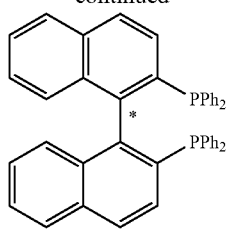
more preferably a compound represented by any of the following formulae:
[Formula 39]
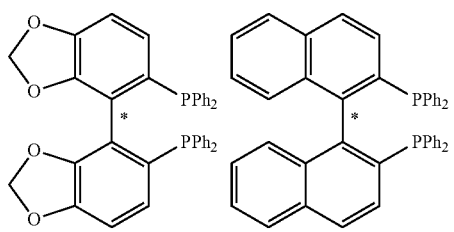
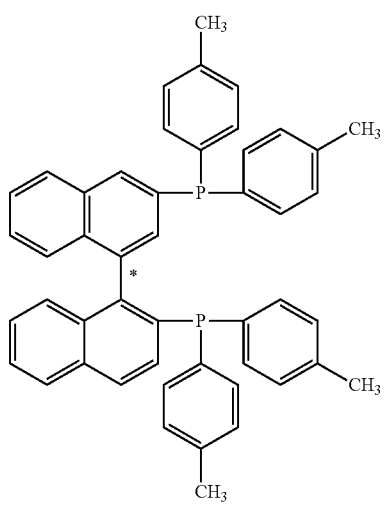
The compound represented by formula (VII) is a MeBIO-PHEP derivative, a P-Phos derivative, or a TunePHOS derivative and is preferably a compound represented by any of the following formulae:
[Formula 40]
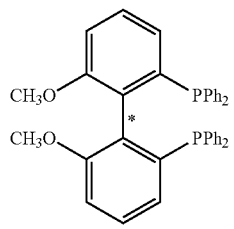
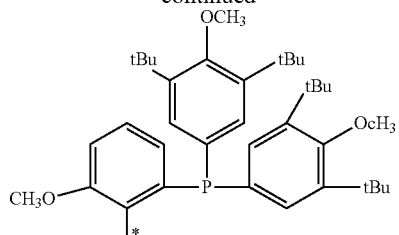
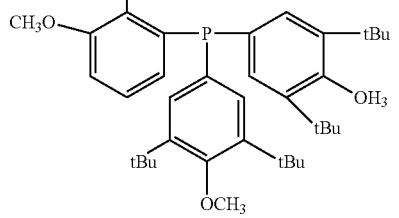
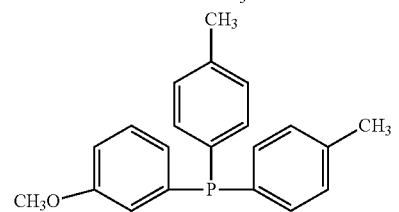
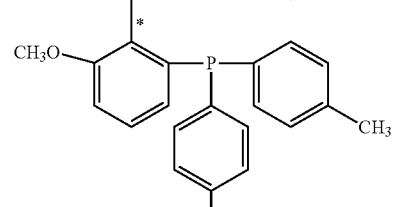
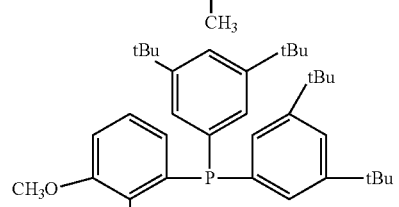
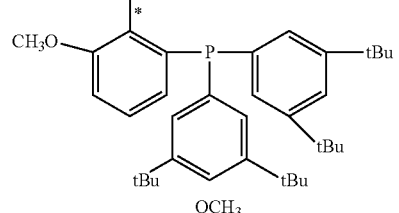
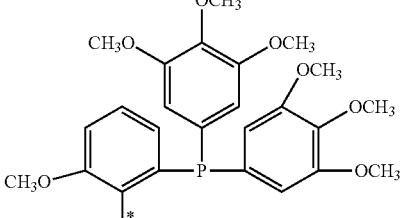
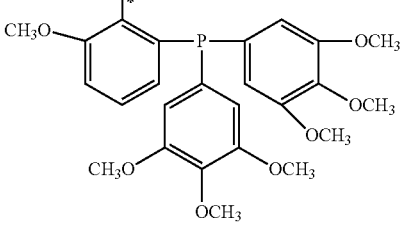

-continued

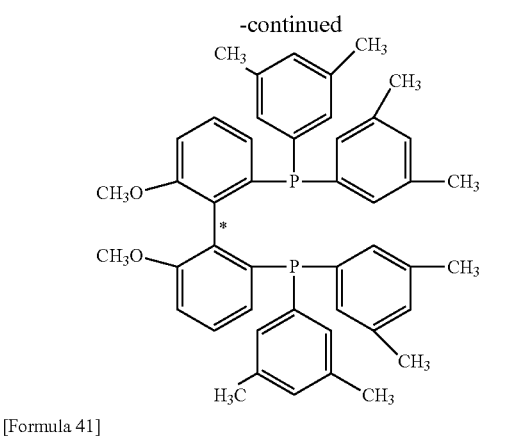

[Formula 41]

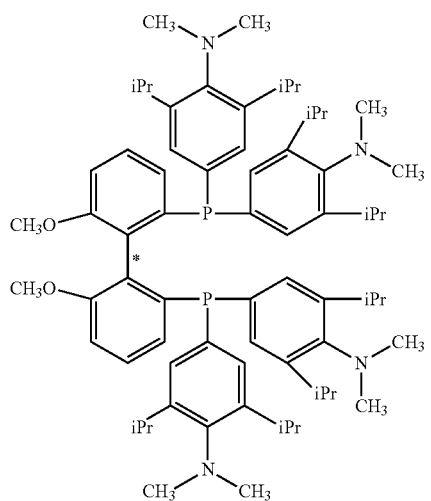

more preferably a compound represented by any of the following formulae:

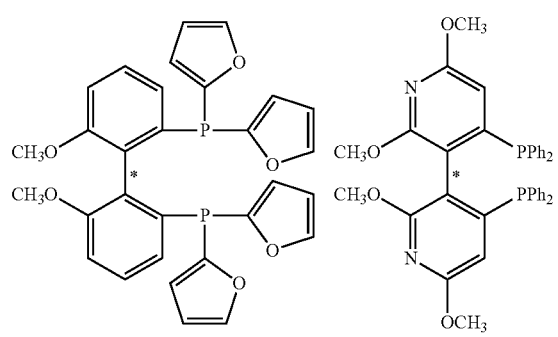

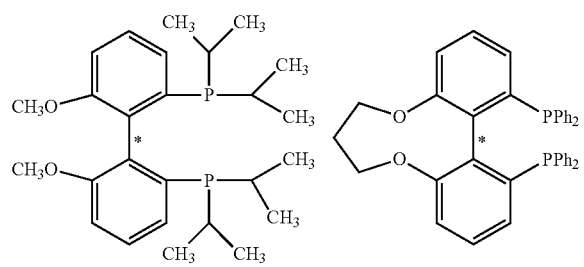

[Formula 42]

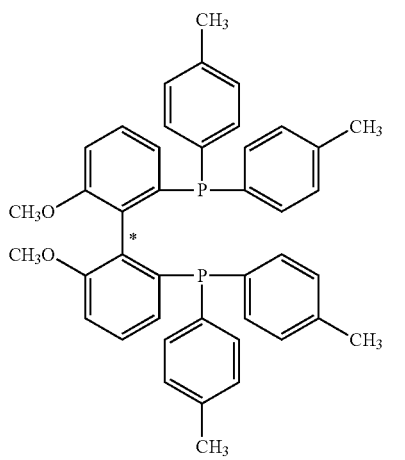

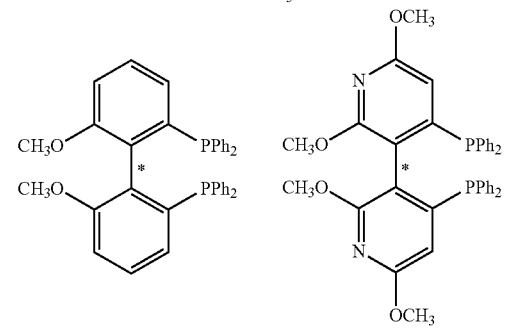

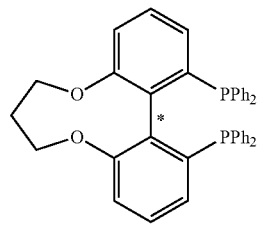

The compound represented by formula (VIII) is a JOSIPHOS derivative, a Walphos derivative, a FESULPHOS derivative, a Taniaphos derivative, a Jospophos derivative, or a FOXAP derivative and is preferably a compound represented by any of the following formulas:

[Formula 43]

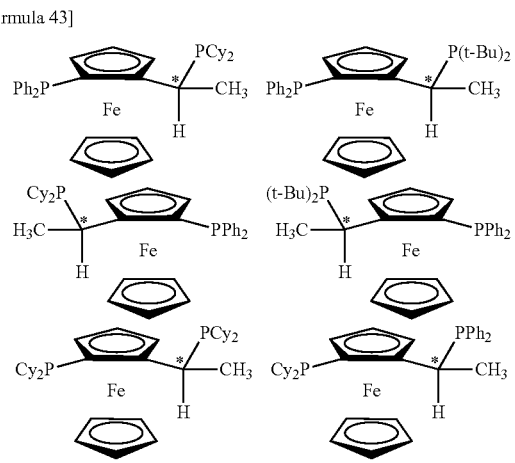

-continued
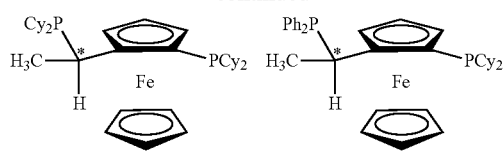
[Formula 44-1]
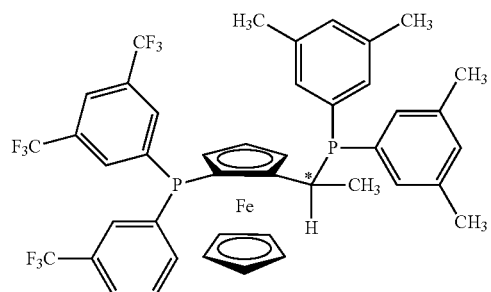
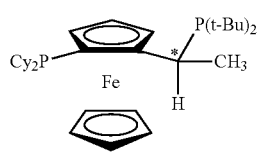
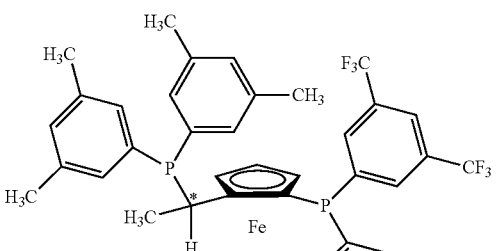
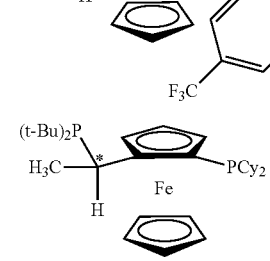
[Formula 44-2]
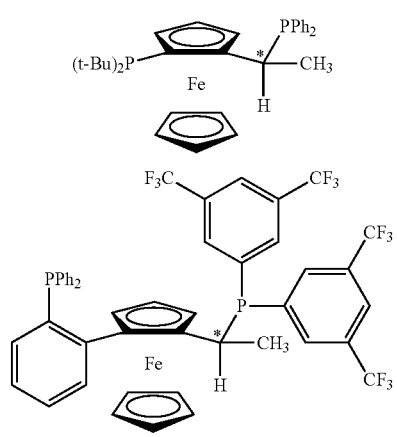
-continued
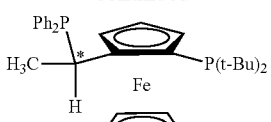
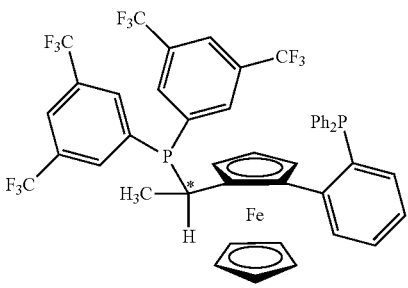
[Formula 45-1]
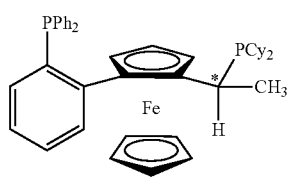
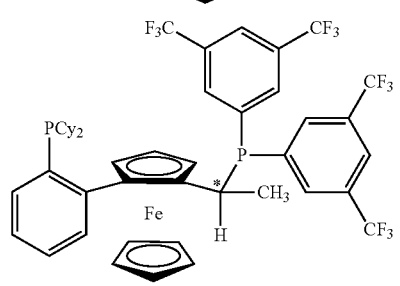
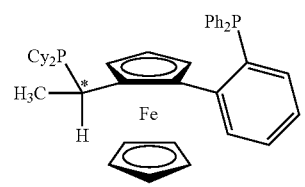
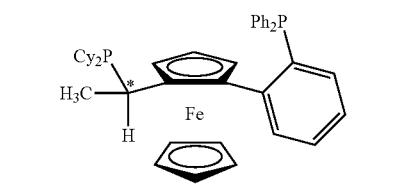
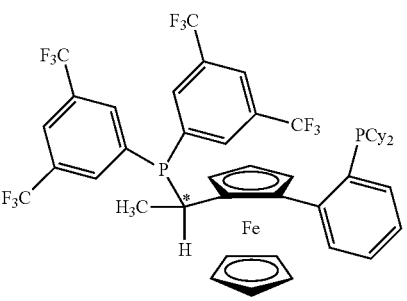
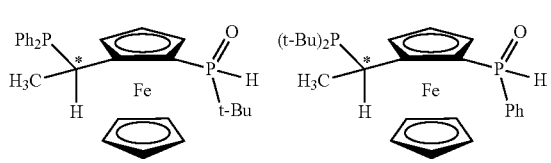

[Formula 45-2]

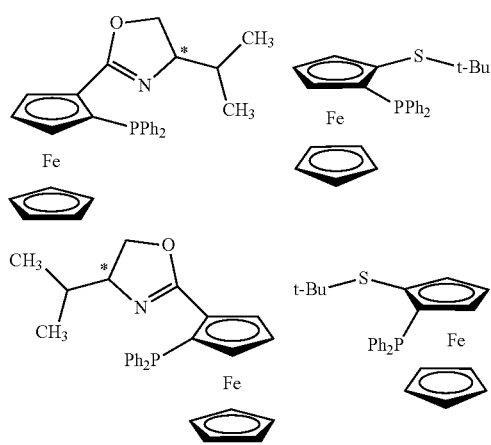

[Formula 46]

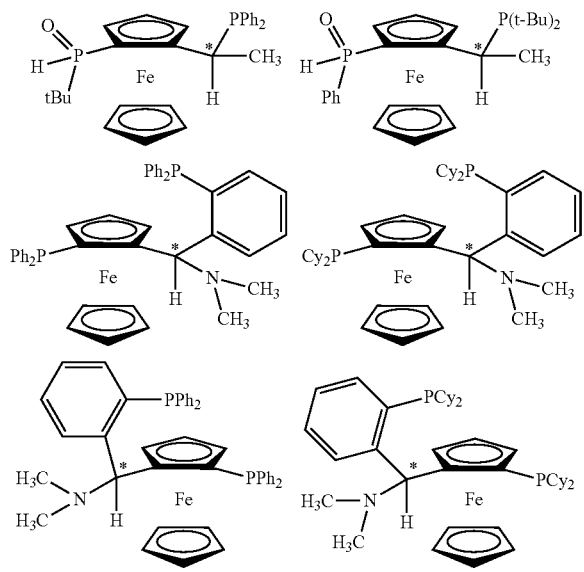

more preferably a compound represented by any of the following formulae:

[Formula 47]

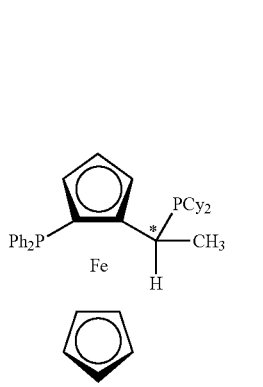

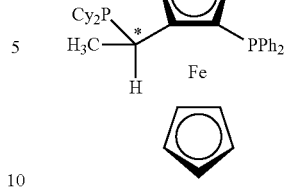

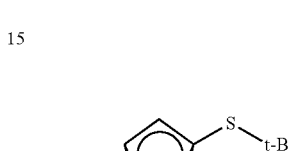

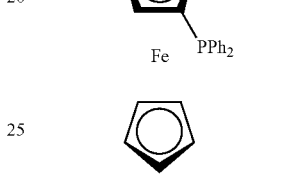

The compound represented by formula (IX) is a Mandyphos derivative and is preferably a compound represented by any of the following formulae:

[Formula 48]

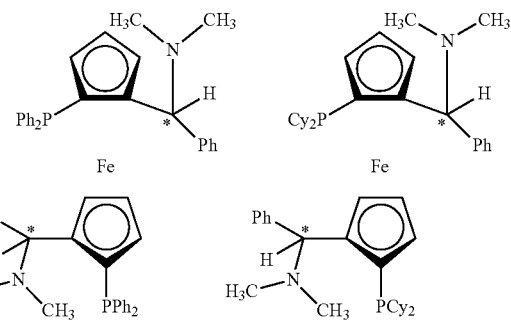

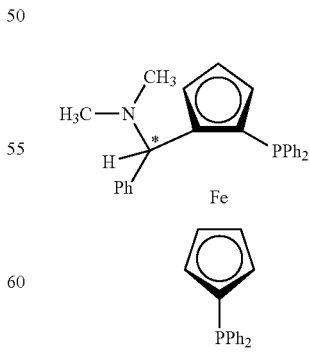

The compound represented by formula (X) is a Ferrocelane derivative and is preferably a compound represented by any of the following formula:

[Formula 49-1]
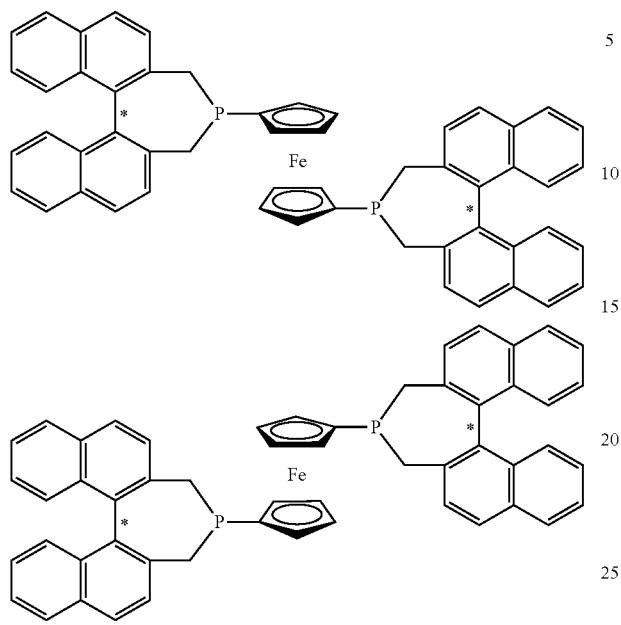
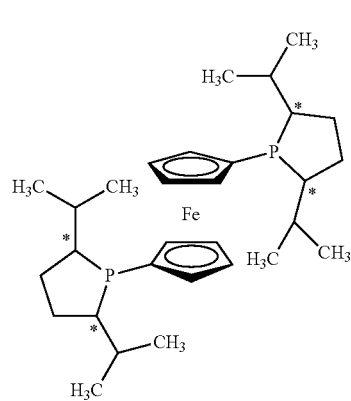
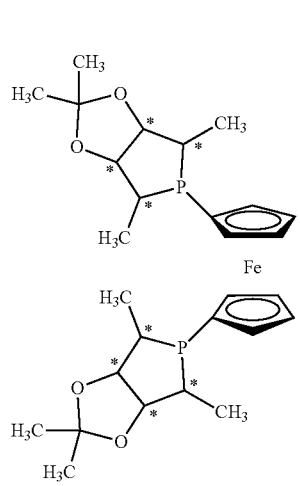
[Formula 49-2]
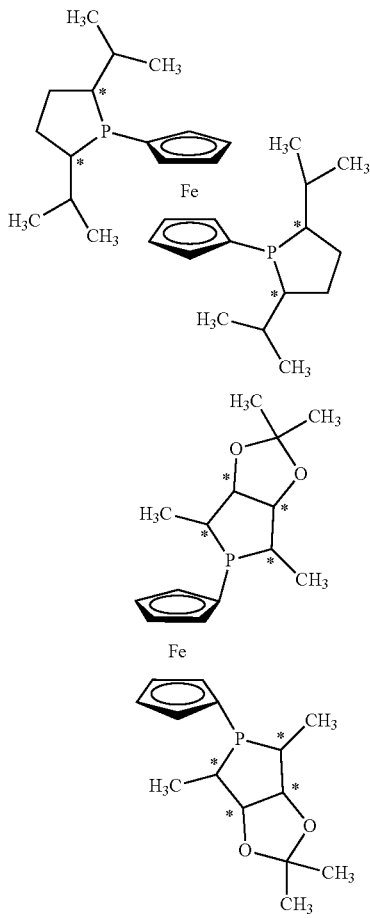
The compound represented by formula (XI) is a PHOX derivative and is preferably a compound represented by any of the following formulae:
[Formula 50]
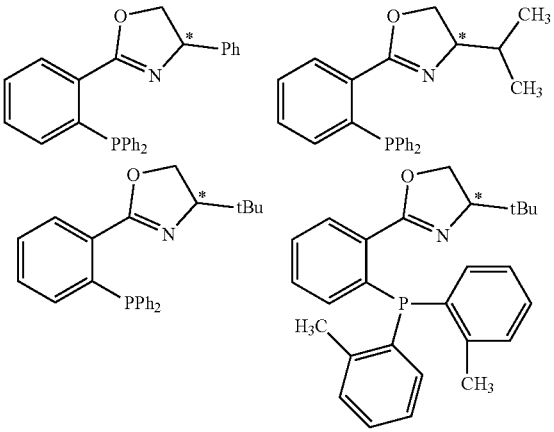
The compound represented by formula (XII) is a QuinoxP derivative and is preferably a compound represented by the following formula:

[Formula 51]

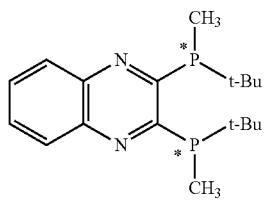

In the present invention, the Lewis acid is CuOAc, CuCl, CuBr, CuI, CuOTf, CuPF$_6$, CuBF$_4$, Cu(OAc)$_2$, Cu(OTf)$_2$, or CuSO$_4$ and is more preferably CuOAc or Cu(OAc)$_2$.

In the present invention, a preferred combination of the Lewis acid and the chiral ligand is CuOAc or Cu(OAc)$_2$ as the Lewis acid and a compound represented by any of the following formulae as the chiral ligand:

[Formula 52]

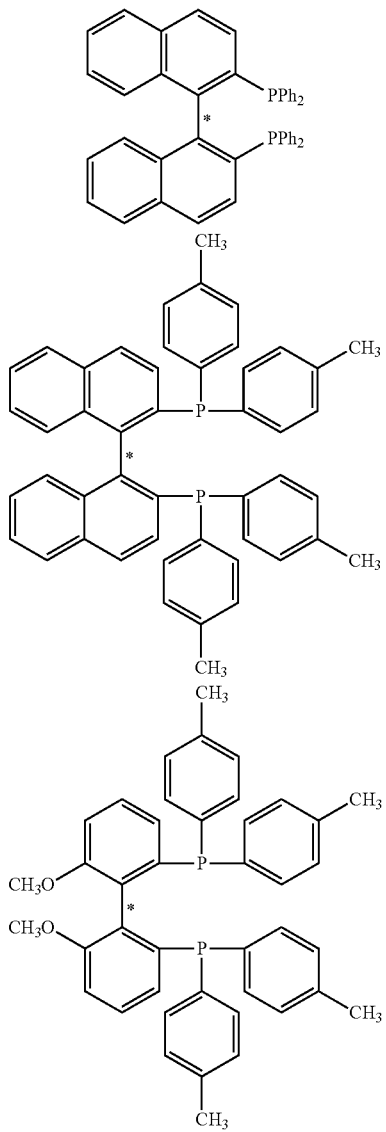

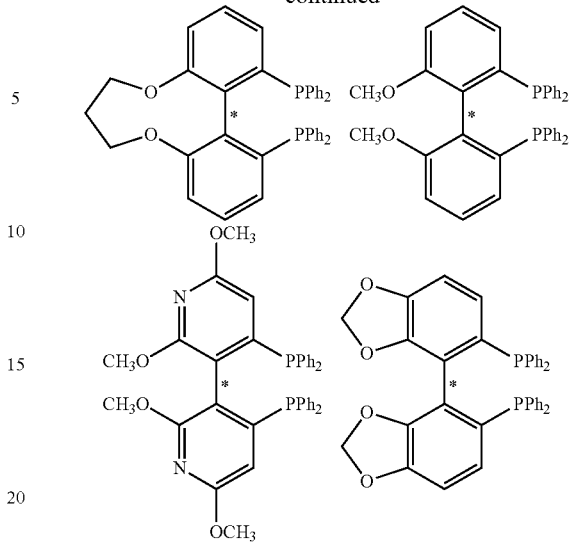

[Formula 53]

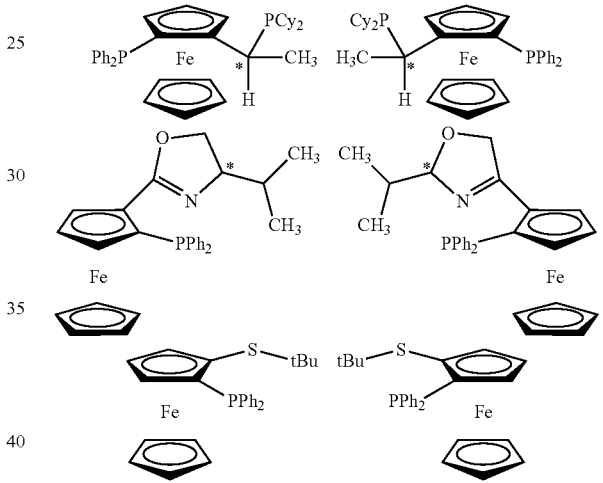

In the present invention, the solvent is preferably one or two selected from the group consisting of N,N-dimethylacetamide, tetrahydrofuran, dimethoxyethane, 2-propanol, toluene, and ethyl acetate, more preferably one or two selected from the group consisting of N,N-dimethylacetamide and ethyl acetate. Alternatively, a mixture of the solvents in an arbitrary ratio may be used.

Next, the present invention will be described. It should be understood that the reaction conditions of the present invention are not limited to those described herein. In the present invention, a functional group in a compound may be protected with an appropriate protective group. Examples of such a functional group can include a hydroxy group, a carboxy group, and an amino group. For the type of protective group and conditions for the introduction and removal of the protective group, see those described in, for example, Protective Groups in Organic Synthesis (T. W. Greene and P. G. M. Wuts, John Wiley & Sons, Inc., New York, 2006).

[Production Method]
1) Method for producing a compound represented by formula (IV)

[Formula 54]

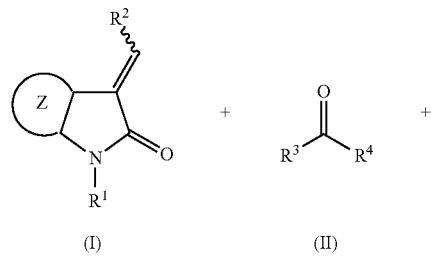

(I)  (II)

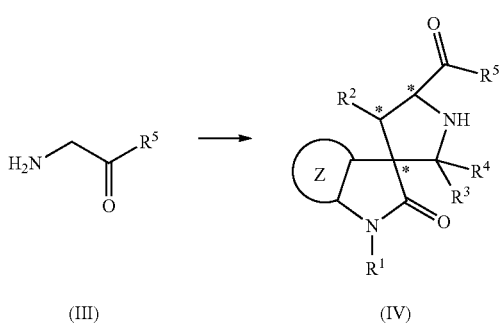

(III)  (IV)

A compound represented by formula (IV) is obtained by reacting a compound represented by formula (I), a compound represented by formula (II), and a compound represented by formula (III) in the presence of an asymmetric catalyst prepared from a Lewis acid and a chiral ligand, and a solvent. Also, the compound represented by formula (IV) can be obtained by forming in advance a compound represented by formula (V) (ketimine) from a compound represented by formula (II) and a compound represented by formula (III) and then reacting the ketimine with a compound represented by formula (I).

The reaction is preferably carried out in the presence of a base.

A compound represented by the formula (I) can be produced according to various references (e.g., WO2006/091646 and WO2012/121361).

The amount of the compound represented by formula (II) used is in the range of 0.5 equivalents to 10 equivalents with respect to the compound represented by formula (I) and is preferably in the range of 1.0 equivalent to 3.0 equivalents with respect to the compound represented by formula (I).

The amount of the compound represented by formula (III) used is in the range of 0.5 equivalents to 10 equivalents with respect to the compound represented by formula (I) and is preferably in the range of 1.0 equivalent to 3.0 equivalents with respect to the compound represented by formula (I).

Examples of the Lewis acid that can be used include a Zn(II) Lewis acid, a Ag(I) Lewis acid, a Ni(II) Lewis acid, a Co(II) Lewis acid, a Ru(I) Lewis acid, a Cu(I) Lewis acid, and a Cu(II) Lewis acid. The Lewis acid is preferably CuOAc, CuCl, CuBr, CuI, CuOTf, $CuPF_6$, $CuBF_4$, $Cu(OAc)_2$, $Cu(OTf)_2$, or $CuSO_4$.

As for the amounts of the Lewis acid and the chiral ligand used, the ligand is preferably added in the range of 0.8 to 3.0 equivalents with respect to the Lewis acid and in the range of 0.01 to 100 mol % of the Lewis acid with respect to the compound represented by formula (I). More preferably, the ligand is added in the range of 1.01 to 2.4 equivalents with respect to the Lewis acid and in the range of 0.5 to 20 mol % of the Lewis acid with respect to the compound (I).

Examples of the chiral ligand that can be used include BINAP derivatives, MeBIPHEP derivatives, TunePHOS derivatives, P-Phos derivatives, JOSIPHOS derivatives, Walphos derivatives, FESULPHOS derivatives, Taniaphos derivatives, Jospophos derivatives, FOXAP derivatives, Mandyphos derivatives, Ferrocelane derivatives, PHOX derivatives, and QuinoxP derivatives. The chiral ligand is preferably a BINAP derivative, a Tunephos derivative, a MeBIPHEP derivative, a P-Phos derivative, a JOSIPHOS derivative, a FOXAP derivative, a FESULPHOS derivative, or the like.

The chiral ligand can be purchased from, for example, Sigma-Aldrich Inc., Tokyo Chemical Industry Co., Ltd., Wako Pure Chemical Industries, Ltd., or Strem Chemicals Inc.

Examples of the base that can be used include: tertiary amines such as triethylamine and N,N-diisopropylethylamine; organic bases such as sodium ethoxide and t-butoxy potassium; and inorganic bases such as sodium hydroxide, sodium carbonate, sodium bicarbonate, sodium acetate, potassium hydroxide, potassium carbonate, potassium bicarbonate, and potassium acetate. The base is preferably a tertiary amine such as triethylamine or N,N-diisopropylethylamine, more preferably triethylamine.

The amount of the base used is in the range of 0.01 equivalents to 10 equivalents with respect to the compound represented by formula (I) and is preferably in the range of 0.01 equivalents to 0.2 equivalents with respect to the compound represented by formula (I).

Examples of the solvent include: ether solvents such as tetrahydrofuran and 1,2-dimethoxyethane; alcohol solvents such as methanol, ethanol, and 2-propanol; hydrocarbon solvents such as toluene; nitrile solvents such as acetonitrile; aliphatic ester solvents such as ethyl acetate; and amide solvents such as N,N-dimethylacetamide and N,N-dimethylformamide. These solvents can be used alone or as a mixture in an arbitrary ratio. Preferably, ether solvents such as tetrahydrofuran, amide solvents such as N,N-dimethylacetamide, and aliphatic ester solvents such as ethyl acetate are preferably used alone or as a mixture in an arbitrary ratio.

The amount of the solvent used is in the range of 1 to 100 times the amount of the compound (I) and is preferably in the range of 5 to 50 times the amount of the compound represented by formula (I), more preferably in the range of 8 to 25 times the amount of the compound represented by formula (I).

The reaction temperature is in the range of –88° C. to the boiling point of the solvent used and is preferably in the range of –20° C. to 60° C.

The reaction time is in the range of 30 minutes to 96 hours and is preferably in the range of 30 minutes to 64 hours, more preferably in the range of 30 minutes to 48 hours.

2) Method for Producing a Compound Represented by Formula (XIV)

[Formula 55]

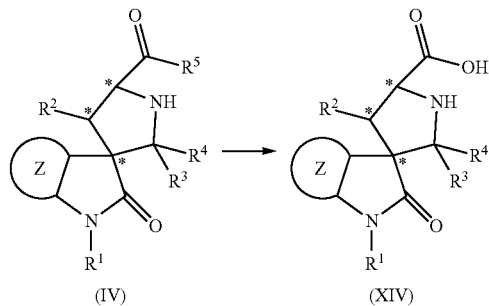

A compound represented by formula (XIV) is obtained by hydrolyzing a compound represented by formula (IV) (provided that $R^5$ is not —$NR^{51}R^{52}$).

The hydrolysis can be carried out by the addition of a base or an acid in a solvent.

Examples of the base that can be used include: organic bases such as sodium ethoxide and t-butoxy potassium; and inorganic bases such as sodium hydroxide, lithium hydroxide, sodium carbonate, potassium hydroxide, and potassium carbonate. The base is preferably an inorganic base such as sodium hydroxide, lithium hydroxide, or potassium hydroxide, more preferably sodium hydroxide.

The amount of the base used is in the range of 1 equivalent to 10 equivalents with respect to the compound represented by formula (IV) and is preferably in the range of 1 equivalent to 5 equivalents with respect to the compound represented by formula (IV), more preferably in the range of 1 equivalent to 3 equivalents with respect to the compound represented by formula (IV).

Examples of the acid include: hydrohalic acids such as hydrofluoric acid, hydrochloric acid, hydrobromic acid, and hydroiodic acid; inorganic acids such as nitric acid, perchloric acid, sulfuric acid, and phosphoric acid; $C_1$-$C_6$ alkylsulfonic acids such as methanesulfonic acid, trifluoromethanesulfonic acid, and ethanesulfonic acid; arylsulfonic acids such as benzenesulfonic acid and p-toluenesulfonic acid; and carboxylic acids such as acetic acid, trifluoroacetic acid, oxalic acid, tartaric acid, and maleic acid. The acid is preferably trifluoroacetic acid or hydrochloric acid.

The amount of the acid used is in the range of 1 equivalent to 100 equivalents with respect to the compound represented by formula (IV) and is preferably in the range of 1 equivalent to 10 equivalents with respect to the compound represented by formula (IV).

Examples of the solvent include: ether solvents such as tetrahydrofuran and 1,2-dimethoxyethane; alcohol solvents such as methanol, ethanol, and 2-propanol; hydrocarbon solvents such as toluene; nitrile solvents such as acetonitrile; aliphatic ester solvents such as ethyl acetate; amide solvents such as N,N-dimethylacetamide and N,N-dimethylformamide; and halogen solvents such as dichloromethane and chloroform. These solvents can be used alone or as a mixture at an arbitrary ratio. The solvent is preferably a halogen solvent such as dichloromethane, an alcohol solvent such as methanol, or a mixed solvent of an ether solvent such as tetrahydrofuran and an alcohol solvent such as methanol.

The amount of the solvent used is in the range of 1 to 100 times the amount of the compound represented by formula (IV) and is preferably in the range of 5 to 50 times the amount of the compound represented by formula (IV), more preferably in the range of 8 to 25 times the amount of the compound represented by formula (IV).

The reaction temperature is in the range of −88° C. to the boiling point of the solvent used and is preferably in the range of −20° C. to 60° C.

The reaction time is in the range of 30 minutes to 96 hours and is preferably in the range of 30 minutes to 64 hours, more preferably in the range of 30 minutes to 48 hours.

3) Method for Producing a Compound Represented by Formula (XV)

[Formula 56]

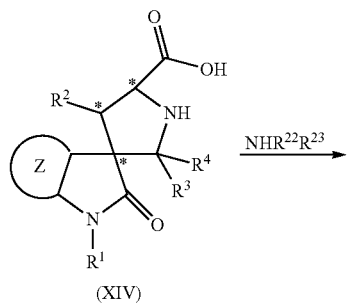

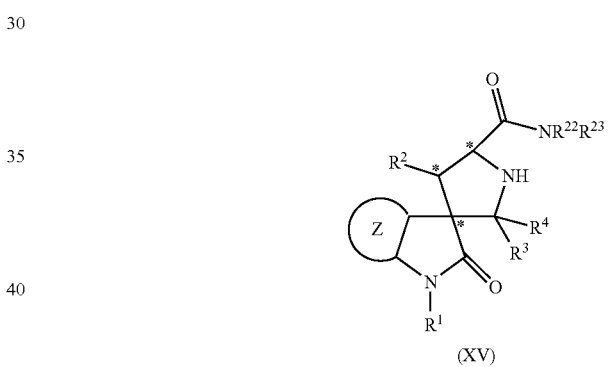

A compound represented by formula (XV) is obtained by condensing a compound represented by formula (XIV) with an amine $NHR^{22}R^{23}$ using a condensing agent in a solvent. The amine can be produced according to various references (e.g., WO2006/091646 and WO2012/121361).

The amount of the amine used is in the range of 0.5 equivalents to 10 equivalents with respect to the compound represented by formula (XIV) and is preferably in the range of 1.0 equivalent to 2.0 equivalents with respect to the compound represented by formula (XIV).

Examples of the condensing agent include: azodicarboxylic acid di-lower alkyl ester-triphenylphosphines such as azodicarboxylic acid diethyl ester-triphenylphosphine; carbodiimide derivatives such as N,N'-dicyclohexylcarbodiimide (DCC) and 1-ethyl-3-(3-dimethylaminopropyl)carbodiimide (EDCI); 2-halo-1-lower alkylpyridinium halides such as 2-chloro-1-methylpyridinium iodide; diarylphosphorylazides such as diphenylphosphorylazide (DPPA); phosphoryl chlorides such as diethylphosphoryl chloride; imidazole derivatives such as N,N'-carbodiimidazole (CDI); benzotriazole derivatives such as benzotriazol-1-yloxy-tris (dimethylamino)phosphonium hexafluorophosphate (BOP), O-(benzotriazol-1-yl)-N,N,N',N'-tetramethyluronium hexafluorophosphate (HBTU), O-(7-azabenzotriazol-1-yl)-N,N,N',N'-tetramethyluronium hexafluorophosphate (HATU), and (1H-benzotriazol-1-yloxy)tripyrrolidinophosphonium hexafluorophosphate (PyBOP); and triazine derivatives such as 4-(4,6-dimethoxy-1,3,5-triazin-2-yl)-4-methylmorpholinium chloride (DM-TMM). The condensing agent is preferably 1-ethyl-3-(3-dimethylaminopropyl)carbodiimide (EDCI), O-(benzotriazol-1-yl)-N,N,N',N'-tetramethyluronium hexafluorophosphate (HBTU), O-(7-azabenzotriazol-1-yl)-N,N,N',N'-tetramethyluronium hexafluorophosphate (HATU), (1H-benzotriazol-1-yloxy)tripyrrolidinophosphonium hexafluorophosphate (PyBOP), diphenylphosphorylazide (DPPA), or 4-(4,6-dimethoxy-1,3,5-triazin-2-yl)-4-methylmorpholinium chloride (DM-TMM).

The amount of the condensing agent used is in the range of 1 equivalent to 10 equivalents with respect to the compound represented by formula (XIV) and is preferably in the range of 1 equivalent to 5 equivalents with respect to the compound represented by formula (XIV), more preferably in the range of 1 equivalent to 2 equivalents with respect to the compound represented by formula (XIV).

Examples of the solvent that can be used include: ether solvents such as tetrahydrofuran and 1,2-dimethoxyethane; alcohol solvents such as methanol, ethanol, and 2-propanol; hydrocarbon solvents such as toluene; nitrile solvents such as acetonitrile; aliphatic ester solvents such as ethyl acetate; and amide solvents such as N,N-dimethylacetamide and N,N-dimethylformamide. The solvent is preferably an amide solvent such as N,N-dimethylacetamide.

The amount of the solvent used is in the range of 1 to 100 times the amount of the compound represented by formula (XIV) and is preferably in the range of 3 to 50 times the amount of the compound represented by formula (XIV), more preferably in the range of 5 to 25 times the amount of the compound represented by formula (XIV).

The reaction temperature is in the range of −88° C. to the boiling point of the solvent used and is preferably in the range of −20° C. to 60° C.

The reaction time is in the range of 30 minutes to 96 hours and is preferably in the range of 30 minutes to 64 hours, more preferably in the range of 30 minutes to 48 hours.

EXAMPLES

Hereinafter, the present invention will be described in more detail with reference to Examples. However, the scope of the present invention is not intended to be limited by them.

Abbreviations used in the Examples are as defined below. mg: milligram, g: gram, ml: milliliter, L: liter, MHz: megahertz.

In the Examples below, nuclear magnetic resonance (hereinafter, referred to as 1H NMR; 500 MHz) spectra were indicated by the δ value (ppm) of chemical shift with tetramethylsilane as a standard. As for split patterns, s: singlet, d: doublet, t: triplet, q: quartet, m: multiplet, and br: broad. In the present Examples, "UHPLC" or "ultrahigh-performance liquid chromatography" was performed using Prominence UFLC (Shimadzu Corp.).

Example 1

Ethyl (3'R,4'S,5'R)-6"-chloro-4'-(3-chloro-2-fluorophenyl)-2"-oxo-1",2"-dihydrodispiro[cyclohexane-1,2'-pyrrolidine-3',3"-indole]-5'-carboxylate

[Formula 57]

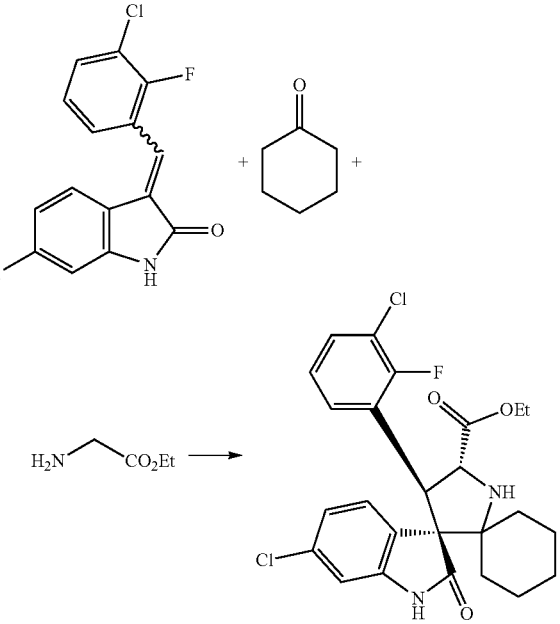

To a mixture of (3E/Z)-6-chloro-3-(3-chloro-2-fluorobenzylidene)-1,3-dihydro-2H-indol-2-one (WO2006/091646) (99.9 mg, 0.32 mmol), (R)-BINAP (12.1 mg, 0.019 mmol), and CuOAc (2.0 mg, 0.016 mmol), a solution of cyclohexanone (50.4 μL, 0.49 mmol), glycine ethyl ester (39.6 LL, 0.39 mmol) and triethylamine (6.8 μL, 0.049 mmol) in N,N-dimethylacetamide (2.0 mL) was added under a nitrogen atmosphere, and the resulting mixture was stirred at room temperature for 40 hours. To the reaction mixture, ethyl acetate (2 mL), water (1 mL), and a 20% aqueous ammonium chloride solution (1 mL) were added, and the mixture was vigorously stirred to separate an organic layer. The aqueous layer was subjected to extraction with ethyl acetate twice (2 mL each), and the organic layers were all combined and then washed with water three times (5 mL each). The organic layer obtained was concentrated under reduced pressure. To the residue, ethyl acetate (6 mL) and silica gel (500 mg) were added, and the silica gel was filtered off. The filtrate was concentrated under reduced pressure. To the residue, ethanol (1.25 mL) was added, then water (1 mL) was added dropwise, and the mixture was stirred overnight at room temperature. The deposited solid was filtered and dried under reduced pressure at 40° C. to obtain the title compound (102.9 mg, yield: 65%, 91% ee) as a solid.

$^1$H NMR (500 MHz, CDCl$_3$): δ=0.91-1.60 (m, 2H), 1.17 (t, J=7.3 Hz, 3H), 1.38-1.74 (m, 6H), 1.87-2.0 (m, 1H), 2.12-2.20 (m, 1H), 3.19 (s, 1H), 4.07-4.20 (m, 2H), 4.54 (d, J=9.0 Hz, 1H), 4.84 (d, J=9.0 Hz, 1H), 6.73 (d, J=2.0 Hz, 1H), 6.83-6.89 (m, 1H), 7.05 (dd, J=8.3, 1.8 Hz, 1H), 7.10-7.16 (m, 1H), 7.36 (dd, J=8.0, 2.0 Hz, 1H), 7.49-7.55 (m, 1H), 7.65 (s, 1H).

(Conditions for High-Performance Liquid Chromatography (HPLC) for Optical Purity Measurement)
Column: CHIRALPAK IC 4.6×250 mm, 5 μm
Mobile phase: 10 mM AcOH buffer:MeCN=40:60
Flow rate: 1.0 min/min
Column temperature: 40° C.
Detection wavelength: 254 nm
Injection quantity: 5 μL
Retention time: title compound=14.1 min, enantiomer=11.4 min Example 2

Ethyl (3'R,4'S,5'R)-6"-chloro-4'-(3-chloro-2-fluorophenyl)-4,4-dimethyl-2"-oxo-1",2"-dihydrodispiro[cyclohexane-1,2'-pyrrolidine-3',3"-indole]-5'-carboxylate

[Formula 58]

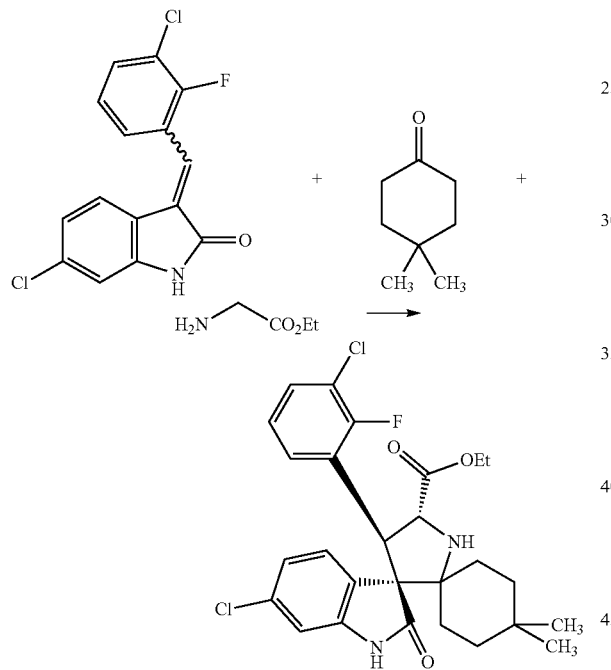

To a mixture of (3E/Z)-6-chloro-3-(3-chloro-2-fluorobenzylidene)-1,3-dihydro-2H-indol-2-one (WO2006/091646) (98.7 mg), (R)-BINAP (12.1 mg, 0.019 mmol), and CuOAc (2.0 mg, 0.016 mmol), a solution of 4,4-dimethlcyclohexanone (61.4 mg, 0.48 mmol), glycine ethyl ester (39.5 LL, 0.39 mmol) and triethylamine (6.8 μL, 0.049 mmol) in N,N-dimethylacetamide (2.0 mL) was added under a nitrogen atmosphere, and the resulting mixture was stirred at room temperature for 22 hours. To the reaction mixture, ethyl acetate (2 mL), water (1 mL), and a 20% aqueous ammonium chloride solution (1 mL) were added, and the mixture was vigorously stirred to separate an organic layer. The aqueous layer was subjected to extraction with ethyl acetate twice (2 mL each), and the organic layers were all combined and then washed with water three times (5 mL each). The organic layer obtained was concentrated under reduced pressure. To the residue, ethyl acetate (6 mL) and silica gel (500 mg) were added, and the silica gel was filtered off. The filtrate was concentrated under reduced pressure. To the residue, ethanol (1.0 mL) was added, then water (1 mL) was added dropwise, and the mixture was stirred overnight at room temperature. The deposited solid was filtered and dried under reduced pressure at 40° C. to obtain the title compound (137 mg, yield: 82%, 94% ee) as a solid.

$^1$H NMR (500 MHz, CDCl$_3$): δ=0.67 (s, 3H), 0.91 (s, 3H), 1.10-1.19 (m, 2H), 1.17 (t, J=7.3 Hz, 3H), 1.25-1.33 (m, 1H), 1.44-1.72 (m, 3H), 1.87-2.01 (m, 1H), 3.16 (s, 1H), 4.07-4.21 (m, 2H), 4.52 (d, J=8.5 Hz, 1H), 4.83 (d, J=8.5 Hz, 1H), 6.74 (d, J=1.5 Hz, 1H), 6.81-6.86 (m, 1H), 7.06 (dd, J=8.3, 2.8 Hz, 1H), 7.10-7.16 (m, 1H), 7.37 (dd, J=8.3, 1.8 Hz, 1H), 7.48-7.54 (m, 1H), 7.81 (s, 1H).

(Conditions for HPLC for Optical Purity Measurement)
Column: CHIRALPAK OD-3R 4.6×150 mm, 3 μm
Mobile phase: 10 mM phosphate buffer:MeCN=40:60
Flow rate: 1.0 min/min
Column temperature: 40° C.
Detection wavelength: 254 nm
Injection quantity: 5 μL
Retention time: title compound=13.8 min, enantiomer=12.9 min Example 3

Ethyl (3'R,4'S,5'R)-6"-chloro-4'-(2-chloro-3-fluoropyridin-4-yl)-2"-oxo-1",2"-dihydrodispiro[cyclohexane-1,2'-pyrrolidine-3',3"-indole]-5'-carboxylate

[Formula 59]

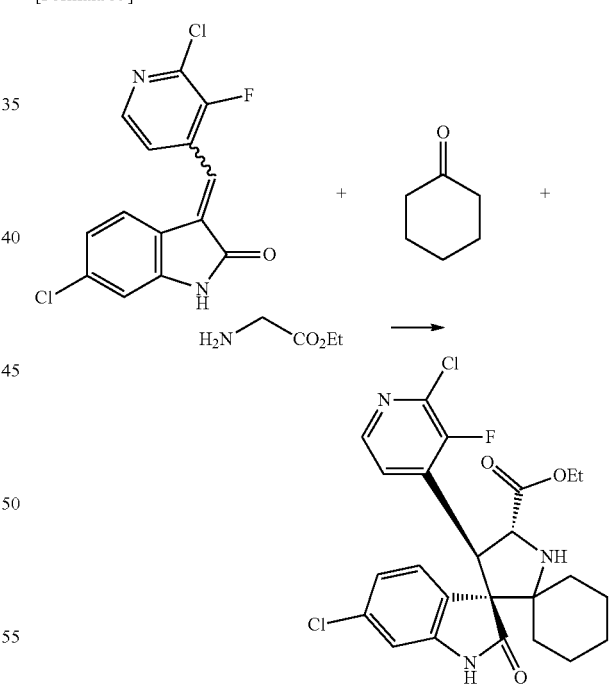

To a mixture of (3E/Z)-6-chloro-3-[(2-chloro-3-fluoropyridin-4-yl)methylene]-1,3-dihydro-2H-indol-2-one (WO2012/121361) (99.2 mg), (R)-BINAP (12.1 mg, 0.019 mmol), and CuOAc (2.0 mg, 0.016 mmol), a solution of cyclohexanone (50.4 μL, 0.49 mmol), glycine ethyl ester (39.6 μL, 0.39 mmol), and triethylamine (6.8 μL, 0.049 mmol) in N,N-dimethylacetamide (2.0 mL) was added under a nitrogen atmosphere, and the resulting mixture was stirred at 0° C. for 18 hours. To the reaction mixture, ethyl acetate (2 mL), water (1 mL), and a 20% aqueous ammonium chloride solution (1 mL) were added, and the mixture was vigorously stirred to separate an organic layer. The aqueous layer was subjected to extraction with ethyl acetate twice (2 mL each), and the organic layers were all combined and then washed with water three times (5 mL each). The organic layer obtained was concentrated under reduced pressure, and the residue was purified by silica gel chromatography [heptane:ethyl acetate=1:1 (v/v)]. To the residue obtained, ethanol (1.0 mL) was added, then water (1 mL) was added dropwise, and the mixture was stirred overnight at room temperature. The deposited solid was filtered and dried under reduced pressure at 40° C. to obtain the title compound (101.2 mg, yield: 64%, 99% ee) as a solid.

$^1$H NMR (500 MHz, CDCl$_3$): δ=0.9-1.1 (m, 2H), 1.19 (t, J=7.3 Hz, 3H), 1.44 (td, J=12.9, 3.2 Hz, 1H) m, 1.48-1.70 (m, 1H), 3.2 (s, 1H), 4.12-4.20 (m, 2H), 4.53 (d, J=9.0 Hz, 1H), 4.82 (d, J=10.0 Hz, 1H), 6.77 (d, J=2.0 Hz, 1H), 7.07 (dd, J=8.0, 1.5 Hz, 1H), 7.34 (dd, J=8.3, 1.8 Hz, 1H), 7.5-7.56 (m, 1H), 7.59 (s, 1H), 8.06 (d, J=5.0 Hz, 1H).

(Conditions for HPLC for Optical Purity Measurement)
Column: CHIRALPAK OD-3R 4.6×150 mm, 3 μm
Mobile phase: 10 mM phosphate buffer:MeCN=40:60
Flow rate: 1.0 min/min
Column temperature: 40° C.
Detection wavelength: 254 nm
Injection quantity: 5 μL
Retention time: title compound=7.7 min, enantiomer=8.7 min Example 4

Ethyl (3'R,4'S,5'R)-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxylate

[Formula 60]

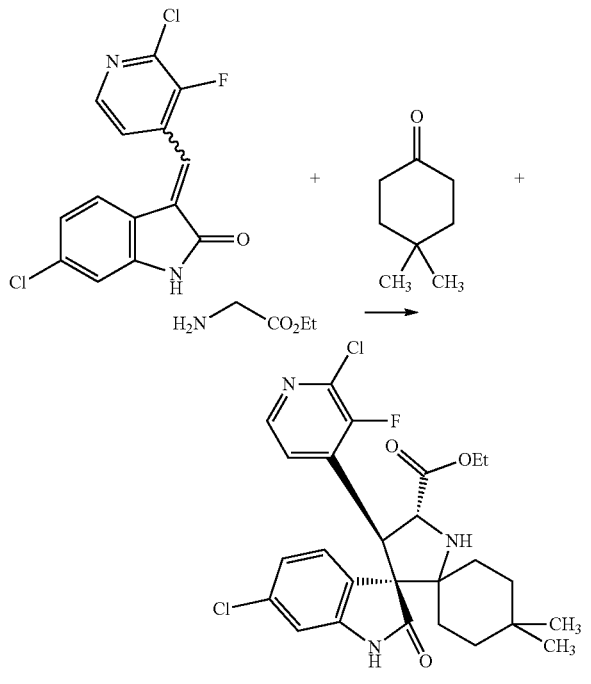

To a mixture of (3E/Z)-6-chloro-3-[(2-chloro-3-fluoropyridin-4-yl)methylene]-1,3-dihydro-2H-indol-2-one (WO2012/121361) (100.7 mg), (R)-BINAP (12.1 mg, 0.019 mmol), and CuOAc (2.0 mg, 0.016 mmol), a solution of 4,4-dimethylcyclohexanone (61.4 mg, 0.48 mmol), glycine ethyl ester (39.5 μL, 0.39 mmol), and triethylamine (6.8 μL, 0.049 mmol) in N,N-dimethylacetamide (2.0 mL) was added under a nitrogen atmosphere, and the resulting mixture was stirred at 0° C. for 14 hours. To the reaction mixture, ethyl acetate (2 mL), water (1 mL), and a 20% aqueous ammonium chloride solution (1 mL) were added, and the mixture was vigorously stirred to separate an organic layer. The aqueous layer was subjected to extraction with ethyl acetate twice (2 mL each), and the organic layers were all combined and then washed with water three times (5 mL each). The organic layer obtained was concentrated under reduced pressure. To the residue, ethyl acetate (6 mL) and silica gel (500 mg) were added, and the silica gel was filtered off. The filtrate was concentrated under reduced pressure. To the residue, ethanol (1.0 mL) was added, then water (1 mL) was added dropwise, and the mixture was stirred overnight at room temperature. The deposited solid was filtered and dried under reduced pressure at 40° C. to obtain the title compound (134.9 mg, yield: 80%, 99% ee) as a solid.

1H NMR (500 MHz, CDCl$_3$): δ=0.67 (s, 3H), 0.91 (s, 3H), 1.11-1.21 (m, 2H), 1.19 (t, J=7.0 Hz, 3H), 1.24-1.34 (m, 1H), 1.43-1.58 (m, 2H), 1.60-1.72 (m, 1H), 1.85-1.95 (m, 1H), 3.19 (s, 1H), 4.10-4.21 (m, 2H), 4.51 (d, J=9.0 Hz, 1H), 4.82 (d, J=9.5 Hz, 1H), 6.77 (d, J=2.0 Hz, 1H), 7.07 (dd, J=8.5, 1.5 Hz, 1H), 7.36 (dd, J=8.3, 1.8 Hz, 1H), 7.5-7.55 (m, 1H), 7.68 (bs, 1H), 8.05 (d, J=5.5 Hz, 1H).

(Conditions for HPLC for Optical Purity Measurement)
Column: CHIRALPAK OD-3R 4.6×150 mm, 3 μm
Mobile phase: 10 mM phosphate buffer:MeCN=40:60
Flow rate: 1.0 min/min
Column temperature: 40° C.
Detection wavelength: 254 nm
Injection quantity: 5 μL
Retention time: title compound=9.4 min, enantiomer=10.5 min Example 5

Ethyl (3'R,4'S,5'R)-6-chloro-4'-(3-chloro-2-fluorophenyl)-3',3'-dimethyl-2-oxo-1,2-dihydrospiro[indole-3,3'-pyrrolidine]-5'-carboxylate

[Formula 61]

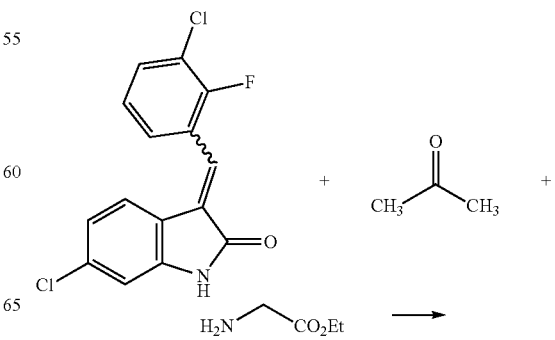

-continued

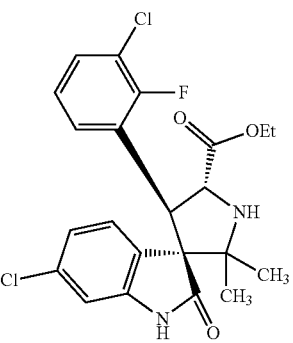

To a mixture of (3E/Z)-6-chloro-3-(3-chloro-2-fluorobenzylidene)-1,3-dihydro-2H-indol-2-one (WO2006/091646) (50.8 mg, 0.16 mmol), (R)-BINAP (6.1 mg, 0.01 mmol), and CuOAc (1.0 mg, 0.008 mmol), a solution of acetone (23.8 µL, 0.32 mmol), glycine ethyl ester (26.4 LL, 0.26 mmol), and triethylamine (3.4 LL, 0.024 mmol) in N,N-dimethylacetamide (1.0 mL) was added under a nitrogen atmosphere, and the resulting mixture was stirred at 0° C. for 42 hours. To the reaction mixture, ethyl acetate (1 mL), water (0.5 mL), and a 20% aqueous ammonium chloride solution (0.5 mL) were added, and the mixture was vigorously stirred to separate an organic layer. The aqueous layer was subjected to extraction with ethyl acetate twice (1 mL each), and the organic layers were all combined and then washed with water three times (2.5 mL each). The organic layer obtained was concentrated under reduced pressure, and the residue was purified by silica gel chromatography [heptane:ethyl acetate:triethylamine=50:50:1 (v/v)] and dried under reduced pressure at 40° C. to obtain a mixture of the title compound and diastereomers (66.8 mg, yield: 90%, diastereomer ratio: 84 (title compound):13:3, optical purity of the title compound: 92% ee) as an oil compound.

$^1$H NMR (500 MHz, CDCl$_3$): δ=1.07 (s, 3H), 1.17 (t, J=7.0 Hz, 3H), 1.48 (s, 3H), 3.40-3.62 (m, 1H), 4.07-4.23 (m, 2H), 4.55 (d, J=9.0 Hz, 1H), 4.91 (d, J=9.5 Hz, 1H), 6.75-6.80 (m, 1H), 6.80 (d, J=1.5 Hz, 1H), 7.06 (dd, J=8.0, 2.0 Hz, 1H), 7.09-7.15 (m, 1H), 7.38 (dd, J=8.3, 2.3 Hz, 1H), 7.45-7.50 (m, 1H), 8.62 (s, 1H).

(Conditions for HPLC for Optical Purity Measurement)

Column: CHIRALPAK IC 4.6×250 mm, 5 µm

Mobile phase: 0.1% HCOOH aq.:MeCN=70:30

Flow rate: 1.0 min/min

Column temperature: 27° C.

Detection wavelength: 254 nm

Injection quantity: 5 µL

Retention time: title compound=10.3 min, enantiomer=11.1 min

Example 6

Ethyl (3'R,4'S,5'R)-6-chloro-4'-(2-chloro-3-fluoropyridin-4-yl)-2-oxo-1,2-dihydrodispiro[indole-3,3'-pyrrolidine-2',4''-pyran]-5'-carboxylate

[Formula 62]

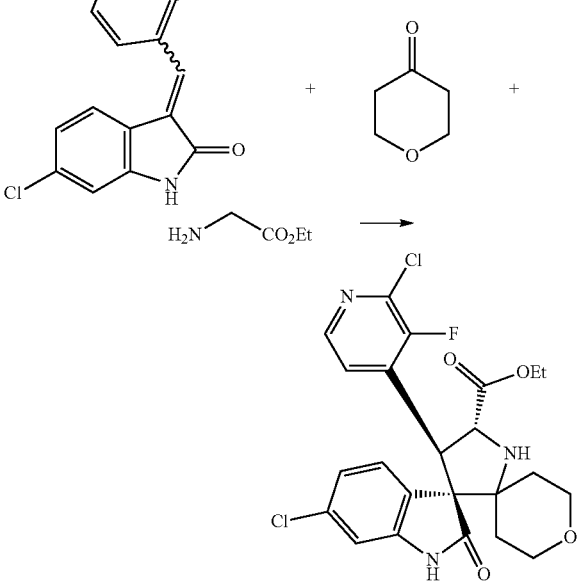

To a mixture of (3E/Z)-6-chloro-3-[(2-chloro-3-fluoropyridin-4-yl)methylene]-1,3-dihydro-2H-indol-2-one (WO2012/121361) (48.7 mg, 0.16 mmol), (R)-BINAP (6.1 mg, 0.01 mmol), and CuOAc (1.0 mg, 0.008 mmol), a solution of tetrahydro-4H-pyran-4-one (22.4 µL, 0.24 mmol), glycine ethyl ester (20 µL, 0.20 mmol), and triethylamine (3.4 LL, 0.024 mmol) in N,N-dimethylacetamide (1.0 mL) was added under a nitrogen atmosphere, and the resulting mixture was stirred at 0° C. for 42 hours. To the reaction mixture, ethyl acetate (1 mL), water (0.5 mL), and a 20% aqueous ammonium chloride solution (0.5 mL) were added, and the mixture was vigorously stirred to separate an organic layer. The aqueous layer was subjected to extraction with ethyl acetate twice (1 mL each), and the organic layers were all combined and then washed with water three times (2.5 mL each). The organic layer obtained was concentrated under reduced pressure, and the residue was purified by silica gel chromatography [heptane:ethyl acetate:triethylamine=50:50:1 (v/v)] and dried under reduced pressure at 40° C. to obtain a mixture of the title compound and diastereomers (74.9 mg, yield: 96%, diastereomer ratio: 75 (title compound):20:5, optical purity of the title compound: 98% ee) as an oil compound.

$^1$H NMR (500 MHz, CDCl$_3$): δ=1.19 (t, J=7.3 Hz, 3H), 1.31-1.41 (m, 1H), 1.42-1.50 (m, 1H), 1.85-1.98 (m, 2H), 3.18-3.38 (m, 1H), 3.67-3.77 (m, 2H), 3.84-3.92 (m, 1H), 3.88-4.06 (m, 1H), 4.08-4.20 (m, 2H), 4.56 (d, J=9.5 Hz, 1H), 4.78 (d, J=9.5 Hz, 1H), 6.79 (d, J=2.5 Hz, 1H), 7.08 (dd, J=8.3, 1.8 Hz, 1H), 7.34 (dd, J=8.3, 2.3 Hz, 1H), 7.49-7.54 (m, 1H), 8.06 (d, J=5.0 Hz, 1H), 8.43 (s, 1H).

(Conditions for HPLC for optical purity measurement)
Column: CHIRALPAK IC 4.6×250 mm, 5 μm
Mobile phase: 10 mM AcOH buffer:MeCN=40:60
Flow rate: 1.0 min/min
Column temperature: 27° C.
Detection wavelength: 220 nm
Injection quantity: 5 μL
Retention time: title compound=26.2 min, enantiomer=22.8 min Example 7

Ethyl (3'R,4'S,5'R)-6-chloro-4'-(2-chloro-3-fluoropyridin-4-yl)-3',3'-dimethyl-2-oxo-1,2-dihydrospiro[indole-3,3'-pyrrolidine]-5'-carboxylate

[Formula 63]

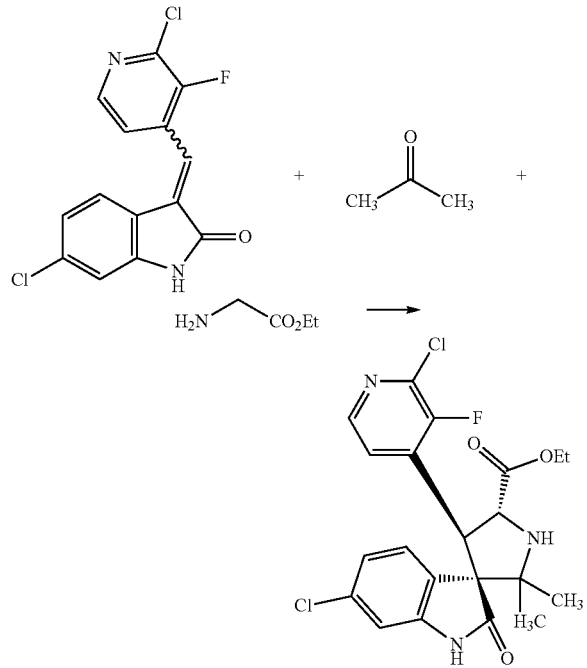

To a mixture of (3E/Z)-6-chloro-3-[(2-chloro-3-fluoropyridin-4-yl)methylene]-1,3-dihydro-2H-indol-2-one (WO2012/121361) (51 mg, 0.16 mmol), (R)-BINAP (6.1 mg, 0.01 mmol), and CuOAc (1.0 mg, 0.008 mmol), a solution of acetone (17.8 μL, 0.24 mmol), glycine ethyl ester (20 μL, 0.20 mmol), and triethylamine (3.4 μL, 0.024 mmol) in N,N-dimethylacetamide (1.0 mL) was added under a nitrogen atmosphere, and the resulting mixture was stirred at 0° C. for 42 hours. To the reaction mixture, ethyl acetate (1 mL), water (0.5 mL), and a 20% aqueous ammonium chloride solution (0.5 mL) were added, and the mixture was vigorously stirred to separate an organic layer. The aqueous layer was subjected to extraction with ethyl acetate twice (1 mL each), and the organic layers were all combined and then washed with water three times (2.5 mL each). The organic layer obtained was concentrated under reduced pressure, and the residue was purified by silica gel chromatography [heptane:ethyl acetate:triethylamine=50:50:1 (v/v)] and dried under reduced pressure at 40° C. to obtain a mixture of the title compound and diastereomers (68.9 mg, yield: 92%, diastereomer ratio: 87 (title compound):13, optical purity of the title compound: 98% ee) as an oil compound.

1H NMR (500 MHz, $CDCl_3$): δ=1.08 (s, 3H), 1.20 (t, J=7.0 Hz, 3H), 1.46 (s, 3H), 3.40-3.65 (m, 1H), 4.09-4.26 (m, 2H), 4.54 (d, J=9.5 Hz, 1H), 4.89 (d, J=9.0 Hz, 1H), 6.79 (d, J=1.5 Hz, 1H), 7.07 (dd, J=8.5, 2.0 Hz, 1H), 7.36 (dd, J=8.0, 1.5 Hz, 1H), 7.49-7.55 (m, 1H), 7.86 (s, 1H), 8.07 (d, J=5.0 Hz, 1H).

(Conditions for HPLC for Optical Purity Measurement)
Column: CHIRALPAK AS-RH 4.6×150 mm, 5 μm
Mobile phase: 10 mM AcOH buffer:MeCN=60:40
Flow rate: 1.0 min/min
Column temperature: 40° C.
Detection wavelength: 254 nm
Injection quantity: 5 μL
Retention time: title compound=8.4 min, enantiomer=7.1 min Example 8

Ethyl (3'R,4'S,5'R)-6"-chloro-4'-(3-chloro-2-fluorophenyl)-2"-oxo-1",2"-dihydrodispiro[cyclopentane-1,2'-pyrrolidine-3',3"-indole]-5'-carboxylate

[Formula 64]

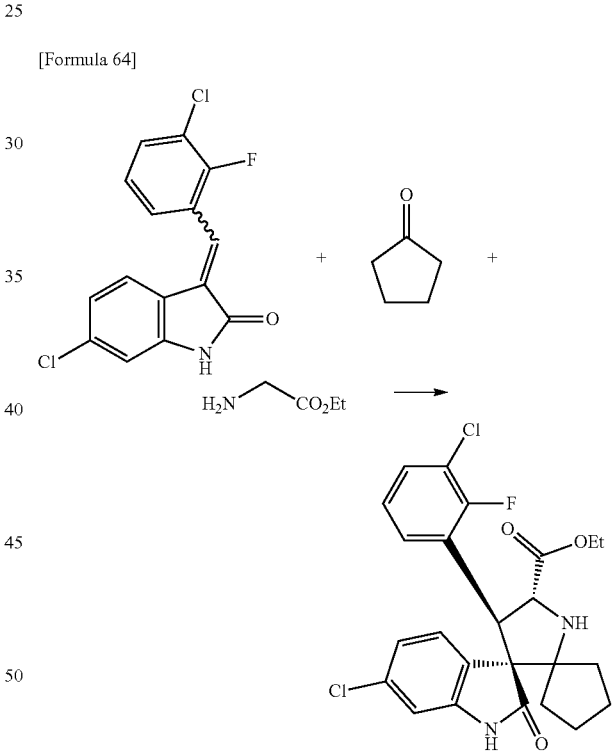

To a mixture of (3E/Z)-6-chloro-3-(3-chloro-2-fluorobenzylidene)-1,3-dihydro-2H-indol-2-one (WO2006/091646) (52.1 mg, 0.17 mmol), (R)-BINAP (6.1 mg, 0.01 mmol), and CuOAc (1.0 mg, 0.008 mmol), a solution of cyclopentanone (28.7 μL, 0.32 mmol), glycine ethyl ester (26.4 LL, 0.26 mmol), and triethylamine (3.4 μL, 0.024 mmol) in N,N-dimethylacetamide (1.0 mL) was added under a nitrogen atmosphere, and the resulting mixture was stirred at 0° C. for 42 hours. To the reaction mixture, ethyl acetate (1 mL), water (0.5 mL), and a 20% aqueous ammonium chloride solution (0.5 mL) were added, and the mixture was vigorously stirred to separate an organic layer. The aqueous layer was subjected to extraction with ethyl acetate twice (1 mL each), and the organic layers were all combined and then washed with water three times (2.5 mL each). The organic layer obtained was concentrated under reduced pressure, and the residue was purified by silica gel chromatography [heptane:ethyl acetate:triethylamine=100:50:1.5 (v/v)] and dried under reduced pressure at 40° C. to obtain a mixture of the title compound and diastereomers (69 mg, yield: 86%, diastereomer ratio: 84 (title compound):14:2, optical purity of the title compound: 99% ee) as an oil compound.

1H NMR (500 MHz, CDCl$_3$): δ=1.17 (t, J=7.3 Hz, 3H), 1.22-1.30 (m, 1H), 1.32-1.42 (m, 1H), 1.50-1.60 (m, 2H), 1.66-1.83 (m, 2H), 1.86-1.97 (m, 1H), 2.07-2.15 (m, 1H), 3.25-3.64 (m, 1H), 4.07-4.23 (m, 2H), 4.53 (d, J=9.5 Hz, 1H), 4.76 (d, J=9.0 Hz, 1H), 6.72-6.77 (m, 1H), 6.80 (d, J=2.0 Hz, 1H), 7.06 (dd, J=8.0, 1.5 Hz, 1H), 7.08-7.13 (m, 1H), 7.38 (dd, J=8.0, 2.0 Hz, 1H), 7.43-7.50 (m, 1H), 8.68 (s, 1H).

(Conditions for HPLC for Optical Purity Measurement)
Column: CHIRALPAK IC 4.6×250 mm, 5 μm
Mobile phase: 0.1% HCOOH aq.:MeCN=50:50
Flow rate: 1.0 min/min
Column temperature: 27° C.
Detection wavelength: 220 nm
Injection quantity: 5 μL
Retention time: title compound=6.0 min, enantiomer=5.6 min Example 9

Ethyl (3'R,4'S,5'R)-6''-chloro-4'-(2-chloro-3-fluoropyridin-4-yl)-2''-oxo-1'',2''-dihydrodispiro[cyclopentane-1,2'-pyrrolidine-3',3''-indole]-5'-carboxylate

[Formula 65]

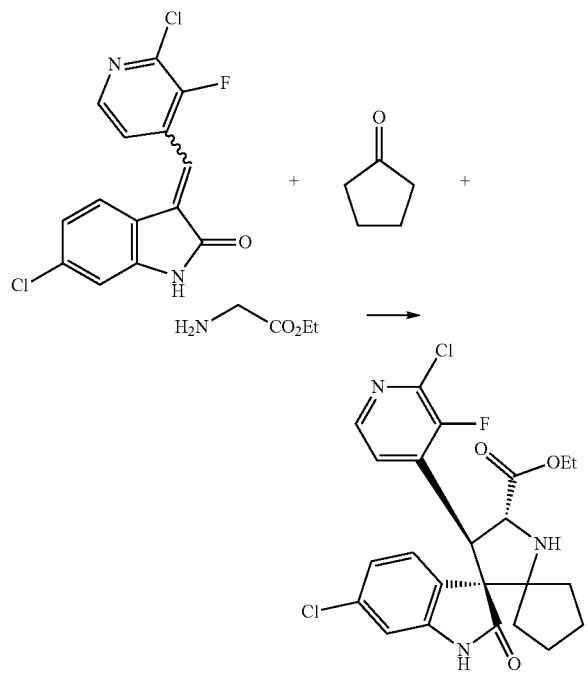

To a mixture of (3E/Z)-6-chloro-3-[(2-chloro-3-fluoropyridin-4-yl)methylene]-1,3-dihydro-2H-indol-2-one (WO2012/121361) (50.9 mg, 0.16 mmol), (R)-BINAP (6.1 mg, 0.01 mmol), and CuOAc (1.0 mg, 0.008 mmol), a solution of cyclopentanone (21.6 μL, 0.24 mmol), glycine ethyl ester (20 μL, 0.20 mmol), and triethylamine (3.4 LL, 0.024 mmol) in N,N-dimethylacetamide (1.0 mL) was added under a nitrogen atmosphere, and the resulting mixture was stirred at 0° C. for 42 hours. To the reaction mixture, ethyl acetate (1 mL), water (0.5 mL), and a 20% aqueous ammonium chloride solution (0.5 mL) were added, and the mixture was vigorously stirred to separate an organic layer. The aqueous layer was subjected to extraction with ethyl acetate twice (1 mL each), and the organic layers were all combined and then washed with water three times (2.5 mL each). The organic layer obtained was concentrated under reduced pressure, and the residue was purified by silica gel chromatography [heptane:ethyl acetate:triethylamine=50:50:1 (v/v)] and dried under reduced pressure at 40° C. to obtain a mixture of the title compound and diastereomers (69.1 mg, yield: 88%, diastereomer ratio: 87 (title compound):13, optical purity of the title compound: 98% ee) as an oil compound.

1H NMR (500 MHz, CDCl$_3$): δ=1.19 (t, J=7.3 Hz, 3H), 1.22-1.30 (m, 1H), 1.32-1.43 (m, 1H), 1.48-1.60 (m, 2H), 1.66-1.82 (m, 2H), 1.86-1.96 (m, 1H), 2.02-2.09 (m, 1H), 3.40-3.62 (m, 1H), 4.08-4.24 (m, 2H), 4.53 (d, J=9.0 Hz, 1H), 4.73 (d, J=9.0 Hz, 1H), 6.82 (d, J=1.5 Hz, 1H), 7.07 (dd, J=8.3, 1.8 Hz, 1H), 7.36 (dd, J=8.3, 2.3 Hz, 1H), 7.50-7.54 (m, 1H), 8.04 (d, J=5.5 Hz, 1H), 8.60 (s, 1H).

(Conditions for HPLC for Optical Purity Measurement)
Column: CHIRALPAK IC 4.6×250 mm, 5 μm
Mobile phase: 0.1% HCOOH aq.:MeCN=50:50
Flow rate: 1.0 min/min
Column temperature: 27° C.
Detection wavelength: 220 nm
Injection quantity: 5 μL
Retention time: title compound=6.7 min, enantiomer=13.3 min Example 10

(3'R,4'S,5'R)—N-[(3R,6S)-6-Carbamoyltetrahydro-2H-pyran-3-yl]-6''-chloro-4'-(2-chloro-3-fluoropyridin-4-yl)-4,4-dimethyl-2''-oxo-1'',2''-dihydrodispiro[cyclohexane-1,2'-pyrrolidine-3',3''-indole]-5'-carboxamide

[Formula 66]

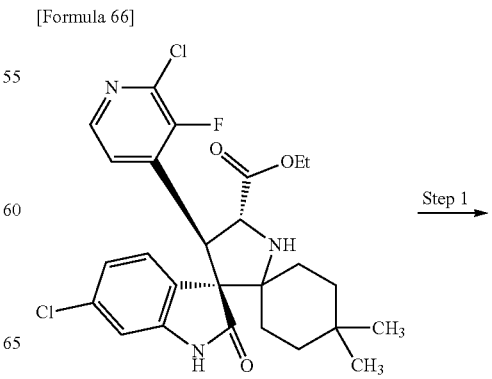

Step 1

-continued

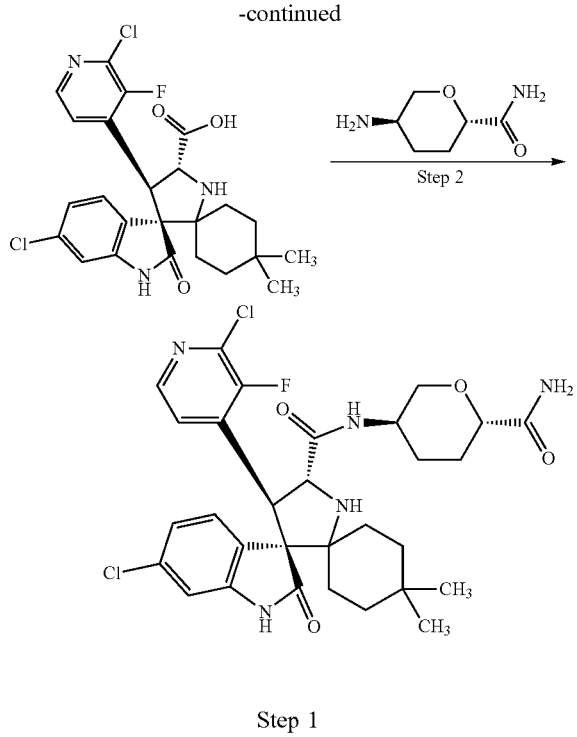

Step 1

(4'S,5'R)-6"-Chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxylic Acid To a solution of the compound (5.00 g, 9.61 mmol) obtained in Example 4 in methanol (25 mL) and tetrahydrofuran (25 mL), a 1 N aqueous sodium hydroxide solution (18.3 mL, 18.3 mmol) was added under ice cooling, and the mixture was stirred at 0° C. for 41.5 hours. The reaction mixture was neutralized to pH 3 by the addition of concentrated hydrochloric acid under ice cooling. Water (75 mL) was added dropwise thereto, and the mixture was then stirred at room temperature for 4 hours. The deposited solid was filtered at 0° C. and dried under reduced pressure at 40° C. to obtain the title compound (4.52 g, yield: 96%) as a solid.

Step 2

(3'R,4'S,5'R)—N-[(3R,6S)-6-Carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide To a solution of the compound (2.00 g, 4.06 mmol) obtained in the preceding step 1 in N,N-dimethylacetamide (20 mL), 1-hydroxybenzotriazole monohydrate (310 mg, 2.02 mmol), (2S,5R)-5-aminotetrahydro-2H-pyran-2-carboxamide (WO2012/121361) (707 mg, 4.90 mmol), diisopropylethylamine (850 LL, 4.88 mmol), and 1-ethyl-3-(3-dimethylaminopropyl)carbodiimide hydrochloride (934 mg, 4.87 mmol) were added, and the mixture was stirred at 0° C. for 47.5 hours. To the reaction mixture, ethyl acetate (20 mL) and water (10 mL) were added, and the mixture was stirred to separate an organic layer. The aqueous layer was subjected to extraction with ethyl acetate twice (20 mL each), and the organic layers were all combined and then washed with water three times (20 mL each). The solvent was distilled off under reduced pressure. To the residue, acetonitrile (30 mL) was then added, and the mixture was stirred at 60° C. for 2 hours. The reaction mixture was allowed to cool, and the deposited solid was then filtered and dried under reduced pressure at 40° C. to obtain the title compound (2.13 g, yield: 80%) as a solid.

Example 11

11-1) Influence of Various Asymmetric Catalysts

[Formula 67]

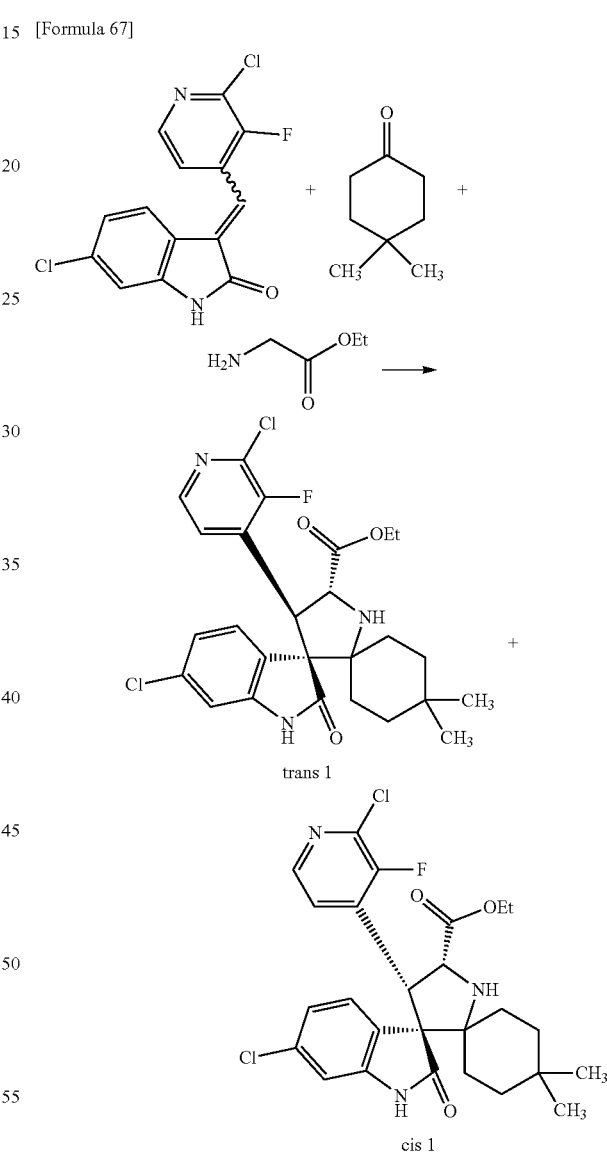

To a solution of (3E/Z)-6-chloro-3-[(2-chloro-3-fluoropyridin-4-yl)methylene]-1,3-dihydro-2H-indol-2-one (WO2012/121361), 4,4-dimethylcyclohexanone (1.5 eq.), glycine ethyl ester (1.2 eq.), and triethylamine (15 mol %) in THF (10-fold amount), a catalyst solution separately prepared by stirring a Lewis acid (5 mol %), a chiral ligand (6 mol %), and THF (10-fold amount) for 1 hour under a nitrogen atmosphere was added under a nitrogen atmosphere, and the mixture was stirred at room temperature for 12 to 16 hours. Then, the optical purity and HPLC yield of the obtained trans-1 compound ((ethyl (3'S,4'R,5'S)-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxylate) were measured by HPLC.

(Conditions for HPLC for Optical Purity Measurement)
Column: CHIRALPAK OD-3R 4.6×150 mm, 3 μm
Mobile phase: 10 mM phosphate buffer:MeCN=40:60
Flow rate: 1.0 min/min
Column temperature: 40° C.
Detection wavelength: 254 nm
Injection quantity: 5 μL
Retention time: title compound=13.8 min, enantiomer=12.9 min Main results are shown in Table 1

TABLE 1

| No. | Ligand | Lewis acid | | |
|---|---|---|---|---|
| | | AgOAc (ee %) | Cu(OTf)$_2$ (ee %) | CuOAc ee % (yield %) |
| 1 | [structure: BINAP] | 31.9 | 34.1 | 88.0 (76.8) |
| 2 | [structure: Tol-BINAP] | 34.9 | 36.6 | 88.8 (76.3) |
| 3 | [structure: Xyl-BINAP] | 32.1 | 18.7 | 76.2 |
| 4 | [structure: H8-BINAP] | 19.1 | 45.8 | 72.6 |

TABLE 1-continued

| No. | Ligand | Lewis acid | | |
|---|---|---|---|---|
| | | AgOAc (ee %) | Cu(OTf)$_2$ (ee %) | CuOAc ee % (yield %) |
| 5 | | 51.6 | 29.4 | 89.0 (74.2) |
| 6 | | 26.0 | 27.9 | 72.5 |
| 7 | | 48.9 | — | 86.9 (76.3) |
| 8 | | 32.9 | — | 43.9 |

11-2) Influence of Various Solvents

[Formula 68]

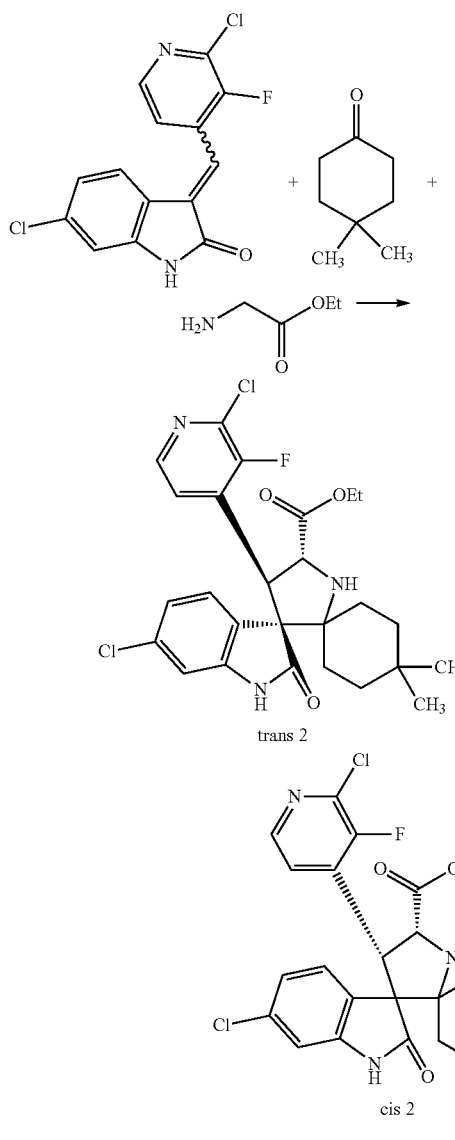

TABLE 2

| No. | Solvent | HPLC yield (%) | ee (%) | trans/cis |
|---|---|---|---|---|
| 1 | THF | 78.7 | 91.3 | 92/8 |
| 2 | MeOH | — | 66.2 | 84/16 |
| 3 | EtOH | — | 72.8 | 86/14 |
| 4 | IPA | — | 83.8 | 85/15 |
| 5 | toluene | — | 87.5 | 9/1 |
| 6 | MeCN | — | 56.4 | 86/14 |
| 7 | DMAc | 85.2 | 97.1 | 94/6 |
| 8 | DME | 85.5 | 93.4 | 93/7 |
| 9 | AcOEt | — | 88.7 | 92/8 |

11-3) Study on Cu(I) Lewis Acid

[Formula 69]

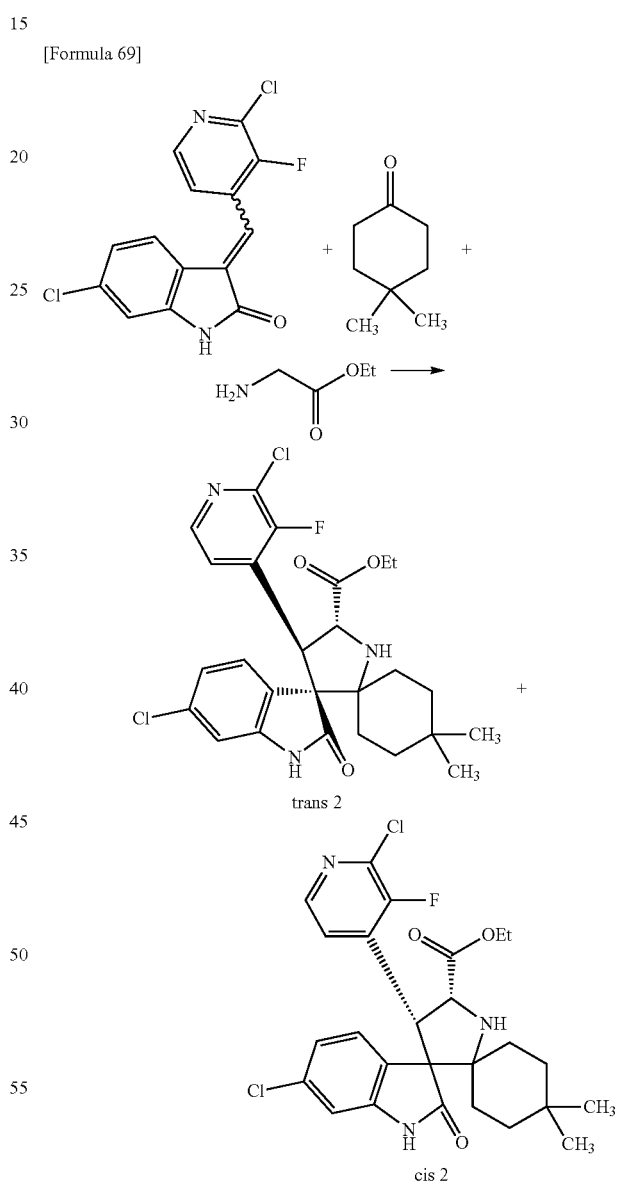

To (3E/Z)-6-chloro-3-[(2-chloro-3-fluoropyridin-4-yl)methylene]-1,3-dihydro-2H-indol-2-one (WO2012/121361), 4,4-dimethylcyclohexanone (1.5 eq.), glycine ethyl ester (1.2 eq.), triethylamine (15 mol %), and a solvent (10-fold amount), a catalyst solution separately prepared by stirring CuOAc (5 mol %), (S)-BINAP (6 mol %), and a solvent (10-fold amount) for 1 hour under a nitrogen atmosphere was added under a nitrogen atmosphere, and the mixture was stirred at room temperature for 21.5 hours. Then, the HPLC yield and optical purity of the obtained trans-2 compound (ethyl (3'S,4'R,5'S)-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxylate) were measured by HPLC.

Main results are shown in Table 2.

To (3E/Z)-6-chloro-3-[(2-chloro-3-fluoropyridin-4-yl)methylene]-1,3-dihydro-2H-indol-2-one (WO2012/121361), 4,4-dimethylcyclohexanone (1.5 eq.), glycine ethyl ester (1.2 eq.), triethylamine (15 mol %), and N,N-dimethylacetamide (10-fold amount), a catalyst solution separately prepared by stirring Cu(I) Lewis acid (5 mol %), (S)-BINAP (6 mol %), and N,N-dimethylacetamide (10-fold amount) for 1 hour under a nitrogen atmosphere was added under a nitrogen atmosphere, and the mixture was stirred at room temperature for 17 to 21.5 hours. Then, the HPLC yield and optical purity of the obtained trans-2 compound (ethyl (3'S,4'R,5'S)-6''-chloro-4'-(2-chloro-3-fluoropyridin-4-yl)-4,4-dimethyl-2''-oxo-1'',2''-dihydrodispiro[cyclohexane-1,2'-pyrrolidine-3',3''-indole]-5'-carboxylate) were measured by HPLC.

Main results are shown in Table 3.

TABLE 3

| No. | Lewis Acid | HPLC yield (%) | ee (%) | trans/cis |
|---|---|---|---|---|
| 1 | CuOAc | 85.2 | 97.1 | 94/6 |
| 2 | CuCl | 38.2 | 52.8 | 87/13 |
| 3 | CuBr | 55.9 | 76.4 | 92/8 |
| 4 | CuI | 72.9 | 89 | 94/6 |
| 5 | $Cu_2O$ | 25.4 | 23.5 | 83/17 |
| 6 | $(CuOTf)_2$ toluene | 84.1 | 95 | 93/7 |
| 7 | $Cu(CH_3CN)_4PF_6$ | 88.6 | 95.9 | 95/5 |
| 8 | $Cu(CH_3CN)_4BF_4$ | 89.1 | 95.8 | 94/6 |

11-4) Study on Cu(II) Lewis Acid

[Formula70]

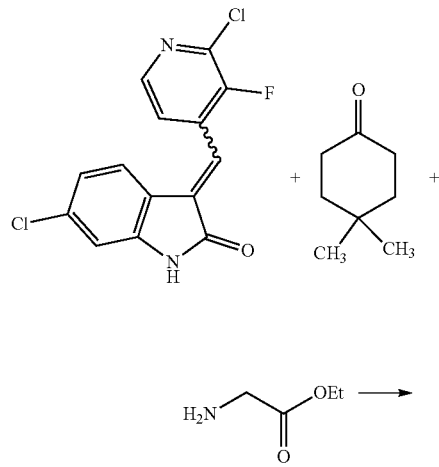

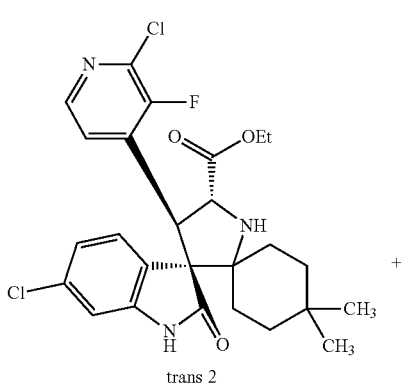

trans 2

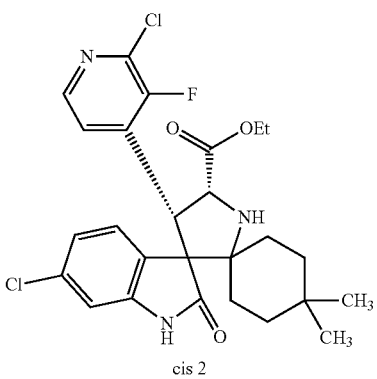

cis 2

(3E/Z)-6-Chloro-3-[(2-chloro-3-fluoropyridin-4-yl)methylene]-1,3-dihydro-2H-indol-2-one (WO2012/121361), 4,4-dimethylcyclohexanone (1.5 eq.), glycine ethyl ester (1.2 eq.), Cu(II) Lewis acid (5 mol %), (R)-BINAP (6 mol %), and N,N-dimethylacetamide (20-fold amount) were stirred at room temperature for 15 hours under a nitrogen atmosphere. Then, the UPLC yield and optical purity of the obtained trans-2 compound (ethyl (3'R,4'S,5'R)-6''-chloro-4'-(2-chloro-3-fluoropyridin-4-yl)-4,4-dimethyl-2''-oxo-1'',2''-dihydrodispiro[cyclohexane-1,2'-pyrrolidine-3',3''-indole]-5'-carboxylate) were measured by UPLC and HPLC, respectively.

Main results are shown in Table 4.

TABLE 4

| No. | Lewis Acid | HPLC yield (%) | ee (%) | trans/cis |
|---|---|---|---|---|
| 1 | $Cu(OAc)_2 \cdot H_2O$ | 79.4 | 97.1 | 95/5 |
| 2 | $Cu(OTf)_2$ | 58.5 | 88.5 | 92/8 |
| 3 | $CuSO_4 \cdot 5H_2O$ | 53.4 | 83.1 | 92/8 |
| 4 | CuO | 14.3 | −13.3 | 49/51 |
| 5 | $CuCl_2$ | 17.8 | −6.7 | 72/28 |
| 6 | $CuBr_2$ | 19.0 | −3.3 | 74/26 |
| 7 | $CuCO_3 \cdot Cu(OH)_2 \cdot H_2O$ | 13.8 | −15.8 | 74/26 |

* Sign "−" in the column "ee" indicates that the trans-2 compound (ethyl (3'S,4'R,5'S)-6''-chloro-4'-(2-chloro-3-fluoropyridin-4-yl)-4,4-dimethyl-2''-oxo-1'',2''-dihydrodispiro[cyclohexane-1,2'-pyrrolidine-3',3''-indole]-5'-carboxylate) was a main product.

11-5) Study Using CuOAc and Various Chiral Ligands

[Formula 71]

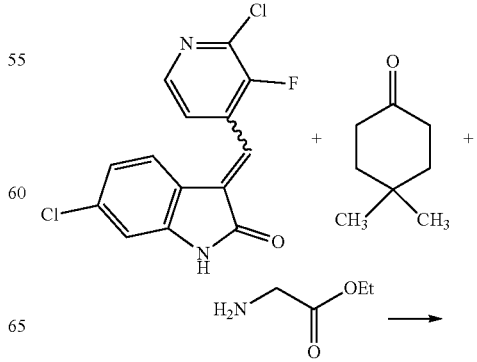

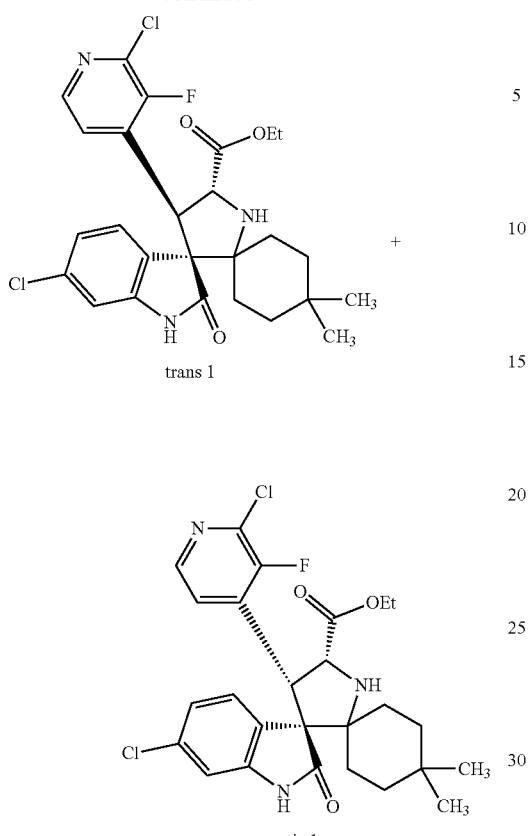

trans 1 cis 1

To a solution of (3E/Z)-6-chloro-3-[(2-chloro-3-fluoro-pyridin-4-yl)methylene]-1,3-dihydro-2H-indol-2-one (WO2012/121361), 4,4-dimethylcyclohexanone (1.5 eq.), glycine ethyl ester (1.2 eq.), and triethylamine (15 mol %) in THF (10-fold amount), a catalyst solution separately prepared by stirring CuOAc (5 mol %), a chiral ligand (6 mol %), and THF (10-fold amount) for 1 hour under a nitrogen atmosphere was added under a nitrogen atmosphere, and the mixture was stirred at room temperature for 12 to 16 hours. Then, the yield and optical purity of the obtained trans-1 compound (ethyl (3'S,4'R,5'S)-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxylate) were measured by HPLC.

Main results are shown in Table 5.

TABLE 5

| No. | Ligand | ee % | Yield % |
|---|---|---|---|
| 1 |  | 88.0 | 76.8 |
| 2 |  | 88.8 | 76.3 |
| 3 |  | 76.2 | — |
| 4 |  | 72.6 | — |
| 5 |  | 89.0 | 74.2 |

TABLE 5-continued

| No. | Ligand | ee % | Yield % |
|---|---|---|---|
| 6 | (3,5-dimethylphenyl)-substituted bis(benzodioxole) diphosphine | 72.5 | — |
| 7 | 2,2'-dimethoxy-6,6'-bis(diphenylphosphino)-1,1'-biphenyl | 91.4 | 79.2 |
| 8 | 2,2'-dimethoxy-6,6'-bis(di-p-tolylphosphino)-1,1'-biphenyl | 90.2 | 76.9 |
| 9 | 2,2'-dimethoxy-6,6'-bis(di-3,5-xylylphosphino)-1,1'-biphenyl | 76.1 | — |
| 10 | 2,2'-dimethoxy-6,6'-bis(di(3,4,5-trimethoxyphenyl)phosphino)-1,1'-biphenyl | 59.9 | — |
| 11 | 2,2'-dimethoxy-6,6'-bis(di(2-furyl)phosphino)-1,1'-biphenyl | 51.4 | — |
| 12 | 2,2',6,6'-tetramethoxy-4,4'-bis(diphenylphosphino)-3,3'-bipyridine | 91.9 | 78.0 |
| 13 | (S)-tBu-PHOX | −54.1 | — |
| 14 | quinoxaline bis(methyl-t-butylphosphino) | 53.0 | — |

TABLE 5-continued

| No. | Ligand | ee % | Yield % |
|---|---|---|---|
| 15 | (structure: biaryl with two OCH2 linker, two PPh2 groups) | 86.9 | 76.3 |
| 16 | (ferrocene with Ph2P, PCy2, CH3) | −85.9 | 71.0 |
| 17 | (ferrocene oxazoline with iPr, PPh2) | −94.6 | 73.7 |
| 18 | (ferrocene with S-t-Bu, PPh2) | −86.2 | 75.5 |

\*: Sign "—" in the column "ee" indicates that the trans-2 compound (ethyl (3'S,4'R,5'S)-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxylate) was a main product.

Example 12 tert-Butyl (3'R,4'S,5'R)-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxylate

[Formula 72]

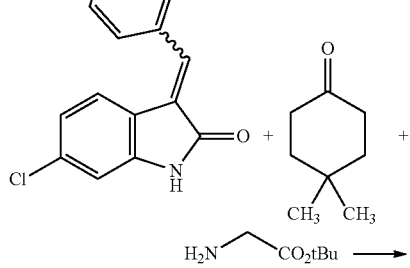

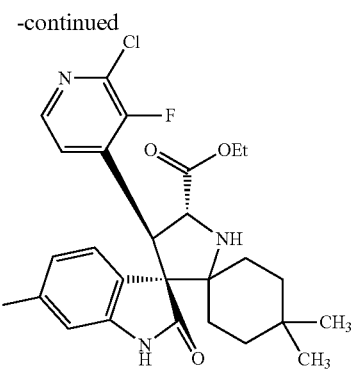

To a mixture of (3E/Z)-6-chloro-3-[(2-chloro-3-fluoropyridin-4-yl)methylene]-1,3-dihydro-2H-indol-2-one (WO2012/121361) (50.0 mg, 0.16 mmol), (R)-BINAP (6.0 mg, 0.009 mmol), and CuOAc (1.0 mg, 0.008 mmol), a solution of 4,4-dimethylcyclohexanone (31.0 mg, 0.25 mmol), glycine tert-butyl ester (27.8 mg, 0.21 mmol), and triethylamine (3.4 μl, 0.024 mmol) in N,N-dimethylacetamide (1.0 ml) was added under a nitrogen atmosphere, and the resulting mixture was stirred at 0° C. for 19.5 hours. To the reaction mixture, ethyl acetate (2.0 ml), water (0.5 ml), and a 20% aqueous ammonium chloride solution (0.5 ml) were added, and the mixture was vigorously stirred to separate an organic layer. The aqueous layer was subjected to extraction with ethyl acetate twice (2.0 ml each), and the organic layers were all combined and then washed with water three times (2.0 ml each). The organic layer obtained was concentrated under reduced pressure, and the residue was purified by silica gel chromatography [heptane:ethyl acetate:triethylamine=50:50:1 (v/v)] and dried under reduced pressure at 40° C. to obtain a mixture of the title compound and a diastereomer (61.0 mg, yield: 69%, diastereomer ratio: 90 (title compound):10, optical purity of the title compound: 97% ee) as an oil compound.

1H NMR (500 MHz, CDCl$_3$): δ=0.67 (s, 3H), 0.92 (s, 3H), 1.10-1.25 (m, 3H), 1.33 (s, 9H), 1.45-1.75 (m, 3H), 1.80-2.00 (m, 2H), 3.15-3.20 (m, 1H), 4.42 (d, J=9.0 Hz, 1H), 4.68 (d, J=9.5 Hz, 1H), 6.77 (d, J=2.0 Hz, 1H), 7.06 (dd, J=8.3, 1.8 Hz, 1H), 7.34 (dd, J=8.5, 2.0 Hz, 1H), 7.53-7.63 (m, 2H), 8.06 (d, J=5.0 Hz, 1H)

(Conditions for HPLC for Optical Purity Measurement)

Column: CHIRALPAK OD-3R 4.6×150 mm, 3 μm

Mobile phase: 0.1% (v/v) HCOOH aq.:MeCN=50:50

Flow rate: 1.0 ml/min

Column temperature: 40° C.

Detection wavelength: 254 nm

Injection quantity: 5 μl

Retention time: title compound=9.4 min, enantiomer=11.4 min

Reference Example 1

(2S,5R)-5-[(2-Aminoacetyl)amino]tetrahydro-2H-pyran-2-carboxamide

[Formula 73]

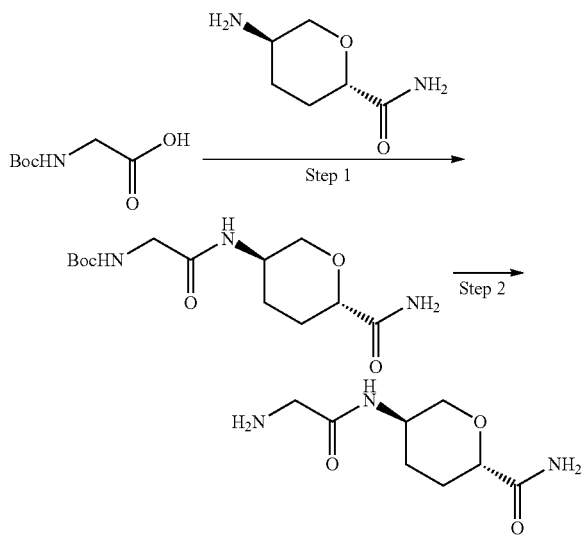

Step 1 tert-Butyl N-(2-{[(3R,6S)-6-carbamoyltetrahydro-2H-pyran-3-yl]amino}-2-oxoethyl)carbamate To a slurry of N-(tert-butoxycarbonyl)glycine (1.01 g, 5.77 mmol), (2S,5R)-5-aminotetrahydro-2H-pyran-2-carboxamide (WO2012/121361) (0.85 g, 5.90 mmol), and diisopropylethylamine (994 μl, 5.71 mmol) in tetrahydrofuran (40 ml), O-(7-azabenzotriazol-1-yl)-N,N,N',N',-tetramethyluronium hexafluorophosphate (2.21 g, 5.83 mmol) was added, and the mixture was stirred at room temperature for 18 hours. The reaction mixture was concentrated under reduced pressure, and the residue was purified by silica gel chromatography [ethyl acetate:methanol=98:2→80:20 (v/v)]. To the solid obtained, ethyl acetate (20 ml) was added, and the mixture was stirred at room temperature for 4 hours. The slurry obtained was filtered and dried under reduced pressure at 40° C. to obtain the title compound (1.47 g, yield: 83%) as a white solid.

$^1$H NMR (500 MHz, CDCl$_3$): δ=1.40-1.50 (m, 1H), 1.46 (s, 9H), 1.57-1.66 (m, 1H), 2.08-2.16 (m, 1H), 2.22-2.28 (m, 1H), 3.09 (t, J=10.5 Hz, 1H), 3.70-3.82 (m, 3H), 3.90-4.02 (m, 1H), 4.16 (ddd, J=10.9, 4.9, 1.9 Hz, 1H), 5.08-5.15 (m, 1H), 5.38-5.46 (m, 1H), 5.95-6.05 (m, 1H), 6.43-6.53 (m, 1H)

Step 2

(2S,5R)-5-[(2-Aminoacetyl)amino]tetrahydro-2H-pyran-2-carboxamide

To the compound (500 mg, 1.66 mmol) obtained in the preceding step 1, a solution of 4 N hydrogen chloride in cyclopentyl methyl ether (5 ml, 20 mmol) was added, and the mixture was stirred at room temperature for 15 hours. The reaction mixture was filtered and washed with cyclopentyl methyl ether (5 ml). To a solution of the solid obtained in methanol (5 ml), a solution of 28% sodium methoxide in methanol (810 μl, 3.32 mmol) was added, and the mixture was stirred at room temperature for 2 hours. To the reaction mixture obtained, neutral silica gel (500 mg) was added, and the mixture was concentrated under reduced pressure. To the residue, ethyl acetate (50 ml) and methanol (5 ml) were added, and the silica gel was filtered off. The filtrate was concentrated under reduced pressure. To the residue, tetrahydrofuran (2.0 ml) was added, and the mixture was stirred at room temperature for 17 hours. The slurry obtained was filtered and dried under reduced pressure at 40° C. to obtain the title compound (111 mg, yield: 33%) as a white solid.

$^1$H NMR (500 MHz, CD$_3$OD): δ=1.50-1.61 (m, 2H), 2.00-2.18 (m, 2H), 3.16 (t, J=10.8 Hz, 1H), 3.21 (d, J=16.5 Hz, 1H), 3.25 (d, J=17.0 Hz, 1H), 3.72-3.78 (m, 1H), 3.80-3.90 (m, 1H), 4.07 (ddd, J=10.9, 4.9, 1.9 Hz, 1H)

Example 13

(3'R,4'S,5'R)—N-[(3R,6S)-6-Carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide

[Formula 74]

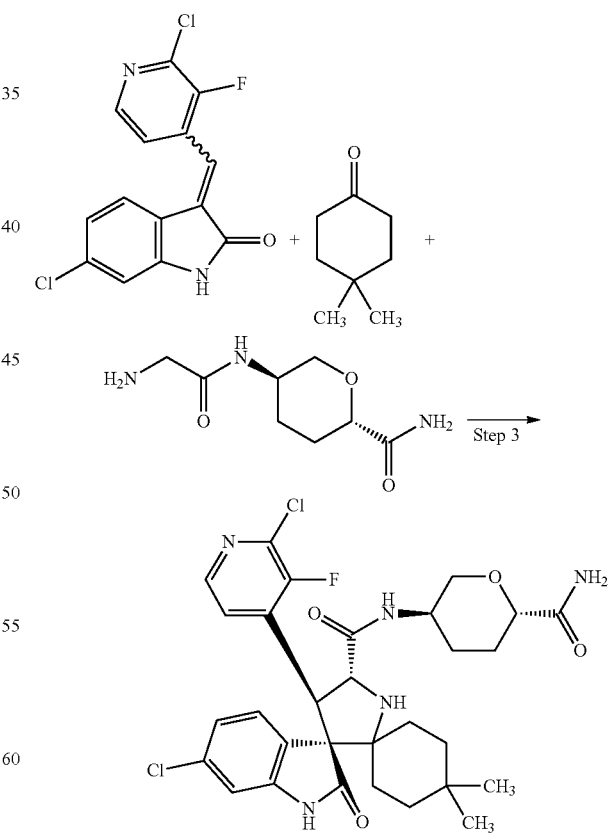

To a mixture of the compound (39.1 mg, 0.19 mmol) obtained in Reference Example 1, (3E/Z)-6-chloro-3-(3-chloro-2-fluorobenzylidene)-1,3-dihydro-2H-indol-2-one (WO2006/091646) (48.6 mg, 0.16 mmol), (R)-BINAP (6.6 mg, 0.011 mmol), and CuOAc (1.2 mg, 0.010 mmol), a solution of 4,4-dimethylcyclohexanone (30.6 mg, 0.24 mmol) in N,N-dimethylacetamide (1.0 ml) was added under a nitrogen atmosphere, and the resulting mixture was stirred at room temperature for 17 hours. The whole amount of the reaction mixture was diluted with methanol (100 ml) to obtain the title compound (ultrahigh-performance liquid chromatography (UHPLC) yield: 65%, 96% de) as a solution in methanol.

(Conditions for UHPLC Measurement for UHPLC Yield Calculation)

Column: CAPCELL CORE ADME 2.1×100 mm, 2.7 m

Mobile phase: 0.1% (v/v) HCOOH aq.:MeCN

Gradient: MeCN 20%→92%

Gradient conditions: 0-2.5 min MeCN 20%, 2.5-7.3 min MeCN 20→92%, 7.3-14 min MeCN 92%, 14.01-17 min MeCN 20%

Flow rate: 0.6 ml/min

Column temperature: 40° C.

Detection wavelength: 254 nm

Injection quantity: 5 μl

Retention time: title compound=6.6 min (Conditions for HPLC for De Measurement)

Column: CHIRALPAK OD-3R 4.6×150 mm, 3 μm

Mobile phase: 0.1% (v/v) HCOOH aq.:MeCN=60:40

Flow rate: 1.0 ml/min

Column temperature: 40° C.

Detection wavelength: 254 nm

Injection quantity: 10 μl

Retention time: title compound=17.7 min, diastereomer=8.5 min

Example 14

(3'R,4'S,5'R)-6"-Chloro-4'-(3-chloro-2-fluorophenyl)-N-(trans-4-hydroxycyclohexyl)-2"-oxo-1",2"-dihydrodispiro[cyclohexane-1,2'-pyrrolidine-3',3"-indole]-5'-carboxamide

[Formula 75]

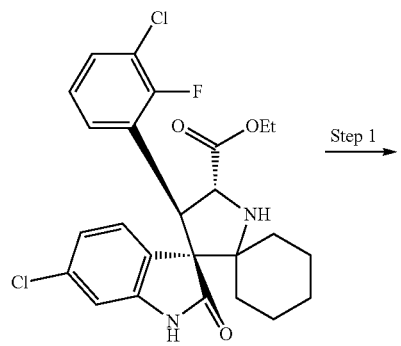

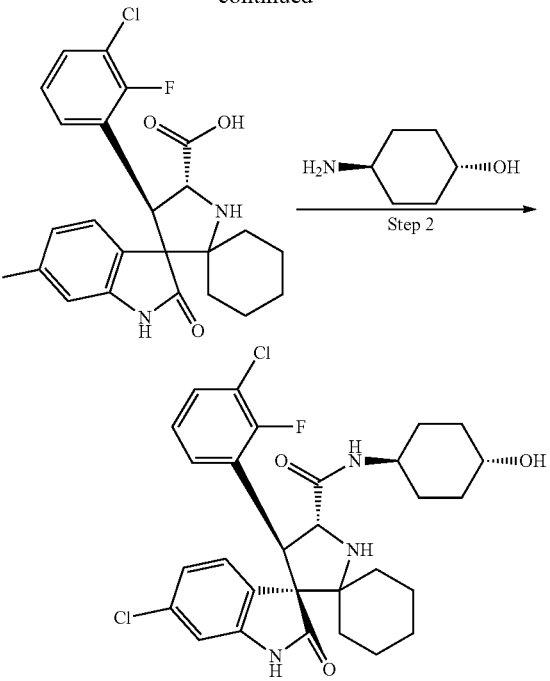

Step 1

(4'S,5'R)-6"-Chloro-4'-(3-chloro-2-fluorophenyl)-N-(trans-4-hydroxycyclohexyl)-2"-oxo-1",2"-dihydrodispiro[cyclohexane-1,2'-pyrrolidine-3',3"-indole]-5"-carboxylic Acid To a slurry of the compound (1.00 g, 2.04 mmol) obtained in Example 1 and methanol (10 ml), a 25% (w/v) aqueous sodium hydroxide solution (1.0 ml, 6.25 mmol) was added under ice cooling, and the mixture was stirred at 0° C. for 27.5 hours. The reaction mixture was neutralized by the addition of 35% (w/w) concentrated hydrochloric acid (651 mg, 6.25 mmol) under ice cooling. Water (15 ml) was added dropwise thereto, and the mixture was then stirred at 0° C. for 18 hours. The deposited crystals were filtered at 0° C. and dried under reduced pressure at 40° C. to obtain the title compound (0.90 g, yield: 95%, >99.5% ee) as a pale yellow solid.

$^1$H NMR (500 MHz, CD$_3$OD): δ=1.10-1.30 (m, 2H), 1.50-1.68 (m, 1H), 1.70-2.13 (m, 5H), 2.18-2.28 (m, 1H), 2.50-2.62 (m, 1H), 4.81 (d, J=10.0 Hz, 1H), 5.01 (d, J=10.0 Hz, 1H), 6.76 (d, J=2.0 Hz, 1H), 7.07-7.15 (m, 2H), 7.28-7.35 (m, 1H), 7.54 (dd, J=8.0, 2.5 Hz, 1H), 7.60-7.68 (m, 1H)

(Conditions for HPLC for Optical Purity Measurement)

Column: CHIRALPAK QN-AX 4.6×150 mm, 3 μm

Mobile phase: 0.1% (v/v) HCOOH aq.:MeCN=60:40

Flow rate: 1.0 ml/min

Column temperature: 40° C.

Detection wavelength: 254 nm

Injection quantity: 5 μl

Retention time: title compound=7.5 min, enantiomer=4.0 min

Step 2

(3'R,4'S,5'R)-6"-Chloro-4'-(3-chloro-2-fluorophenyl)-N-(trans-4-hydroxycyclohexyl)-2"-oxo-1",2"-dihydrodispiro[cyclohexane-1,2'-pyrrolidine-3',3"-indole]-5'-carboxamide To a solution of the compound (501 mg, 1.08 mmol, 99% ee) obtained in the preceding step 1 and trans-4-aminocyclohexanol (157 mg, 1.36 mmol) in N,N-dimethylacetamide (5 ml), 4-(4,6-dimethoxy-1,3,5-triazin-2-yl)-4-methylmorpholinium chloride (392 mg, 1.42 mmol) was added under ice cooling, and the mixture was stirred at 0° C. for 1 hour. To the reaction mixture, ethyl acetate (10 ml) and water (5 ml) were added, and the mixture was stirred to separate an organic layer. The aqueous layer was subjected to extraction with ethyl acetate (10 ml), and the organic layers were all combined and then washed with water three times (10 ml each). The solvent was distilled off under reduced pressure. To the residue, acetonitrile (15 ml) was then added, and the mixture was stirred at room temperature for 18 hours. The deposited crystals were filtered and dried under reduced pressure at 40° C. to obtain the title compound (426 g, yield: 70%, >99.5% ee) as a white solid.

$^1$H NMR (500 MHz, CD$_3$OD): δ=0.93 (td, J=13.5, 4.2 Hz, 1H), 1.0-1.15 (m, 1H), 1.25-1.45 (m, 4H), 1.5-2.05 (m, 12H), 3.5-3.65 (m, 2H), 4.49 (d, J=9.5 Hz, 1H), 4.65 (d, J=9.0 Hz, 1H), 6.71 (d, J=2.0 Hz, 1H), 7.02 (td, J=8.5, 2.0 Hz, 1H), 7.20 (td, J=15.0, 1.5 Hz, 1H), 7.39 (dd, J=8.5, 2.5 Hz, 1H), 7.61 (td, J=14.8, 1.3 Hz, 1H)

(Conditions for HPLC for Optical Purity Measurement)

Column: CHIRALPAK OD-3R 4.6×150 mm, 3 μm

Mobile phase: 0.1% (v/v) HCOOH aq.:MeCN=60:40

Flow rate: 1.0 ml/min

Column temperature: 40° C.

Detection wavelength: 254 nm

Injection quantity: 5 μl

Retention time: title compound=4.9 min, enantiomer=4.2 min

The invention claimed is:

1. A method for producing a compound of formula (XXII) or a salt thereof comprising:

hydrolyzing a compound of formula (XIX):

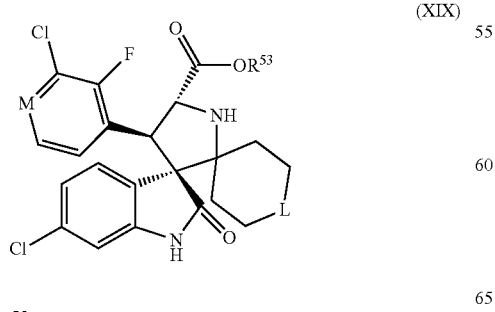
(XIX)

wherein R$^{53}$ is C$_1$-C$_6$ alkyl, to produce a compound of formula (XXI) or a salt thereof;

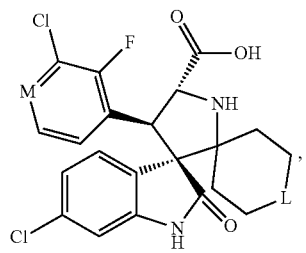
(XXI)

and condensing the compound of formula (XXI) or the salt thereof with a compound having the formula:

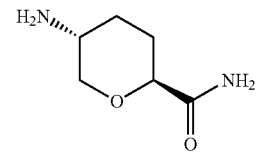

to produce a compound of formula (XXII) or a salt thereof:

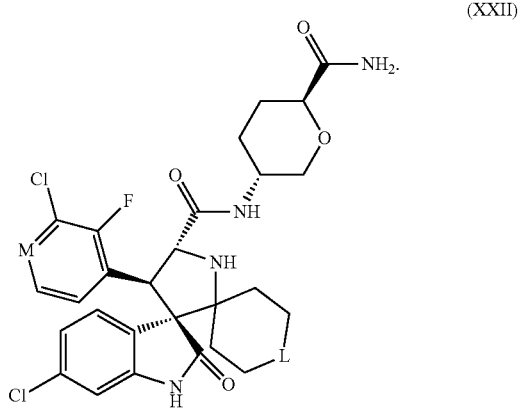
(XXII)

wherein M is a nitrogen atom or CH; and

L is a single bond, an oxygen atom, CH$_2$, or C(CH$_3$)$_2$.

2. A method for producing a compound having formula (XXII):

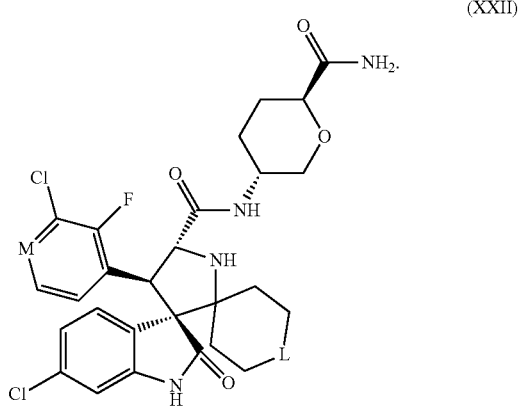
(XXII)

or a salt thereof, the method comprising:
reacting a compound of formula (XVI):
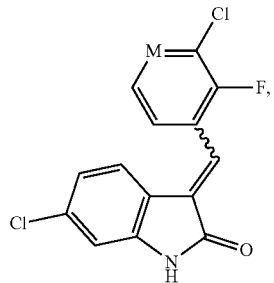
(XVI)
a compound of formula (XVII):
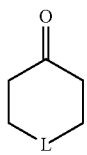
(XVII)
and
a compound of formula (XVIII):
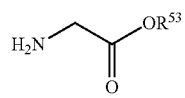
(XVIII)
in a solvent in the presence of a Lewis acid which is Cu(OAc) or Cu(OAc)$_2$ and a chiral ligand selected from:
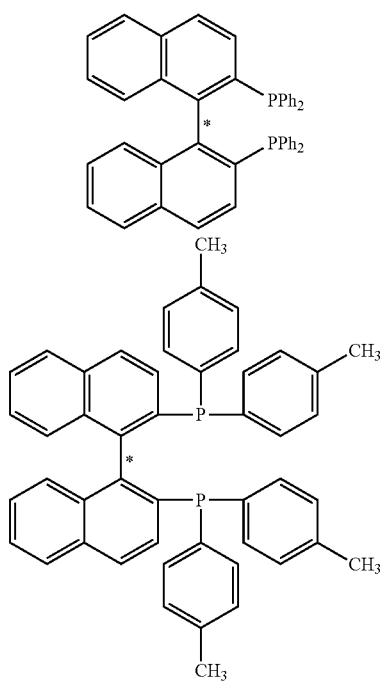
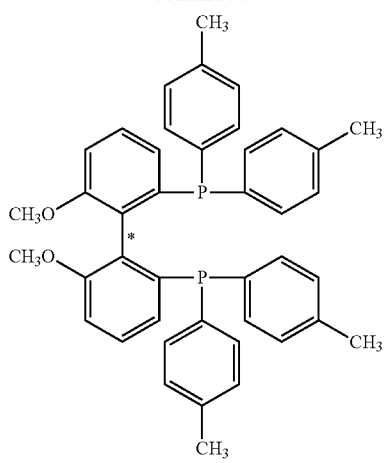
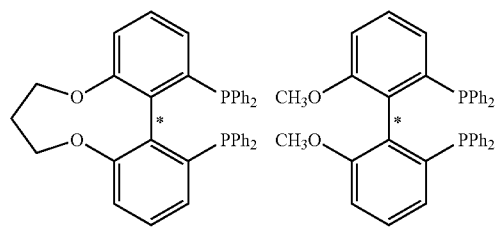
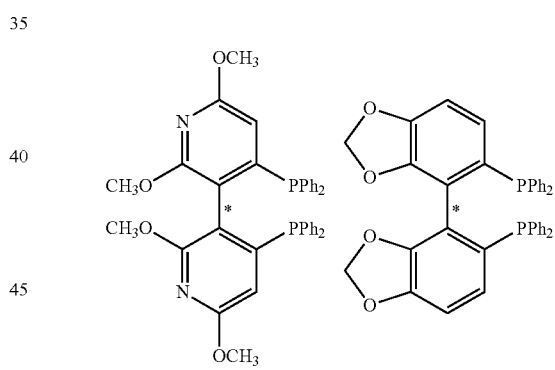
to stereoselectively produce a compound represented by formula (XIX) or a salt thereof,
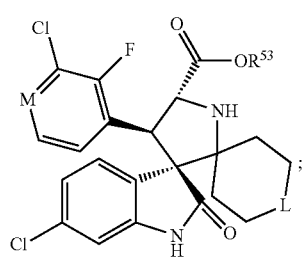
(XIX)

hydrolyzing the compound of formula (XIX) to produce a compound of formula (XXI):

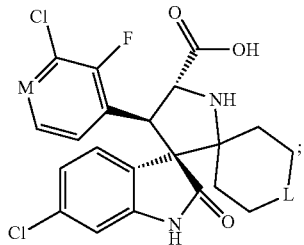 (XXI)

and
condensing the compound of formula (XXI) with (1R, 4R)-4-aminocyclohexane-1-carboxamide:

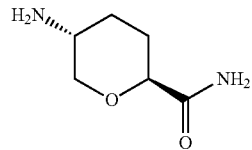

to produce the compound of formula (XXII); wherein
M is N;
L is $C(CH_3)_2$; and
$R^{53}$ is $C_1$-$C_6$ alkyl.

3. The method of claim 2, wherein the chiral ligand has an (R) stereoconfiguration.

4. The method of claim 3, wherein the chiral ligand is (R)-BINAP.

5. The method of claim 2, wherein the Lewis acid is CuOAc.

6. The method of claim 2, wherein $R^{53}$ is ethyl.

* * * * *